(12) United States Patent
Rios-Doria et al.

(10) Patent No.: US 12,214,036 B2
(45) Date of Patent: Feb. 4, 2025

(54) COMBINATION THERAPY COMPRISING AXL/MER AND PD-1/PD-L1 INHIBITORS

(71) Applicant: Incyte Corporation, Wilmington, DE (US)

(72) Inventors: Jonathan Rios-Doria, Wallingford, PA (US); Holly K. Koblish, Exton, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 17/193,631

(22) Filed: Mar. 5, 2021

(65) Prior Publication Data

US 2021/0275666 A1  Sep. 9, 2021

Related U.S. Application Data

(60) Provisional application No. 62/986,482, filed on Mar. 6, 2020.

(51) Int. Cl.
*A61K 39/395* (2006.01)
*A61K 31/53* (2006.01)
*A61K 39/00* (2006.01)
*A61P 35/00* (2006.01)

(52) U.S. Cl.
CPC .......... *A61K 39/3955* (2013.01); *A61K 31/53* (2013.01); *A61P 35/00* (2018.01); *A61K 2039/505* (2013.01); *A61K 2039/54* (2013.01); *A61K 2039/545* (2013.01)

(58) Field of Classification Search
CPC ............... A61K 39/3955; A61K 31/53; A61K 2039/505; A61K 2039/54; A61K 2039/545; A61P 35/00; C07K 2317/52; C07K 16/2818
See application file for complete search history.

(56) References Cited

U.S. PATENT DOCUMENTS

| | | |
|---|---|---|
| 4,399,216 A | 8/1983 | Axel et al. |
| 4,634,665 A | 1/1987 | Axel et al. |
| 5,057,313 A | 10/1991 | Shih et al. |
| 5,156,840 A | 10/1992 | Goers et al. |
| 5,179,017 A | 1/1993 | Axel et al. |
| 5,530,101 A | 6/1996 | Queen et al. |
| 5,585,089 A | 12/1996 | Queen et al. |
| 5,624,821 A | 4/1997 | Winter et al. |
| 5,648,260 A | 7/1997 | Winter et al. |
| 5,693,761 A | 12/1997 | Queen et al. |
| 5,693,762 A | 12/1997 | Queen et al. |
| 5,714,350 A | 2/1998 | Co et al. |
| 5,731,168 A | 3/1998 | Carter et al. |
| 5,849,992 A | 12/1998 | Meade et al. |
| 5,859,205 A | 1/1999 | Adair et al. |
| 5,869,046 A | 2/1999 | Presta et al. |
| 6,300,064 B1 | 10/2001 | Knappik et al. |
| 6,350,861 B1 | 2/2002 | Co et al. |
| 6,407,213 B1 | 6/2002 | Carter et al. |
| 8,791,257 B2 | 7/2014 | Markwalder et al. |
| 9,708,333 B2 | 7/2017 | Li et al. |
| 9,840,503 B2 | 12/2017 | Sun et al. |
| 9,981,975 B2 * | 5/2018 | Li ........................... A61P 35/00 |
| 10,005,788 B2 | 6/2018 | Li et al. |
| 10,053,465 B2 | 8/2018 | Li et al. |
| 10,138,248 B2 | 11/2018 | Buesking et al. |
| 10,442,810 B2 * | 10/2019 | Li ........................ C07D 403/04 |
| 10,519,163 B2 | 12/2019 | Li et al. |
| 10,633,387 B2 * | 4/2020 | Jia ........................ C07D 487/04 |
| 10,844,069 B2 * | 11/2020 | Li ........................ C07D 403/14 |
| 11,104,682 B2 * | 8/2021 | Jia ........................... A61P 35/00 |
| 11,136,326 B2 | 10/2021 | Li et al. |
| 11,241,438 B2 * | 2/2022 | Rocco .................. A61K 9/4858 |
| 11,591,338 B2 | 2/2023 | Li et al. |
| 11,918,585 B2 | 3/2024 | Rocco et al. |
| 2005/0008625 A1 | 1/2005 | Balint et al. |
| 2005/0037000 A1 | 2/2005 | Stavenhagen et al. |
| 2005/0079574 A1 | 4/2005 | Bond |
| 2006/0235031 A1 | 10/2006 | Arnold et al. |
| 2008/0045528 A1 | 2/2008 | Sutton et al. |
| 2010/0298334 A1 | 11/2010 | Rodgers et al. |
| 2011/0015212 A1 | 1/2011 | Li et al. |
| 2011/0059951 A1 | 3/2011 | Rodgers et al. |
| 2011/0183985 A1 | 7/2011 | Li et al. |
| 2011/0224190 A1 | 9/2011 | Huang et al. |
| 2012/0015937 A1 | 1/2012 | Ding et al. |
| 2012/0088768 A1 | 4/2012 | Singh et al. |
| 2012/0149681 A1 | 6/2012 | Rodgers et al. |
| 2012/0149682 A1 | 6/2012 | Rodgers et al. |
| 2012/0157430 A1 | 6/2012 | Li et al. |
| 2012/0184535 A1 | 7/2012 | Brzozka et al. |
| 2012/0219522 A1 | 8/2012 | Xi |
| 2012/0230993 A1 | 9/2012 | Graham et al. |
| 2012/0264740 A1 | 10/2012 | Goff et al. |
| 2012/0283261 A1 | 11/2012 | Bearss et al. |
| 2013/0018034 A1 | 1/2013 | Yao et al. |
| 2013/0018051 A1 | 1/2013 | Singh et al. |

(Continued)

FOREIGN PATENT DOCUMENTS

| | | |
|---|---|---|
| CL | 2018002759 | 9/2018 |
| CL | 2018000949 | 12/2018 |

(Continued)

OTHER PUBLICATIONS

Optum, Inc., "The New Age of Oncology Drugs"; URL = https://www.optum.com/business/insights/state-government/page.hub.oncology-drug-advances.html; Accessed Jun. 21, 2023; (C) 2023 by Optum, Inc. (Year: 2023).*

(Continued)

*Primary Examiner* — Julie Wu
*Assistant Examiner* — Sydney Van Druff
(74) *Attorney, Agent, or Firm* — Fish & Richardson P.C.

(57) ABSTRACT

The present disclosure relates to methods of treating cancer by administering a compound, which is an AXL/MER kinase inhibitor, in combination with an antibody, or an antibody fragment thereof, that binds to PD-1.

17 Claims, 10 Drawing Sheets

Specification includes a Sequence Listing.

(56) References Cited

U.S. PATENT DOCUMENTS

| | | |
|---|---|---|
| 2013/0045963 A1 | 2/2013 | Rodgers et al. |
| 2013/0059835 A1 | 3/2013 | Li et al. |
| 2013/0090330 A1 | 4/2013 | Ding et al. |
| 2013/0137702 A1 | 5/2013 | Steiner et al. |
| 2013/0197070 A1 | 8/2013 | De Franciscis et al. |
| 2013/0281468 A1 | 10/2013 | Goff et al. |
| 2014/0005166 A1 | 1/2014 | Rodgers et al. |
| 2014/0018365 A1 | 1/2014 | Schultz-Fademrecht et al. |
| 2014/0121198 A1 | 5/2014 | Li et al. |
| 2014/0128390 A1 | 5/2014 | Lin |
| 2014/0128400 A1 | 5/2014 | Singh et al. |
| 2014/0275023 A1 | 9/2014 | Namdev et al. |
| 2015/0031676 A1 | 1/2015 | Lobell et al. |
| 2016/0333008 A1 | 11/2016 | Sun et al. |
| 2017/0044164 A1 | 2/2017 | Li et al. |
| 2017/0057965 A1 | 3/2017 | Li et al. |
| 2017/0275290 A1* | 9/2017 | Li ..................... A61P 35/00 |
| 2017/0334884 A1 | 11/2017 | Petersen |
| 2018/0009815 A1 | 1/2018 | Li et al. |
| 2018/0327412 A1 | 11/2018 | Li et al. |
| 2019/0031663 A1 | 1/2019 | Li et al. |
| 2019/0112313 A1 | 4/2019 | Jia et al. |
| 2020/0000812 A1 | 1/2020 | Rocco et al. |
| 2020/0131185 A1 | 4/2020 | Li et al. |
| 2020/0181151 A1 | 6/2020 | Li et al. |
| 2020/0347065 A1 | 11/2020 | Jia et al. |
| 2021/0047430 A1* | 5/2021 | Li ..................... C07D 487/04 |
| 2022/0022770 A1* | 7/2022 | Jia ..................... C07D 487/04 |
| 2022/0273663 A1 | 9/2022 | Rocco et al. |
| 2024/0124463 A1 | 4/2024 | Li et al. |

FOREIGN PATENT DOCUMENTS

| | | |
|---|---|---|
| CL | 2019000043 | 6/2019 |
| CL | 2019000115 | 6/2019 |
| CN | 101084218 | 12/2007 |
| CN | 102408411 | 4/2012 |
| CN | 102918045 | 2/2013 |
| CN | 101641093 | 5/2013 |
| CN | 103124729 | 5/2013 |
| CN | 103608342 | 2/2014 |
| CN | 102482278 | 4/2015 |
| CN | 105732634 | 7/2016 |
| CO | 2021/0000923 | 4/2021 |
| EP | 0404097 | 12/1990 |
| EP | 2320902 | 5/2011 |
| EP | 2465505 | 6/2012 |
| EP | 2484679 | 8/2012 |
| EP | 2552922 | 2/2013 |
| EP | 2810937 | 12/2014 |
| EP | 2791140 | 6/2016 |
| ES | 2253774 | 6/2006 |
| ES | 2307003 | 11/2008 |
| ES | 2351612 | 2/2011 |
| IN | 201817040446 | 2/2019 |
| JP | H03-95163 | 4/1991 |
| JP | 2008-501703 | 1/2008 |
| JP | 2009-518303 | 5/2009 |
| JP | 2009-519222 | 5/2009 |
| JP | 2009-519905 | 5/2009 |
| JP | 2010-522742 | 7/2010 |
| JP | 2010-529196 | 8/2010 |
| JP | 2012-525400 | 10/2012 |
| JP | 2014-525902 | 10/2014 |
| JP | 2015-532287 | 11/2015 |
| JP | 2019-510043 | 4/2019 |
| JP | 2021-529765 | 11/2021 |
| KR | 2013-0141706 | 12/2013 |
| KR | 2015-0061651 | 6/2015 |
| WO | WO 1990/07861 | 7/1990 |
| WO | WO 1993/11161 | 6/1993 |
| WO | WO 2001/019828 | 3/2001 |
| WO | WO 2002/000196 | 1/2002 |
| WO | WO 2002/080975 | 10/2002 |
| WO | WO 2004/026840 | 4/2004 |
| WO | WO 2004/035580 | 4/2004 |
| WO | WO 2005/003175 | 1/2005 |
| WO | WO 2005/018572 | 3/2005 |
| WO | WO 2005/025515 | 3/2005 |
| WO | WO 2006/046023 | 5/2006 |
| WO | WO 2006/056399 | 6/2006 |
| WO | WO 2007/061737 | 5/2007 |
| WO | WO 2007/064883 | 6/2007 |
| WO | WO 2007/070514 | 6/2007 |
| WO | WO 2007/120752 | 10/2007 |
| WO | WO 2007/125315 | 11/2007 |
| WO | WO 2008/048375 | 4/2008 |
| WO | WO 2008/076392 | 6/2008 |
| WO | WO 2018/198077 | 11/2008 |
| WO | WO 2009/022354 | 2/2009 |
| WO | WO 2009/023269 | 2/2009 |
| WO | WO 2009/047514 | 4/2009 |
| WO | WO 2009/053737 | 4/2009 |
| WO | WO 2009/054864 | 4/2009 |
| WO | WO 2009/085185 | 7/2009 |
| WO | WO 2009/087225 | 7/2009 |
| WO | WO 2009/127417 | 10/2009 |
| WO | WO 2009/134723 | 11/2009 |
| WO | WO 2010/005876 | 1/2010 |
| WO | WO 2010/005879 | 1/2010 |
| WO | WO 2010/008454 | 1/2010 |
| WO | WO 2010/014755 | 2/2010 |
| WO | WO 2010/025073 | 3/2010 |
| WO | WO 2010/071885 | 6/2010 |
| WO | WO 2010/090764 | 8/2010 |
| WO | WO 2011/038185 | 3/2011 |
| WO | WO 2011/045084 | 4/2011 |
| WO | WO 2011/139273 | 11/2011 |
| WO | WO 2011/146313 | 11/2011 |
| WO | WO 2012/028332 | 3/2012 |
| WO | WO 2012/048129 | 4/2012 |
| WO | WO 2012/129344 | 9/2012 |
| WO | WO 2012/135800 | 10/2012 |
| WO | WO 2012/174082 | 12/2012 |
| WO | WO 2013/040286 | 3/2013 |
| WO | WO 2013/052417 | 4/2013 |
| WO | WO 2013/074633 | 5/2013 |
| WO | WO 2013/085802 | 6/2013 |
| WO | WO 2013/115280 | 8/2013 |
| WO | WO 2013/162061 | 10/2013 |
| WO | WO 2014/062774 | 4/2014 |
| WO | WO 2014/079545 | 5/2014 |
| WO | WO 2014/109858 | 7/2014 |
| WO | WO 2014/164729 | 10/2014 |
| WO | WO 2015/012298 | 1/2015 |
| WO | WO 2015/068767 | 5/2015 |
| WO | WO 2015/081783 | 6/2015 |
| WO | WO 2015/132799 | 9/2015 |
| WO | WO 2016/097918 | 6/2016 |
| WO | WO 2016/183071 | 11/2016 |
| WO | WO 2017/027717 | 2/2017 |
| WO | WO-2017019846 A1 * | 2/2017 ............. A61P 1/04 |
| WO | WO 2017/062797 | 4/2017 |
| WO | WO 2017/083788 | 5/2017 |
| WO | WO 2017/083789 | 5/2017 |
| WO | WO 2017/172596 | 10/2017 |
| WO | WO 2017/184934 | 10/2017 |
| WO | WO 2019/067594 | 4/2019 |

OTHER PUBLICATIONS

Affouard et al., "Multi-Kilo Delivery of AMG 925 Featuring a Buchwald-Hartwig Amination and Processing with Insoluble Synthetic Intermediates," Organic Process Research & Development, 2015, 19: 476-485.

Angal et al., "A single amino acid substitution abolishes the heterogeneity of chimeric mouse/human (IgG4) antibody," Mol. Immunol., 1993, 30:105-108.

Angelillo-Scherrer et al., "Role of Gas6 in erythropoiesis and anemia in mice," J. Clin. Invest., 2008, 118: 583-596.

Anonymous: "Study Record Versions History of Changes for Study: NCT03522142 a Study Exploring the Safety and Tolerability of

(56) References Cited

OTHER PUBLICATIONS

INCB081776 in Participants With Advanced Malignancies," Mar. 20, 2020[retrieved on Jun. 4, 2021], retrieved from URL <https://clinicaltrials.gov/ct2/history/NCT03522142?A=8&8=8&C=merged#StudyPageTop>, 10 pages.
Ash and Ash, "Handbook of Pharmaceutical Additives," Gower Publishing Company, 2007, 3rd Edition, 1 page, Title Page.
Australian Office Action in Australian Application No. 2017241524, Jun. 26, 2020, 4 pages.
Avilla et al., "Activation of TYRO3/AXL tyrosine kinase receptors in thyroid cancer," Cancer Res., Mar. 1, 2011, 71(5):1792-1804.
Badaway et al., "Salt Selection for Pharmaceutical Compounds," Preformulation in Solid Dosage Form Development(Informa Healthcare), 2008, Chapter 2.3, 63-80.
Baladi et al., "State-of-the-art of small molecule inhibitors of the TAM family: The point of view of the chemist," European Journal of Medicinal Chemistry, Oct. 2015, 105: 220-237.
Balupuri et al., "Molecular modeling study on Mer kinase inhibitors using 3D-QSAR and docking approaches," Medicinal Chemistry Research, Jul. 2015, 24(10): 3730-3742.
Bastin et al., "Salt Selection and Optimization Procedures for Pharmaceutical New Chemicalls Entities," Organic Process Research & Development, 2000, 4(5):427-435.
Ben-Batalla et al., "Axl Blockade by BGB324 Inhibits BCR-ABL Tyrosine Kinase Inhibitor-Sensitive and -Resistant Chronic Myeloid Leukemia," Clinical Cancer Research, May 1, 2017, 23(9):2289-2300.
Ben-Batalla., "Axl, a prognostic and therapeutic target in acute myeloid leukemia mediates paracrine crosstalk of leukemia cells with bone marrow stroma," Blood, Oct. 3, 2013, 122(14):2443-2452.
Berge, "Pharmaceutical Salts," Journal of Pharmaceutical Science, 1997, 66(1):1-19.
Berraondo et al., "Cytokines in clinical cancer immunotherapy," British Journal of Cancer, 2019, 120:6-15.
Better et al., "*Escherichia coli* secretion of an active chimeric antibody fragment," Science, 1988, 240:1041-1043.
Better, "Expression of engineered antibodies and antibody fragments in microorganisms," Methods in Enzymology, 1989, 178:476-496.
Bird et al., "Single chain antibody variable regions," Trends Biotechnol., Apr. 1991, 9:132-137.
Blom et al., "Optimizing Preparative LC/MS Configurations and Methods for Parallel Synthesis Purification," J. Comb. Chem., 2003, 5: 670-683.
Blom et al., "Preparative LC-MS Purification: Improved Compound-Specific Method Optimization," J. Comb. Chem., 2004, 6: 874-883.
Blom, "Two-Pump at-Column-Dilution Configuration for Preparative Liquid Chromatography-Mass Spectrometry," J. Comb. Chem., 2002, 4: 295-301.
Borovik et al., "Pyrimidines. XLIX. Synthesis of 9-phenylpyrimido[4,5-b] indoles," Izvestiya Sibirskogo Otdeleniya Akademii Nauk SSSR, Seriya Khimicheskikh Nauk , 1975, 137-41 (English abstract only).
Borovik et al., "Synthesis of 2-substituted pyrimido[4,5-b]indoles and N-phenyl-2,2-diethoxy-3-arylideneindolines," v sb., Khimiya i Farmakol. Indol'n. Soedinenii, 1975, 50 (English abstract only).
Boyd, "Some practical considerations and applications of the national cancer institute in vitro anticancer drug discovery screen," Drug Development Research, Feb. 1995, 34(2):91-109.
Brazilian Office Action in Brazilian Application No. BR112020006145-0, dated Sep. 9, 2022, 7 pages.
Brunton et al., "Chemotherapy of Neoplastic Diseases," Goodman & Gilman's: The Pharmacological Basis of Therapeutics, 2008, pp. 853-908.
Burbridge et al., "S49076 Is a Novel Kinase Inhibitor of MET, AXL, and FGFR with Strong Preclinical Activity Alone and in Association with Bevacizumab," AACR Journals, 2013, 1749-1762.
Carter et al., "High level *Escherichia coli* expression and production of a bivalent humanized antibody fragment," Bio/Technology, 1992, 10:163-167.
Carter et al., "Humanization of an anti-p185HER2 antibody for human cancer therapy," PNAS, 1992, 89: 4285-4289.
Cecil Textbook of Medicine, edited by Bennet, J.C., and Plum F., 20th edition, vol. 1, 1004-1010, 1996.
Chambers et al., "Lymphoproliferation in CTLA-4-deficient mice is mediated by costimulation-dependent activation of CD4+ T cells," Immunity, Dec. 1997, 7(6): 885-95.
Chilean Office Action in Chilean Application No., 202003397, dated Jun. 13, 2022, 14 pages.
Chilean Office Action in Chilean Application No. 202000791, dated Jul. 15, 2021, 34 pages.
Chinese Office Action in Chinese Application No. 201780031476.3, dated Oct. 28, 2020, 16 pages.
Chinese Office Action in Chinese Application No. 201980055116.6, dated Jun. 22, 2022, 12 pages.
Chothia et al., "Structural repertoire of the human VH segments," J Mol Bio., 1992, 227:799-817.
Chow et al., "Engineered of Pharmaceutical Materials: an Industrial Perspective," J Pharmaceutical Sciences., Aug. 2008, 97(8):2855-2877.
Chung et al., "Synthesis of certain [6:5:6] linear tricyclic nucleosides as potential antitumor agents," Journal of Medicinal Chemistry, Nov. 1980, 23(11): 1158-66.
Co et al., "A humanized antibody specific for the platelet integrin gpIIb/IIIa," J Immunol., Mar. 15, 1994, 152(6):2968-2976 (Abstract Only).
Cohen., "The development and therapeutic potential of protein kinase inhibitors," Current Opinion in Chemical Biology, 1999, 3: 459-465, 1999.
Colombian Office Action in Colombian Application No. NC2018/0011550, dated May 29, 2020, 16 pages.
Colombian Office Action in Colombian Application No. NC2020/0005009, dated May 27, 2022, 22 pages.
Colombian Office Action in Colombian Application No. NC2021/0004423, Aug. 2, 2021, 20 pages.
Cook et al., "MerTK inhibition in tumor leukocytes decreases tumor growth and metastasis," J. Clin. Invest., Aug. 2013, 123(8): 3231-42.
Cook et al., "The human immunoglobulin VH repertoire," Immunol Today., 1995, 16: 237-242.
Cosemans et al., "Potentiating role of Gas6 and Tryo3, Axl and Mer (TAM) receptors in human and murine platelet activation and thrombus stabilization," J. of Thrombosis and Haemostasis, 2010, 8: 1797-1808.
Costa Rican Office Action in Costa Rican Application No. 2018-0516, dated May 4, 2022, 12 pages.
Cruz-Cabeza et al., "Facts and Fictions about Polymorphism," Chemical Society Reviews, 2015, 44:8619-8635.
Datta et al., "Crystal Structures of Drugs: Advances in Determination, Prediction and engineering," Nature, Jan. 2004, 3:42-57.
Davies et al., "Single antibody domains as small recognition units: design and in vitro antigen selection of camelized, human VH domains with improved protein stability," Protein Eng., 1996, 9(6):531-537.
Demarest et al., "Evaluation of Tyro3 expression, Gas6-mediated Akt phosphorylation, and the impact of anti-Tyro3 antibodies in melanoma cell lines," Biochemistry, May 2013, 52(18): 3102-18.
Dermer et al., "Another Anniversary for the War on Cancer," Bio/Technology, Mar. 1994, 12: 320.
Devi et al, "Poloxamer: A Novel Functional Molecule for Drug Delivery and Gene Therapy," J. Pharm. Sci. & Res., 2013, 5(8): 159-165.
Divine et al., "AXL modulates extracellular matrix protein expression and is essential for invasion and metastasis in endometrial cancer," Oncotarget, Nov. 22, 2016, 7(47):77291-77305.
Dodonova et al., "Synthesis of 4-aryl-, 2, 4-diaryl-and 2, 4, 7-triarylpyrrolo [2, 3-d] pyrimidines by a combination of the Suzuki cross-coupling and N-arylation reactions," Tetrahedron, 2012, 68(1):329-339.
Dorai, "Aglycosylated chimeric mouse/human IgG1 antibody retains some effector function," Hybridoma., Apr. 1991, 10(2):211-217.

(56) References Cited

OTHER PUBLICATIONS

Dufies et al., "Mechanisms of AXL overexpression and function in Imatinib-resistant chronic myeloid leukemia cells," Oncotarget, Nov. 2011, 2(11):874-885.
Ecuador Opposition in Ecuador Application No. SENADI-2020-21655, dated May 5, 2021, 27 pages.
Eurasian Office Action in Eurasian Application No. 201892188, dated Oct. 21, 2019, 6 pages.
Eurasian Office Action in Eurasian Application No. 202190153, dated Jul. 14, 2022, 8 pages.
European Extended Search Report in European Application No. 21196789.8, dated Feb. 15, 2022, 7 pages.
European Office Action in European Application No. 17715620.5 dated Sep. 24, 2020, 4 pages.
Feneyrolles et al., "Axl kinase as a key target for oncology: focus on small molecule inhibitors," Mol Cancer Therapy, Sep. 2014, 13(9): 2141-8.
Freshney et al., "Culture of Animal Cells," A Manual of Basic Technique, Alan R. Liss, Inc., 1983, New York, p. 4.
Friend, "Phase I study of an engineered aglycosylated humanized CD3 antibody in renal transplant rejection," Transplantation, 1999, 68:1632-1637.
Gao et al., "High-throughput screening using patient-derived tumor xenografts to predict clinical trial drug response," Nat Med., 2015, 21:1318-1325.
Genbank Accession No. NP_005009 "programmed cell death protein 1 precursor [*Homo sapiens*]," Aug. 2, 2021, 4 pages.
Ghosh, "Synthesis of 4-oxazolinephenylboronic acid and heterobiaryl oxazolines via a Suzuki reaction," Journal of Chemical Research, Apr. 2009, 4:205-207.
Gibson et al., "Pharmaceutical Preformulation and Formulation," CRC Press LLC: Boca Raton, Fla., 2009, 2nd Edition, 559 pages.
Golub et al., "Molecular Classification of Cancer: Class Discovery and Class Prediction by Gene Expression Monitoring," Science, 1999, 286: 531-537.
Gould, "Salt Selection for Basic Drugs," Int J Therapeutics, 1986, 33:201-217.
Graddis et al., "Designing proteins that work using recombinant technologies," Curr Pharm Biotechnol., 2002, 3:285-297.
Graham et al., "Cloning and developmental expression analysis of the murine c-mer tyrosine kinase," Oncogene, Jun. 1995, 10(12): 2349-59.
Graham et al., "Ectopic expression of the proto-oncogene Mer in pediatric T-cell acute lymphoblastic leukemia," Clinical Cancer Research, May 1, 2006 12(9):2662-2669.
Graham et al., "The TAM family: phosphatidylserine sensing receptor tyrosine kinases gone awry in cancer," Nat. Rev. Cancer, Dec. 2014, 14(12): 769-85.
Guo et al., "Axl inhibition induces the antitumor immune response which can be further potentiated by PD-1 blockade in the mouse cancer models", Oncotarget, Oct. 27, 2017, 8(52):89761-89774.
Gustafsson et al., "Differential expression of Axl and Gas6 in renal cell carinoma reflecting tumor advancement and survival," Clin. Cancer Res., 2009, 15: 4742-4749.
Hand et al., "Comparative biological properties of a recombinant chimeric anti-carcinoma mAb and a recombinant aglycosylated variant," Cancer Immunol Immunother., 1992, 35(3):165-174.
Harmsen et al., "Properties, production, and applications of camelid single-domain antibody fragments," Appl Microbiol Biotechnol., 2007, 77(1):13-22.
Hobbs et al., "Interaction of aglycosyl immunoglobulins with the IgG Fc transport receptor from neonatal rat gut: comparison of deglycosylation by tunicamycin treatment and genetic engineering," Mol Immunol., 1992, 29:949-956.
Holland et al., "R428, a Selective Small Molecule Inhibitor of Axl Kinase, Blocks Tumor Spread and Prolongs Survival in Models of Metastatic Breast Cancer," Cancer Research, Feb. 2010, 70(4): 1544-1554.
Holliger et al., "'Diabodies': small bivalent and bispecific antibody fragments," Proc Natl Acad Sci USA., 1993, 90:6444-6448.

Hsieh et al., "The AXL receptor tyrosine kinase is associated with adverse prognosis and distant metastasis in esophageal squamous cell carcinoma," Oncotarget, Jun. 14, 2016, 7(24):36956-36970.
Huang et al., "Structural insights into the inhibited states of the Mer receptor tyrosine kinase," Journal of Structural Biology, 2009, 165: 88-96.
Hudson, et al., "High avidity scFv multimers; diabodies and triabodies," J Immunol Methods., 1999, 231:177-189.
Huston et al., "Protein engineering of antibody binding sites: recovery of specific activity in an anti-digoxin single-chain Fv analogue produced in *Escherichia coli*," Proc Natl Acad Sci USA., 1988, 85:5879-5883.
Hutterer et al., "Axl and growth arrest-specific gene 6 are frequently overexpressed in human gliomas and predict poor prognosis in patients with glioblastoma multiforme," Clinical Cancer Research, Jan. 1, 2008, 14(1):130-138.
Indian Office Action in Indian Application No. 201817040446, dated Aug. 18, 2021, 7 pages.
Indian Office Action in Indian Application No. 202017016215, dated Oct. 4, 2021, 7 pages.
Indian Office Action in Indian Application No. 202117003850, dated Jun. 20, 2022, 5 pages.
Indonesian Office Action in Indonesian Application No. P00202002890, dated Dec. 2, 2021, 10 pages.
International Preliminary Report on Patentability in International Application No. PCT/US2016/048716, dated Nov. 2, 2016, 12 pages.
International Preliminary Report on Patentability in International Application No. PCT/US2017/024270, dated Oct. 2, 2018, 10 pages.
International Preliminary Report on Patentability in International Application No. PCT/US2018/052925, dated Mar. 31, 2020, 8 pages.
International Preliminary Report on Patentability in International Application No. PCT/US2019/039825, dated Jan. 7, 2021, 8 pages.
International Preliminary Report on Patentability in International Application No. PCT/US2021/021053, dated Sep. 15, 2022, 8 pages.
International Search Report and Written Opinion in International Application No. PCT/US2016/031625, dated Jul. 7, 2016, 11 pages.
International Search Report and Written Opinion in International Application No. PCT/US2016/046574, dated Oct. 21, 2016, 14 pages.
International Search Report and Written Opinion in International Application No. PCT/US2016/048716, dated Nov. 2, 2016, 12 pages.
International Search Report and Written Opinion in International Application No. PCT/US2017/024270, dated Jun. 14, 2017, 18 pages.
International Search Report and Written Opinion in International Application No. PCT/US2018/052925, dated Nov. 5, 2018, 14 pages.
International Search Report and Written Opinion in International Application No. PCT/US2019/039825, dated Nov. 11, 2019, 14 pages.
International Search Report in Written Opinion in International Application No. PT/US2021/021053, dated Jun. 16, 2021, 16 pages.
Isaacs et al., "Therapy with monoclonal antibodies. An in vivo model for the assessment of therapeutic potential," J Immunol., May 1992, 148(10):3062-3071.
Israeli Office Action in Israeli Application No. 261,957, dated Oct. 28, 2020, 10 pages.
Israeli Office Action in Israeli Application No. 273579, dated Apr. 25, 2022, 4 pages.
Izumchenko et al. "Patient-derived xenografts effectively capture responses to oncology therapy in a heterogeneous cohort of patients with solid tumors," Ann Oncol., 2017, 28:2595-605.
Japanese Office Action in Japanese Application No. 2018-550711, dated Mar. 9, 2021, 5 pages.
Jin et al., "Patient-derived human tumour tissue xenografts in immunodeficient mice: a systematic review," Clin Transl Oncol., Jul. 2010, 12:473-480.

(56) References Cited

OTHER PUBLICATIONS

Johnson et al., "Relationships between drug activity in NCI preclinical in vitro and in vivo models and early clinical trials," British J. of Cancer., May 18, 2001, 84(10):1424-1431.
Kaufman and Sharp, "Amplification and expression of sequences cotransfected with a modular dihydrofolate reductase complementary dna gene," Mol Biol., 1982, 159:601-621.
Keegan et al., "Preclinical Evaluation of AMG 925, a FLT3/CDK4 Kinase Inhibitor for Treating Acute Myeloid Leukemia," Molecular Cancer Therapeutics, Apr. 2014, 13(4): 880-889.
Kerekes et al., "Aurora kinase inhibitors based on the imidazo[1,2-a]pyrazine core: fluorine and deuterium incorporation improve oral absorption and exposure," J. Med. Chem., 2011, 54: 201-210.
Klimke and Ludemann, "Further evidence for a S-syn correlation in the purine (ß) ribosides: the solution conformation of two tricyclic analogs of adenosine and guanosine," Journal of Biosciences, 1979, 34C(9-10): 653-7.
Koorstra et al., "The Axl receptor tyrosine kinase confers an adverse prognostic influence in pancreatic cancer and represents a new threapeutic target," Cancer Biol. Ther., Apr. 2009, 8(7): 618-626.
Korean Office Action in Korean Application No. 10-2018-7031294, dated Oct. 27, 2021, 16 pages.
Lai and Lemke, "An extended family of protein-tyrosine kinase genes differentially expressed in the vertebrate nervous system," Neuron, May 1991, 6(5): 691-704.
Lamoyi, E., "Preparation of F(ab')2 fragments from mouse IgG of various subclasses," Methods in Enzymology, 1989, 121:652-663.
Leatherbarrow and Dwek, "The effect of aglycosylation on the binding of mouse IgG to staphylococcal protein A," FEBS Letters., 1983, 164(2):227-230.
Leatherbarrow et al., "Effector functions of a monoclonal aglycosylated mouse IgG2a: binding and activation of complement component C1 and interaction with human monocyte Fc receptor," Mol Immunol., 1985, 22(4):407-415.
Lee-Sherick et al., "Aberrant Mer receptor tyrosine kinase expression contributes to leukemogenesis in acute myeloid leukemia," Oncogene, Nov. 2013, 32(46):5359-5368.
Lei et al., "Characterization of the Erwinia carotovora pelB gene and its product pectate lyase," J Bacteriol., 1987, 169(9):4379-4383.
Lemke, "Biology of the TAM Receptors," Cold Spring Harb Perspect Biol., 2013, 5: 1-17.
Lew et al., "Differential TAM receptor-ligand-phospholipid interactions delimit differential TAM bioactivities," Elife, Sep. 2014, 3:e03385.
Li et al., "Axl as a potential therapeutic target in cancer: role of Axl in tumor growth, metastasis and angiogenesis," Oncogene, Oct. 2009, 28(39): 3442-55.
Li et al., "Discovery of AMG 925, a FLT3 and CDK4 Dual Kinase Inhibitor with Preferential Affinity for the Activated State of FLT3," Journal of Medicinal Chemistry, 2014, 57(8): 3430-3449.
Linger et al., "Mer or Axl receptor tyrosine kinase inhibition promotes apoptosis, blocks growth and enhances chemosensitivity of human non-small cell lung cancer," Oncogene, Jul. 2013, 32(29): 3420-3431.
Linger et al., "Taking aim at Mer and Axl receptor tyrosine kinases as novel therapeutic targets in solid tumors," Expert Opin. Ther. Targets, Oct. 2010, 14(10): 1073-1090.
Linger et al., "TAM Receptor Tyrosine Kinases: Biologic Functions, Signaling, and Potential Therapeutic Targeting in Human Cancer," Adv. Cancer Research, 2008, 100: 35-83.
Lippincott Williams & Wilkins, "Remington: The Science and Practice of Pharmacy," 2005, 21st ed., 1 page, Title page.
Liu et al., "Axl Expression Stratifies Patients with Poor Prognosis after Hepatectomy for Hepatocellular Carcinoma," PLOS One, May 16, 2016, 1-13.
Liu et al., "Discovery of Novel Small Molecule Mer Kinase Inhibitors for the Treatment of Pediatric Acute Lymphoblastic Leukemia," Supporting Information, ACS Med. Chem. Lett., 2012, 53 pages.
Liu et al., "Discovery of Small Molecule Mer Kinase Inhibitors for the Treatment of Pediatric Acute Lymphoblastic Leukemia," ACS Med. Chem. Lett., 2012, 3(2): 129-134.
Liu et al., "Induction, regulation, and biologic function of Axl receptor tyrosine kinase in Kaposi sarcoma," Blood, Jul. 15, 2010, 116(2):297-305.
Liu et al., "UNC1062, a new and potent Mer inhibitor," European Journal of Medicinal Chemistry, 2013, 65: 83-93.
Lu and Lemke, "Homeostatic regulation of the immune system by receptor tyrosine kinases of the Tyro 3 family," Science, Jul. 2001, 293(5528): 306-11.
Lu et al, "The Effect of a Point Mutation on the Stability of IgG4 as Monitored by Analytical Ultracentrifugation," J. Pharmaceutical Sciences, 2008, 97:960-969.
Ludwig, et al., "Small-Molecule Inhibition of Axl Targets Tumor Immune Suppression and Enhances Chemotherapy in Pancreatic Cancer," Cancer Research, Jan. 1, 2018, 78(1):246-255.
Mao et al., "Quantitation of poloxamers in pharmaceutical formulations using size exclusion chromatography and colorimetric methods," Journal of Pharmaceutical and Biomedical Analysis, 2004, 35: 1127-1142.
Mexican Office Action in Mexican Application No. MX/a/2018/011792, dated Jul. 11, 2022, 5 pages.
Millstein et al., "Hybrid hybridomas and their use in immunohistochemistry," Nature, 1983, 305:537-539.
Mizushima et al., "pEF-BOS, a powerful mammalian expression vector," Nucleic Acids Res., 1990, 18:5322.
Mollard et al., "Design, Synthesis, and Biological Evaluation of a Series of Novel AXL Kinase Inhibitors," ACS Medicinal Chemistry Letters, 2011, 2: 907-912.
Moller et al., "Intracellular activation of interferon regulatory factor-1 by nanobodies to the multifunctional (Mf1) domain," J Biol Chem., Dec. 2010, 285(49):38348-38361.
Morissette et al., "High-throughput crystallization: polymorphs, salts, co-crystals and solvates of pharmaceutical solids," Advanced Drug Delivery Reviews, 2004, 56:257-300.
Morris et al., "An Integrated Approach to the Selection of Optimal Salt Form for a New Drug Candidate," Int J Pharm., 1994, 105:209-217.
Morrison, "Transfectomas provide novel chimeric antibodies," Science, 1985, 229:1202-1207.
Mudduluru et al., "Myeloid zinc finger 1 induces migration, invasion, and in vivo metastasis through Axl gene expression in solid cancer," Mol. Cancer Res., Feb. 2010, 8(2): 159-169.
Mulligan et al., "Synthesis of rabbit beta-globin in cultured monkey kidney cells following infection with a SV40 beta-globin recombinant genome," Nature, Jan. 1979, 277(5692):108-114.
Myers et al., "AXL inhibitors in cancer: A medicinal chemistry perspective," Journal of Medicinal Chemistry, 2015, pp. 1-53.
Myers et al., "Targeting Tyro3, Axl and MerTK (TAM receptors): implications for macrophages in the tumor microenvironment," Molecular Cancer, 2019, 18:94.
Neau "Pharmaceutical Salts," Water-Insoluble Drug Formulation, 2008, 417-435.
Nishimura et al., "Autoimmune dilated cardiomyopathy in PD-1 receptor-deficient mice," Science, 2001, 291(5502): 319-22.
Nose and Wigzell, "Biological significance of carbohydrate chains on monoclonal antibodies," 1983, Proc Natl Acad Sci USA., Nov. 1983, 80(21):6632-6636.
O'Bryan et al., "axl, a transforming gene isolated from primary human myeloid leukemia cells, encodes a novel receptor tyrosine kinase," Mol. Cell Biol., Oct. 1991, 11(10): 5016-31.
Oi et al., "Chimeric antibodies," BioTechniques, 1986, 4:214-221.
Okamoto et al., "Oligonucleotides containing 7-vinyl-7-deazaguanine as a facile strategy for expanding the functional diversity of DNA," Bioorganic & Medicinal Chemistry Letters, 2002, 12(15): 1895-1896.
Paolino et al., "The E3 ligase Cbl-b and TAM receptors regulate cancer metastasis via natural killer cells," Nature, 2014, 19 pages.
Pardoll, "The blockade of immune checkpoints in cancer immunotherapy," Nat. Rev. Cancer, Mar. 2012, 12(4): 252-64.
Philippine Office Action in Philippine Application No. 1/2018/502102, dated Jun. 23, 2022, 4 pages.

(56) References Cited

OTHER PUBLICATIONS

Philippine Office Action in Philippine Application No. 1/2018/502102, dated Sep. 14, 2021, 5 pages.
Philips et al., "Therapeutic uses of anti-PD-1 and anti-PD-L1 antibodies," International Immunology, Oct. 2014, 27(1):39-46.
Pluckthun, "Antibodies from *Escherichia coli*," The Pharmacology of Monoclonal Antibodies, 1994, 113:269-315.
Plueckthun and Skerra, "Expression of functional antibody Fv and Fab fragments in *Escherichia coli*," Methods in Enzymology, 1989, 178:497-515.
Powell et al., "Highly selective 2,4-diaminopyrimidine-5-carboxamide inhibitors of Sky kinase," Bioorganic & Medicinal Chemistry Letters, 2013, 23: 1046-1050.
Powell et al., "Novel and selective spiroindoline-based inhibitors of sky kinase," Bioorganic & Medicinal Chemistry Letters, 2012, 22: 190-193.
Powers et al., "Expression of single-chain Fv-Fc fusions in Pichia pastoris," J Immunol Methods., 2001, 251:123-135.
Raju, "Glycosylation Variations with Expression Systems and Their Impact on Biological Activity of Therapeutic Immunoglobulins," BioProcess International, Apr. 2003, 44-53.
Rankin et al., "AXL is an essential factor and therapeutic target for metastatic ovarian cancer," Cancer Research, Oct. 1, 2010, 70(19), 7570-7579.
Rao et al., "Preliminary results of a Phase 2 study of INCMGA00012 in patients with squamous carcinoma of the anal canal (SCAC) who have progressed following platinum-based chemotherapy (NCT03597295)," J Immunother of Cancer., 2019, 7(Supplement 1):P826.
Remington's Pharmaceutical Sciences, 17th ed., Mack Publishing Company, Easton, Pa., 1985, p. 1418.
Rho et al., "MET and AXL Inhibitor NPS-1034 Exerts Efficacy against Lung Cancer Cells Resistant to EGFR Kinase Inhibitors Because of MET or AXL Activation," AARC Journals, 2013, 253-262.
Rios-Doria et al., "A Potent and Selective Dual Inhibitor of AXL and MERTK Possesses Both Immunomodulatory and Tumor-Targeted Activity", Front in Oncol., Dec. 7, 2020, 10:598477.
Rousseaux, J. et al., "Optimal conditions for the preparation of proteolytic fragments from monoclonal IgG of different rat IgG subclasses," Methods in Enzymology, 1989, 121:663-669.
Rowe et al., "Handbook of Pharmaceutical Excipients," The Pharmaceutical Press and the American Pharmaceutical Association, 2009, 6th edition, 917 pages.
Sausville et al., "Contributions of human tumor xenografts to anticancer drug development," Cancer Research, Apr. 1, 2006, 66(7):3351-3354.
Schlegel et al., "MERTK receptor tyrosine kinase is a therapeutic target in melanoma," The Journal of Clinical Investigation, May 2013, 123(5): 2257-2267.
Schroeder et al., "Discovery of N-(4-(2-Amino-3-chloropyridin-4-yloxy)-3-fluorophenyl)-4-ethoxy-1-(4-fluorophenyl)-2-oxo-1,2-dihydropyridine-3-carboxamide (BMS-777607), a Selective and Orally Efficacious Inhibitor of the Met Kinase Superfamily," J. Med. Chem., 2009, 52: 1251-1254.
Shibata et al., "Axl receptor blockade ameliorates pulmonary pathology resulting from primary viral infection and viral exacerbation of asthma," The Journal of Immunology, 2014, 192: 3569-3581.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem., 2001, 276(9):6591-6604.
Shields et al., "Lack of fucose on human IgG1 N-linked oligosaccharide improves binding to human Fcgamma RIII and antibody-dependent cellular toxicity," J Biol Chem., 2002, 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem., 2003, 278(5):3466-3473.
Singer et al., "Photochromism of Diarylethene-Functionalized 7-Deazaguanosines," European Journal of Organic Chemistry, 2013, 14: 2766-2769.
Skardziute, "Optical study of the formation of pyrrolo[2,3-d]pyrimidine-based fluorescent nanoaggregates," Tetrahedron, 2013, 69(46):9566-9572.
Storey et al., "Solid State Characterization of Pharmaceuticals," 2011, 170 pages.
Strassmaier and Karpen, "Novel N7- and N1-Substituted cGMP Derivatives Are Potent Activators of Cyclic Nucleotide-Gated Channels," Journal of Medicinal Chemistry, Aug. 2007, 50: 4186-4194.
Suarez et al., "Inhibitors of the TAM subfamily of tyrosine kinsases: Synthesis and biological evaluation," European Journal of Medicinal Chemistry, 2013, 61: 2-25.
Swarbrick et al., "Salt Forms of Drugs and Absorption," Encyclopedia of Pharmaceutical Technology, 1996, 13:453-499.
Tai et al., "Axl promotes cell invasion by inducing MMP-9 activity through activation of NF-kappaB and Brg-1," Oncogene, Jul. 2008, 27(29): 4044-55.
Tao et al., "Studies of aglycosylated chimeric mouse-human IgG. Role of carbohydrate in the structure and effector functions mediated by the human IgG constant region," J Immunol., Oct. 15, 1989, 143(8):2595-2601 (Abstract Only).
Tempest et al., "Reshaping a human monoclonal antibody to inhibit human respiratory syncytial virus infection in vivo," Biotechnology, 1991, 9:266-271.
Tomlinson et al., "The repertoire of human germline VH sequences reveals about fifty groups of VH segments with different hypervariable loops" J Mol Biol., 1992, 227(3):776-798.
Tomlinson et al., "The structural repertoire of the human V kappa domain," EMBO J., 1995, 14:4628-4638.
Traore et al., "New aminopyrimidine derivatives as inhibitors of the TAM family," European Journal of Medicinal Chemistry, 2013, 70: 789-801.
Tumkevicius, "Pyrrolo [2, 3-d] pyrimidine-Core-Extended x-Systems: Synthesisof 2, 4, 7-Triarylpyrrolo [2, 3-d] pyrimidines," Synlett, 2011, 12:1705-1708.
Tumkevicius, "Synthesis and photophysical properties of oligoarylenes with a pyrrolo [2, 3-d] pyrimidine core," Tetrahedron Letters (2010), 51(30), 3902-3906.
Ukraine Office Action in Ukraine Application No. a201810566, dated Dec. 15, 2020, 8 pages.
Ukraine Office Action in Ukraine Application No. a202002558, dated Feb. 18, 2022, 8 pages.
Umana et al., "Engineered glycoforms of an antineuroblastoma IgG1 with optimized antibody-dependent cellular cytotoxic activity," Nat Biotechnol., Feb. 1999, 17(2):176-180.
Urbonas et al., "A Novel Highly Site-Selective Synthesis of 2,4,7-Triarylpyrrolo[2,3-d]pyrimidines by a Combination of Palladium(0)-, Nickel(0)-, and Copper(I)-Catalyzed Cross-Coupling Reactions," Synlett, 2013, 24(11):1383-1386.
Urlaub and Chasin, "Isolation of Chinese hamster cell mutants deficient in dihydrofolate reductase activity," Proc Natl Acad Sci USA., 1980, 77:4216-4220.
Waizeneggar et al., "Role of Growth arrest-specific gene 6-Mer axis in multiple myeloma," Leukemia, 2015, 29: 696-704.
Walker et al., "Aglycosylation of human IgG1 and IgG3 monoclonal antibodies can eliminate recognition by human cells expressing Fc gamma RI and/or Fc gamma RII receptors," Biochem J., 1989, 259:347-353.
Wang et al., "Mer receptor tyrosine kinase promotes invasion and survival in glioblastoma multiforme," Oncogene, Feb. 2013, 32(7): 872-882.
Ward and Ghetie, "The effector functions of immunoglobulins: implications for therapy," Therapeutic Immunology, 1995, 2:77-94.
Ward et al., "Binding activities of a repertoire of single immunoglobulin variable domains secreted from *Escherichia coli*," Nature, Oct. 12, 1989, 341(6242):544-546.
Wright & Morrison, "Effect of glycosylation on antibody function: implications for genetic engineering," Tibtech., 1997, 15(1):26-32.

(56) References Cited

OTHER PUBLICATIONS

Wu et al., "Multisubstituted quinoxalines and pyrido[2,3-d]pyrimidines: Synthesis and SAR study as tyrosine kinase c-Met inhibitors," Bioorganic & Medicinal Chemistry Letters, 2012, 22: 6368-6372.
Xu et al., "Design, synthesis and biological evaluation of deuterated nintedanib for improving pharmacokinetic properties," J. Label Compd. Radiopharm., 2015, 58: 308-312.
Yamazoe et al., "Mechanism of formation and structural characterization of DNA adducts derived from peroxidative activation of benzidine," Carcinogenesis, Sep. 1988, 9(9): 1635-41.
Zhang et al., "Activation of the AXL kinase causes resistance to EGFR-targeted therapy in lung cancer," Nat. Genet., 2012, 44(8): 852-860.
Zhang et al., "Discovery of Mer Specific Tyrosine Kinase Inhibitors for the Treatment and Prevention of Thrombosis," Journal of Medicinal Chemistry, 2013, 56: 9693-9700.
Zhang et al., "Discovery of novel type II c-Met inhibitors based on BMS-777607," European Journal of Medicinal Chemistry, 2014, 80: 254-266.
Zhang et al., "Knockdown of AXL receptor tyrosine kinase in osteosarcoma cells leads to decreased proliferation and increased apoptosis," Int. J. Immunopathol. Pharmacol., Jan.-Mar. 2013, 26(1):179-188.
Zhang et al., "Pseudo-Cyclization through Intramolecular Hydrogen Bond Enables Discovery of Pyridine Substituted Pyrimidines as New Mer Kinase Inhibitors," Journal of Medicinal Chemistry, 2013, 56: 6983-9692.
Zhang et al., "UNC20205, a Potent and Orally Bioavailable MER/FLT3 Dual Inhibitor," Journal of Medicinal Chemistry, 2014, 57: 7031-7041.
Zhao, et al., "Discovery of novel Bruton's tyrosine kinase (BTK) inhibitors bearing a pyrrolo [2, 3-d] pyrimidine scaffold," Bioorganic & Medicinal Chemistry, Feb. 2015, 23(4):891-901.
Zhou et al., "Synthesis and evaluation of Janus type nucleosides as potential HCV NS5B polymerase inhibitors," Bioorganic & Medicinal Chemistry Letters, Jun. 2013, 23: 3385-3388.
Argentinian Office Action in Argentinian Application No. 20180102760, dated Nov. 17, 2023, 8 pages (with Machine Translation).
Australian Office Action in Australian Application No. 2023270198, dated Nov. 23, 2023, 2 pages.
Brazilian Office Action in Brazilian Application No. 112018069612-9, dated Sep. 5, 2023, 8 pages (with Machine Translation).
Canadian Office Action in Canadian Application No. 3019145, dated Oct. 26, 2023, 3 pages.
Cancer Drug Design and Discovery, 1st ed., Neidle (ed)., 2008, p. 427.
Chilean Office Action in Chilean Application No. 202201014, dated Sep. 5, 2023, 36 pages (with Machine Translation).
Chinese Office Action in Chinese Application No. 202111577669.3, dated Aug. 25, 2023, 10 pages (with English Translation).
Colombian Office Action in Colombian Application No. 2021/0000923, dated Apr. 26, 2023, 22 pages (with English translation).
Columbian Office Action in Columbian Application No. 2021/0000923, dated Sep. 24, 2023, 25 pages (with English Translation).
Columbian Office Action in Columbian Application No. NC2020/0005009, dated Oct. 25, 2023, 27 pages (with English Translation).
Design of Organic Solids: Topics in Current Chemistry, 1st ed., Weber (ed)., 1998, Chapter: Crystalline Polymorphism of Organic Compounds, 46 pages.
Encyclopedia of Biomedical Polymers and Polymeric Biomaterials, 1st ed., Mishra (ed)., Jan. 31, 2016, Chapter: Chitosan and Pluronic® F-127: Pharmaceutical Applications, 24 pages.
European Communication pursuant to Article 94(3) EPC in European Application No. 21196789.8, dated Mar. 2, 2023, 4 pages.
Indian Office Action in Indian Application No. 202017016215, dated Dec. 1, 2023, 3 pages.
Indian Office Action in Indian Application No. 202017016215, dated Oct. 11, 2023, 3 pages.
Indian Office Action in Indian Application No. 202117003850, dated Nov. 1, 2023, 3 pages.
Indian Oral Hearing Notice in Indian Application No. 202117003850, dated Jul. 5, 2023, 3 pages.
Indian Oral Hearing Notice in Indian Application No. 202117003850, dated Sep. 5, 2023, 3 pages.
Israel Office Action in Israeli Application No. 279,735, dated Jul. 11, 2023, 5 pages.
Israeli Office Action in Israeli Application No. 273,579, dated Sep. 18, 2023, 4 pages.
Japanese Office Action in Japanese Application No. 2020-573235, dated Jun. 6, 2023, 8 pages (with Machine Translation).
Kasikara, "Pan-TAM tyrosine kinase inhibitor BMS-777607 enhances anti-PD-1 mAb efficacy in a murine model of triple negative breast cancer," Cancer Research, 2019, 79(10):2669-2683.
Korean Office Action in Korean Application No. 10-2023-7024326, dated Nov. 28, 2023, 7 pages (with English Translation).
Li et al., "AXL targeting restores PD-1 blockade sensitivity of STK11/LKB1 mutant NSCLC through expansion of TCF1+ CD8 T cells," Cell Reports Medicine, 2022, 3(3):1-13.
McMahon et al., "VEGF Receptor Signaling in Tumor Angiogenesis," The Oncologist, Feb. 14, 2000, 5(suppl 1):3-10.
Patani et al., "Bioisosterism: A Rational Approach in Drug Design," Chemical Reviews, 1996, 96(8):3147-3176.
Peeters et al., "TAM-ing T cells in the tumor microenvironment—implications for TAM receptor targeting," Cancer Immunology Immunotherapy, 2019, 69:237-244.
Pinedo et al., "Translational Research: The Role of VEGF in Tumor Angiogenesis," The Oncologist, Feb. 22, 2000, 5(Suppl. 1):1-2.
Taiwanese Office Action in Taiwanese Application No. 108122789, dated Mar. 9, 2023, 8 pages (with English translation).
Yokoyama et al., "Immuno-Oncological Efficacy of RXDX-106, a Novel Small Molecule Inhibitor of TAM (TYRO3, AXL, MER) family of kinases," 2019, 79(8):1996-2008.
Argentinian Office Action in Argentinian Application No. 20170100750, dated Jul. 12, 2024, 9 pages (with English Translation).
Australian Office Action in Australian Application No. 2019293618, dated Apr. 12, 2024, 4 pages.
Chilean Office Action in Chilean Application No. 202201014, dated Jun. 11, 2024, 33 pages (with Machine Translation).
Chilean Office Action in Chilean Application No. 202202410, dated Jan. 5, 2024, 31 pages (with Machine Translation).
Chinese Office Action in Chinese Application No. 2021800309009, dated Jul. 2, 2024, 14 pages (with English Translation).
Eurasian Office Action in Eurasian Application No. 202292545, dated Jan. 31, 2024, 6 pages (with English Translation).
European Search Report in European Application No. 23202364.8, dated Apr. 9, 2024, 13 pages.
Malaysian Office Action in Malaysian Application No. PI2020007048, dated May 31, 2024, 6 pages.
Peruvian Office Action in Peruvian Application No. 2199-2020, dated Jan. 12, 2024, 15 pages (with English Translation).
Philippines Office Action in Philippines Application No. 1-2020-550143, dated Apr. 22, 2024, 4 pages.
Schlothauer et al., "Novel human IgG1 and IgG4 Fc-engineered antibodies with completely abolished immune effector functions," Protein Engineering, Design and Selection, Oct. 2016, 29(10):457-466.
Ukrainian Office Action in Ukrainian Application No. a202100313, dated Feb. 8, 2024, 8 pages (with English Translation).

\* cited by examiner

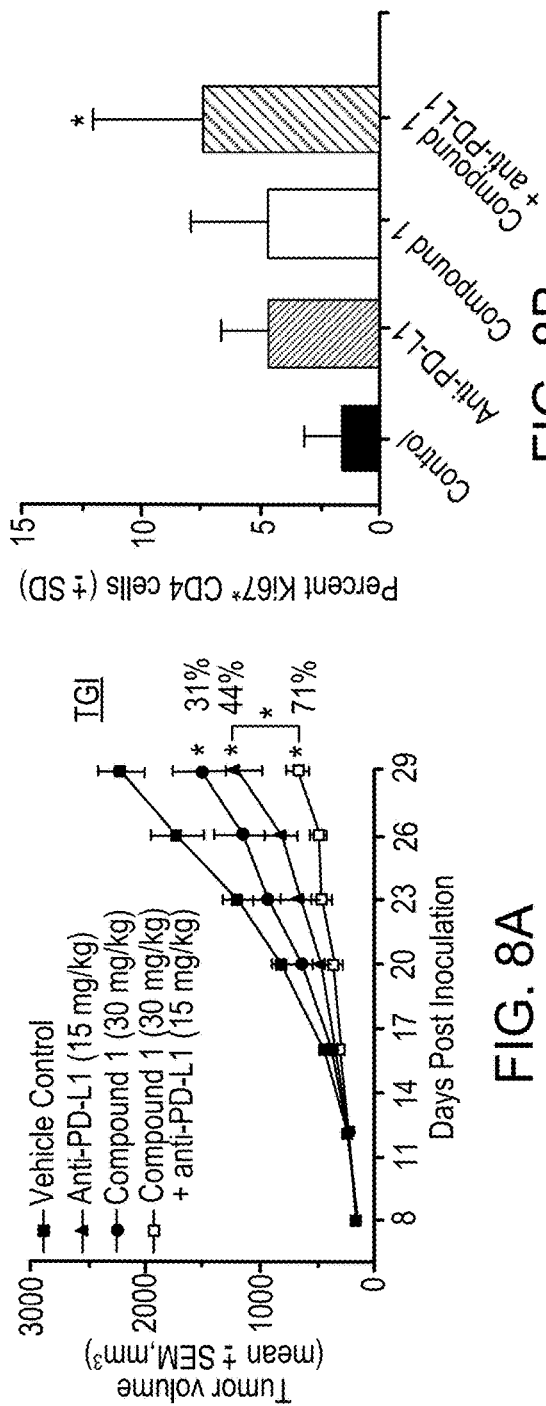
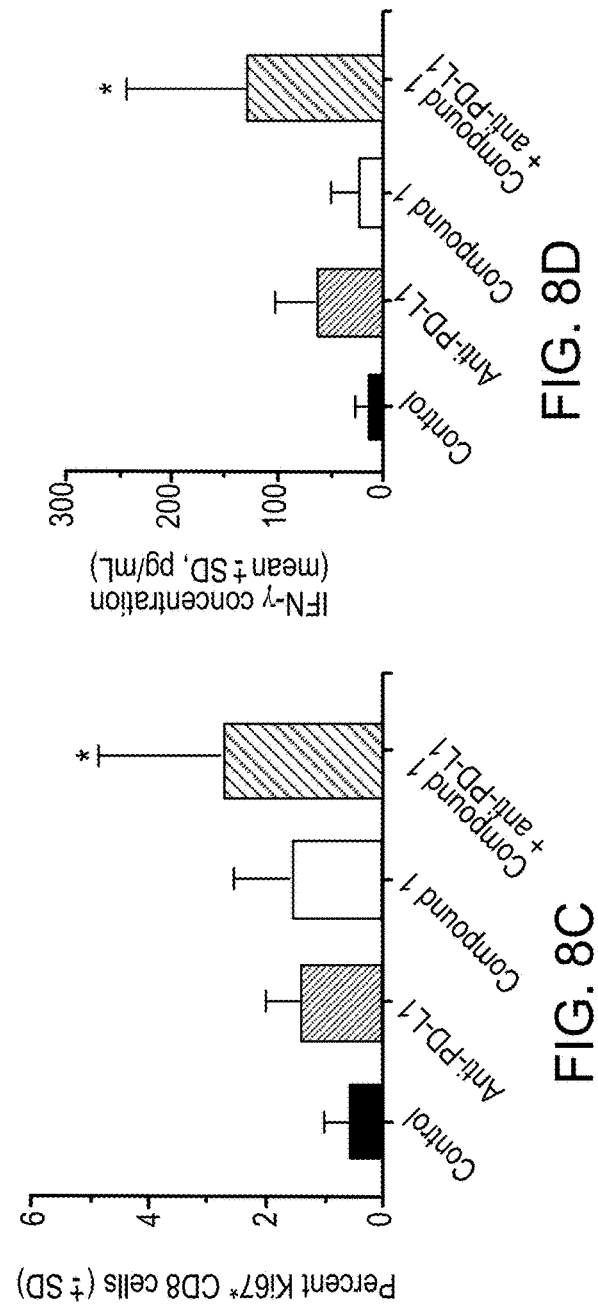
FIG. 8A
FIG. 8B
FIG. 8C
FIG. 8D

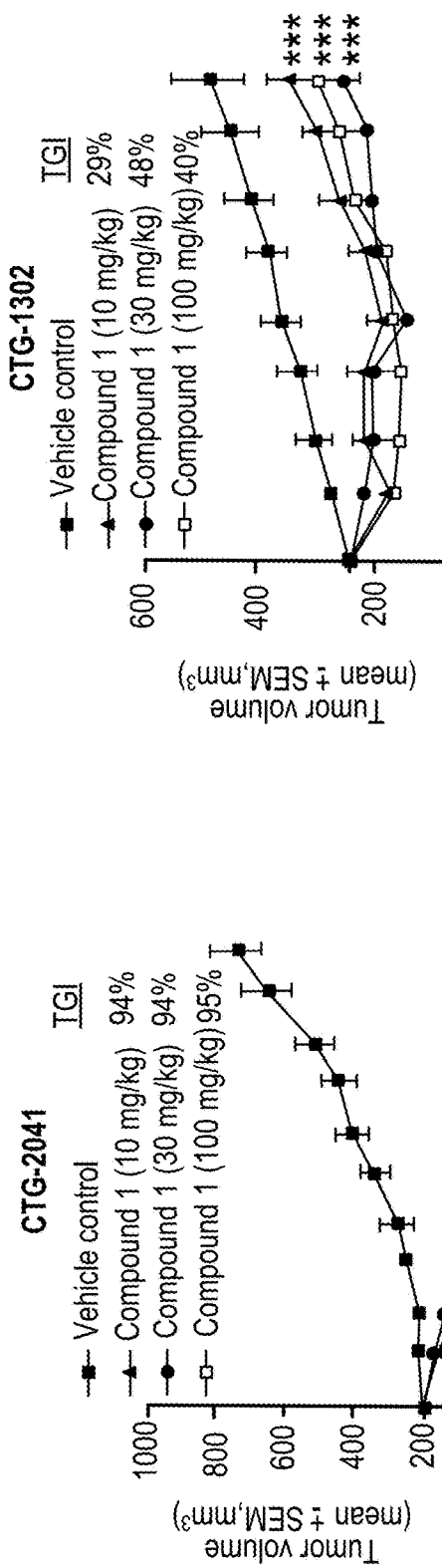
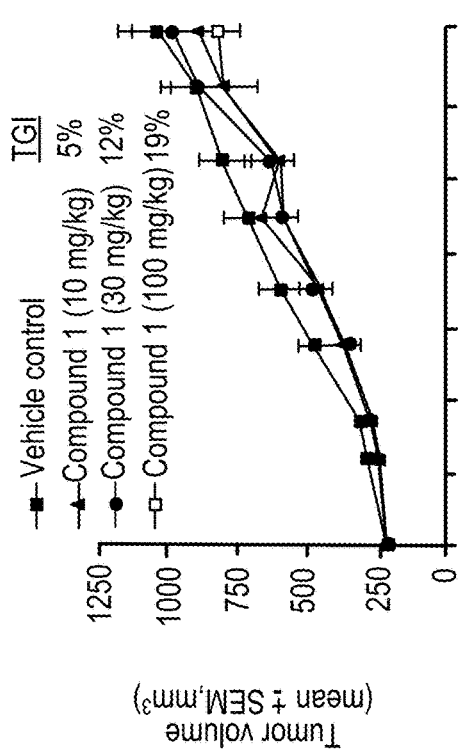
FIG. 9A
FIG. 9B
FIG. 9C

SEQUENCE LISTING

```
<160> NUMBER OF SEQ ID NOS: 13

<210> SEQ ID NO 1
<211> LENGTH: 288
<212> TYPE: PRT
<213> ORGANISM: Artificial Sequence
<220> FEATURE:
<223> OTHER INFORMATION: humanized, IgG4 monoclonal antibody
<220> FEATURE:
<221> NAME/KEY: MISC_FEATURE
<222> LOCATION: (1)..(288)
<223> OTHER INFORMATION: Human PD-1 Polypeptide (NCI Sequence NP
      005009.2)
<220> FEATURE:
<221> NAME/KEY: MISC_FEATURE
<222> LOCATION: (1)..(20)
<223> OTHER INFORMATION: Human PD-1 Signal Sequence

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
```

```
                100             105                110
Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135             140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 2
<211> LENGTH: 445
<212> TYPE: PRT
<213> ORGANISM: Artificial Sequence
<220> FEATURE:
<223> OTHER INFORMATION: humanized, IgG4 monoclonal antibody
<220> FEATURE:
<221> NAME/KEY: MISC_FEATURE
<222> LOCATION: (1)..(445)
<223> OTHER INFORMATION: Human PD-1 Polypeptide (NCI Sequence NP
      005009.2)
<220> FEATURE:
<221> NAME/KEY: MISC_FEATURE
<222> LOCATION: (1)..(20)
<223> OTHER INFORMATION: Human PD-1 Signal Sequence

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met Asn Trp Val Arg Gln Ala Pro Gly Gln Gly Leu Glu Trp Ile
            35                  40                  45

Gly Val Ile His Pro Ser Asp Ser Glu Thr Trp Leu Asp Gln Lys Phe
        50                  55                  60

Lys Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu His Tyr Gly Thr Ser Pro Phe Ala Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
```

```
                130               135               140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Lys Thr Tyr Thr Cys Asn Val Asp His Lys Pro
                195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
                275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly
                435                 440                 445

<210> SEQ ID NO 3
<211> LENGTH: 218
<212> TYPE: PRT
<213> ORGANISM: Artificial Sequence
<220> FEATURE:
<223> OTHER INFORMATION: humanized, IgG4 monoclonal antibody
<220> FEATURE:
<221> NAME/KEY: MISC_FEATURE
<222> LOCATION: (1)..(218)
<223> OTHER INFORMATION: Human PD-1 Polypeptide (NCI Sequence NP
      005009.2)
<220> FEATURE:
<221> NAME/KEY: MISC_FEATURE
<222> LOCATION: (1)..(20)
<223> OTHER INFORMATION: Human PD-1 Signal Sequence

<400> SEQUENCE: 3

Glu Ile Val Leu Thr Gln Ser Pro Ala Thr Leu Ser Leu Ser Pro Gly
```

```
1               5                   10                  15
Glu Arg Ala Thr Leu Ser Cys Arg Ala Ser Glu Ser Val Asp Asn Tyr
            20                  25                  30
Gly Met Ser Phe Met Asn Trp Phe Gln Gln Lys Pro Gly Gln Pro Pro
            35                  40                  45
Lys Leu Leu Ile His Ala Ala Ser Asn Gln Gly Ser Gly Val Pro Ser
50                  55                  60
Arg Phe Ser Gly Ser Gly Ser Gly Thr Asp Phe Thr Leu Thr Ile Ser
65                  70                  75                  80
Ser Leu Glu Pro Glu Asp Phe Ala Val Tyr Phe Cys Gln Gln Ser Lys
            85                  90                  95
Glu Val Pro Tyr Thr Phe Gly Gly Gly Thr Lys Val Glu Ile Lys Arg
            100                 105                 110
Thr Val Ala Ala Pro Ser Val Phe Ile Phe Pro Pro Ser Asp Glu Gln
            115                 120                 125
Leu Lys Ser Gly Thr Ala Ser Val Val Cys Leu Leu Asn Asn Phe Tyr
130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
            165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
            195                 200                 205
Val Thr Lys Ser Phe Asn Arg Gly Glu Cys
210                 215
```

<210> SEQ ID NO 4
<211> LENGTH: 119
<212> TYPE: PRT
<213> ORGANISM: Artificial Sequence
<220> FEATURE:
<223> OTHER INFORMATION: humanized, IgG4 monoclonal antibody
<220> FEATURE:
<221> NAME/KEY: MISC_FEATURE
<222> LOCATION: (1)..(119)
<223> OTHER INFORMATION: Human PD-1 Polypeptide (NCI Sequence NP
      005009.2)
<220> FEATURE:
<221> NAME/KEY: MISC_FEATURE
<222> LOCATION: (1)..(20)
<223> OTHER INFORMATION: Human PD-1 Signal Sequence

<400> SEQUENCE: 4

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ser Phe Thr Ser Tyr
            20                  25                  30
Trp Met Asn Trp Val Arg Gln Ala Pro Gly Gln Gly Leu Glu Trp Ile
            35                  40                  45
Gly Val Ile His Pro Ser Asp Ser Glu Thr Trp Leu Asp Gln Lys Phe
50                  55                  60
Lys Asp Arg Val Thr Ile Thr Val Asp Lys Ser Thr Ser Thr Ala Tyr
65                  70                  75                  80
Met Glu Leu Ser Ser Leu Arg Ser Glu Asp Thr Ala Val Tyr Tyr Cys
            85                  90                  95
Ala Arg Glu His Tyr Gly Thr Ser Pro Phe Ala Tyr Trp Gly Gln Gly
```

-continued

```
                100              105             110
Thr Leu Val Thr Val Ser Ser
        115

<210> SEQ ID NO 5
<211> LENGTH: 111
<212> TYPE: PRT
<213> ORGANISM: Artificial Sequence
<220> FEATURE:
<223> OTHER INFORMATION: humanized, IgG4 monoclonal antibody
<220> FEATURE:
<221> NAME/KEY: MISC_FEATURE
<222> LOCATION: (1)..(111)
<223> OTHER INFORMATION: Human PD-1 Polypeptide (NCI Sequence NP
      005009.2)
<220> FEATURE:
<221> NAME/KEY: MISC_FEATURE
<222> LOCATION: (1)..(20)
<223> OTHER INFORMATION: Human PD-1 Signal Sequence

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys
                100                 105                 110

<210> SEQ ID NO 6
<211> LENGTH: 5
<212> TYPE: PRT
<213> ORGANISM: Artificial Sequence
<220> FEATURE:
<223> OTHER INFORMATION: humanized, IgG4 monoclonal antibody
<220> FEATURE:
<221> NAME/KEY: MISC_FEATURE
<222> LOCATION: (1)..(5)
<223> OTHER INFORMATION: Human PD-1 Polypeptide (NCI Sequence NP
      005009.2)
<220> FEATURE:
<221> NAME/KEY: MISC_FEATURE
<222> LOCATION: (1)..(5)
<223> OTHER INFORMATION: Human PD-1 Signal Sequence

<400> SEQUENCE: 6

Ser Tyr Trp Met Asn
1               5

<210> SEQ ID NO 7
<211> LENGTH: 17
<212> TYPE: PRT
<213> ORGANISM: Artificial Sequence
<220> FEATURE:
<223> OTHER INFORMATION: humanized, IgG4 monoclonal antibody
<220> FEATURE:
<221> NAME/KEY: MISC_FEATURE
<222> LOCATION: (1)..(17)
<223> OTHER INFORMATION: Human PD-1 Polypeptide (NCI Sequence NP
      005009.2)
```

```
<220> FEATURE:
<221> NAME/KEY: MISC_FEATURE
<222> LOCATION: (1)..(17)
<223> OTHER INFORMATION: Human PD-1 Signal Sequence

<400> SEQUENCE: 7

Val Ile His Pro Ser Asp Ser Glu Thr Trp Leu Asp Gln Lys Phe Lys
1               5                   10                  15
Asp

<210> SEQ ID NO 8
<211> LENGTH: 10
<212> TYPE: PRT
<213> ORGANISM: Artificial Sequence
<220> FEATURE:
<223> OTHER INFORMATION: humanized, IgG4 monoclonal antibody
<220> FEATURE:
<221> NAME/KEY: MISC_FEATURE
<222> LOCATION: (1)..(10)
<223> OTHER INFORMATION: Human PD-1 Polypeptide (NCI Sequence NP
      005009.2)
<220> FEATURE:
<221> NAME/KEY: MISC_FEATURE
<222> LOCATION: (1)..(10)
<223> OTHER INFORMATION: Human PD-1 Signal Sequence

<400> SEQUENCE: 8

Glu His Tyr Gly Thr Ser Pro Phe Ala Tyr
1               5                   10

<210> SEQ ID NO 9
<211> LENGTH: 16
<212> TYPE: PRT
<213> ORGANISM: Artificial Sequence
<220> FEATURE:
<223> OTHER INFORMATION: humanized, IgG4 monoclonal antibody
<220> FEATURE:
<221> NAME/KEY: MISC_FEATURE
<222> LOCATION: (1)..(16)
<223> OTHER INFORMATION: Human PD-1 Polypeptide (NCI Sequence NP
      005009.2)
<220> FEATURE:
<221> NAME/KEY: MISC_FEATURE
<222> LOCATION: (1)..(16)
<223> OTHER INFORMATION: Human PD-1 Signal Sequence

<400> SEQUENCE: 9

Arg Ala Ser Glu Ser Val Asp Asn Tyr Gly Met Ser Phe Met Asn Trp
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: humanized, IgG4 monoclonal antibody
<220> FEATURE:
<221> NAME/KEY: MISC_FEATURE
<222> LOCATION: (1)..(7)
<223> OTHER INFORMATION: Human PD-1 Polypeptide (NCI Sequence NP
      005009.2)
<220> FEATURE:
<221> NAME/KEY: MISC_FEATURE
<222> LOCATION: (1)..(7)
<223> OTHER INFORMATION: Human PD-1 Signal Sequence

<400> SEQUENCE: 10

Ala Ala Ser Asn Gln Gly Ser
1               5
```

-continued

```
<210> SEQ ID NO 11
<211> LENGTH: 9
<212> TYPE: PRT
<213> ORGANISM: Artificial Sequence
<220> FEATURE:
<223> OTHER INFORMATION: humanized, IgG4 monoclonal antibody
<220> FEATURE:
<221> NAME/KEY: MISC_FEATURE
<222> LOCATION: (1)..(9)
<223> OTHER INFORMATION: Human PD-1 Polypeptide (NCI Sequence NP
      005009.2)
<220> FEATURE:
<221> NAME/KEY: MISC_FEATURE
<222> LOCATION: (1)..(7)
<223> OTHER INFORMATION: Human PD-1 Signal Sequence

<400> SEQUENCE: 11

Gln Gln Ser Lys Glu Val Pro Tyr Thr
1               5

<210> SEQ ID NO 12
<211> LENGTH: 12
<212> TYPE: PRT
<213> ORGANISM: Artificial Sequence
<220> FEATURE:
<223> OTHER INFORMATION: humanized, IgG4 monoclonal antibody
<220> FEATURE:
<221> NAME/KEY: MISC_FEATURE
<222> LOCATION: (1)..(12)
<223> OTHER INFORMATION: Human PD-1 Polypeptide (NCI Sequence NP
      005009.2)
<220> FEATURE:
<221> NAME/KEY: MISC_FEATURE
<222> LOCATION: (1)..(12)
<223> OTHER INFORMATION: Human PD-1 Signal Sequence

<400> SEQUENCE: 12

Glu Ser Lys Tyr Gly Pro Pro Cys Pro Pro Cys Pro
1               5                   10

<210> SEQ ID NO 13
<211> LENGTH: 448
<212> TYPE: PRT
<213> ORGANISM: Artificial Sequence
<220> FEATURE:
<223> OTHER INFORMATION: humanized, IgG4 monoclonal antibody
<220> FEATURE:
<221> NAME/KEY: MISC_FEATURE
<222> LOCATION: (1)..(448)
<223> OTHER INFORMATION: Human PD-1 Polypeptide (NCI Sequence NP
      005009.2)
<220> FEATURE:
<221> NAME/KEY: MISC_FEATURE
<222> LOCATION: (1)..(20)
<223> OTHER INFORMATION: Human PD-1 Signal Sequence

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Met Asn Trp Val Arg Gln Ala Pro Gly Gln Gly Leu Glu Trp Ile
        35                  40                  45

Gly Val Ile His Pro Ser Asp Ser Glu Thr Trp Leu Asp Gln Lys Phe
    50                  55                  60

Lys Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Glu His Tyr Gly Thr Ser Pro Phe Ala Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

COMBINATION THERAPY COMPRISING AXL/MER AND PD-1/PD-L1 INHIBITORS

FIELD

The present disclosure relates to methods of treating cancer by administering a compound, which is an AXL/MER kinase inhibitor, in combination with an antibody, or an antibody fragment thereof, that binds to PD-1.

BACKGROUND

Receptor tyrosine kinases (RTKs) are cell surface proteins that transmit signals from the extracellular environment to the cell cytoplasm and nucleus to regulate cellular events such as survival, growth, proliferation, differentiation, adhesion and migration.

The TAM subfamily consists of three RTKs including Tyro3, AXL and Mer (Graham et al., 2014, Nature Reviews Cancer 14, 769-785; Linger et al., 2008, Advances in Cancer Research 100, 35-83). TAM kinases are characterized by an extracellular ligand binding domain consisting of two immunoglobulin-like domains and two fibronectin type III domains. Two ligands, growth arrest specific 6 (GAS6) and protein S (PROS1), have been identified for TAM kinases. GAS6 can bind to and activate all three TAM kinases, while PROS1 is a ligand for Mer and Tyro3 (Graham et al., 2014, Nature Reviews Cancer 14, 769-785).

AXL (also known as UFO, ARK, JTK11 and TYRO7) was originally identified as a transforming gene from DNA of patients with chronic myelogenous leukemia (O'Bryan et al., 1991, Mol Cell Biol 11, 5016-5031; Graham et al., 2014, Nature Reviews Cancer 14, 769-785; Linger et al., 2008, Advances in Cancer Research 100, 35-83). GAS6 binds to AXL and induces subsequent auto-phosphorylation and activation of AXL tyrosine kinase. AXL activates several downstream signaling pathways including PI3K-Akt, Raf-MAPK, PLC-PKC (Feneyrolles et al., 2014, Molecular Cancer Therapeutics 13, 2141-2148; Linger et al., 2008, Advances in Cancer Research 100, 35-83).

MER (also known as MERTK, EYK, RYK, RP38, NYK and TYR012) was originally identified as a phospho-protein from a lymphoblastoid expression library (Graham et al., 1995, Oncogene 10, 2349-2359; Graham et al., 2014, Nature Reviews Cancer 14, 769-785; Linger et al., 2008, Advances in Cancer Research 100, 35-83). Both GAS6 and PROS1 can bind to Mer and induce the phosphorylation and activation of Mer kinase (Lew et al., 2014). Like AXL, MER activation also conveys downstream signaling pathways including PI3K-Akt and Raf-MAPK (Linger et al., 2008, Advances in Cancer Research 100, 35-83).

TYRO3 (also known as DTK, SKY, RSE, BRT, TIF, ETK2) was originally identified through a PCR-based cloning study (Lai et al., Neuron 6, 691-70, 1991; Graham et al., 2014, Nature Reviews Cancer 14, 769-785; Linger et al., 2008, Advances in Cancer Research 100, 35-83). Both ligands, GAS6 and PROS1, can bind to and activate TYRO3. Although the signaling pathways downstream of TYRO3 activation are the least studied among TAM RTKs, it appears that both PI3K-Akt and Raf-MAPK pathways are involved (Linger et al., 2008, Advances in Cancer Research 100, 35-83). AXL, MER and TYRO3 are found to be over-expressed in cancer cells.

There remains a need for new treatment regimens for cancer using modulators of AXL/MER kinases in combination with an antibody, or an antibody fragment thereof, that binds to PD-1. The present disclosure is directed toward this need and others.

SUMMARY

The present application provides, inter alia, methods of treating cancer in a patient, comprising administering to said patient:

(i) Compound 1, having the structure:

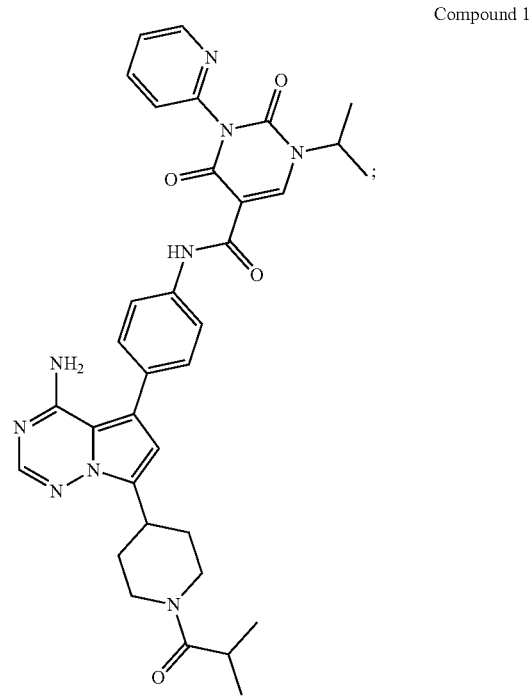 [SMILES: CC(C)C(=O)N1CCC(c2cc(-c3ccc(NC(=O)c4cn(C(C)C)c(=O)n(-c5ccccn5)c4=O)cc3)c3c(N)ncnn23)CC1]

Compound 1 or a pharmaceutically acceptable salt thereof; and (ii) an antibody, or an antigen-binding fragment thereof, that binds to human PD-1, wherein the antibody comprises (ii-1) a variable heavy (VH) domain comprising VH complementarity determining region (CDR)1, VH CDR2, and VH CDR3; and (ii-2) a variable light (VL) domain comprising VL CDR1, VL CDR2, and VL CDR3; wherein:

(a) the VH CDR1 comprises the amino acid sequence SYWMN (SEQ ID NO:6);
(b) the VH CDR2 comprises the amino acid sequence VIHPSDSETWLDQKFKD (SEQ ID NO:7);
(c) the VH CDR3 comprises the amino acid sequence EHYGTSPFAY (SEQ ID NO:8);
(d) the VL CDR1 comprises the amino acid sequence RASESVDNYGMSFMNW (SEQ ID NO:9);
(e) the VL CDR2 comprises the amino acid sequence AASNQGS (SEQ ID NO:10); and
(f) the VL CDR3 comprises the amino acid sequence QQSKEVPYT (SEQ ID NO:11).

The present application further provides methods of treating cancer in a patient, comprising administering to the patient, Compound 1, or a pharmaceutically acceptable salt thereof, and retifanlimab.

The present application also provides use of Compound 1, or a pharmaceutically acceptable salt thereof, and the antibody, or the antigen-binding fragment described herein, for preparation of a medicament for treatment of cancer.

The present application further provides Compound 1, or a pharmaceutically acceptable salt thereof, and the antibody, or the antigen-binding fragment described herein, for use in any of the methods described herein.

DESCRIPTION OF DRAWINGS

FIG. 8A is a plot of the MC38 tumor volume of C57BL/6 mice that were dosed orally with Compound 1, anti-programmed death ligand 1 (PD-L1), or the combination.

FIG. 8B is a graph of the percentage of $CD4^+Ki67^+$ cells in MC38 tumor-bearing mice following treatment with Compound 1, anti-PD-L1 or the combination.

FIG. 8C is a graph of the percentage of $CD8^+Ki67^+$ cells in MC38 tumor-bearing mice following treatment with Compound 1, anti-PD-L1 or the combination.

FIG. 8D is a graph of the concentration of interferon (IFN)-γ in tumor extracts from MC38 tumor-bearing mice following treatment with Compound 1, anti-PD-L1 or the combination.

FIG. 9A is a plot of the tumor volume of CTG-2041 tumors in athymic nude mice following treatment with Compound 1.

FIG. 9B is a plot of the tumor volume of CTG-1302 tumors in athymic nude mice following treatment with Compound 1.

FIG. 9C is a plot of the tumor volume of CTG-1339 tumors in athymic nude mice following treatment with Compound 1.

DETAILED DESCRIPTION

Figure 1:
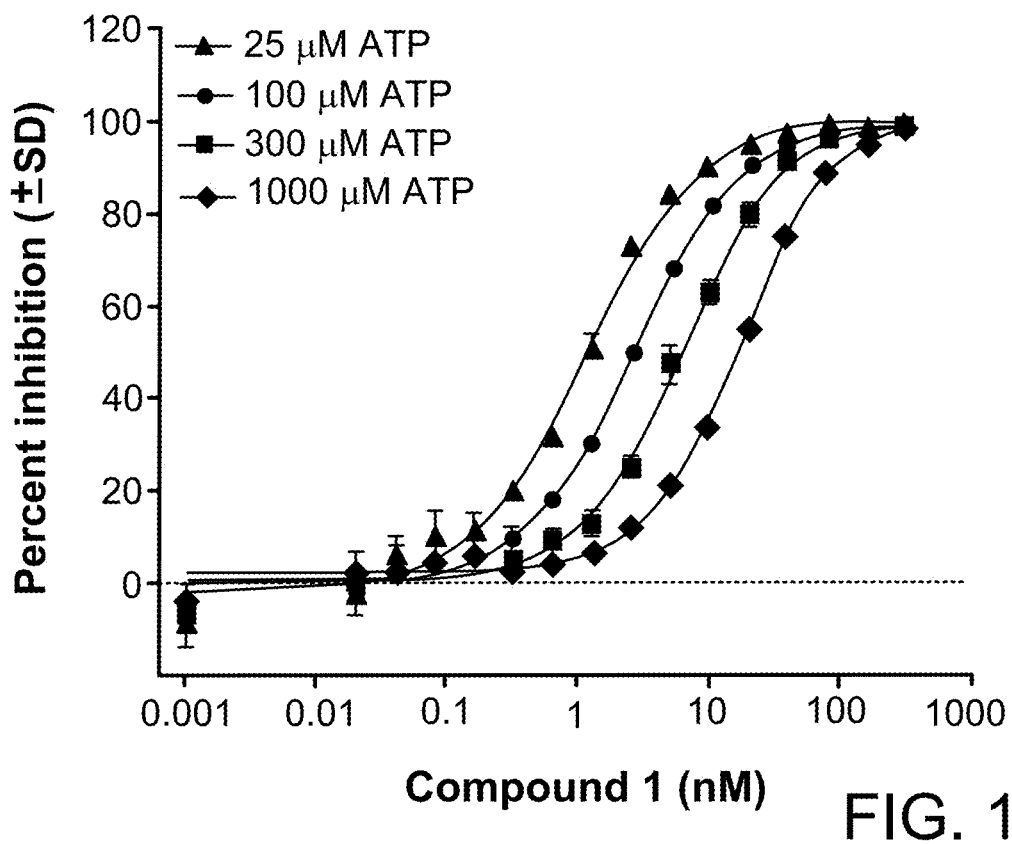
FIG. 1 is a plot of $IC_{50}$ values of Compound 1 for MER kinase versus ATP concentration.

The present application provides, inter alia, a method of treating cancer in a patient, comprising administering to said patient:

(i) Compound 1, having the structure:

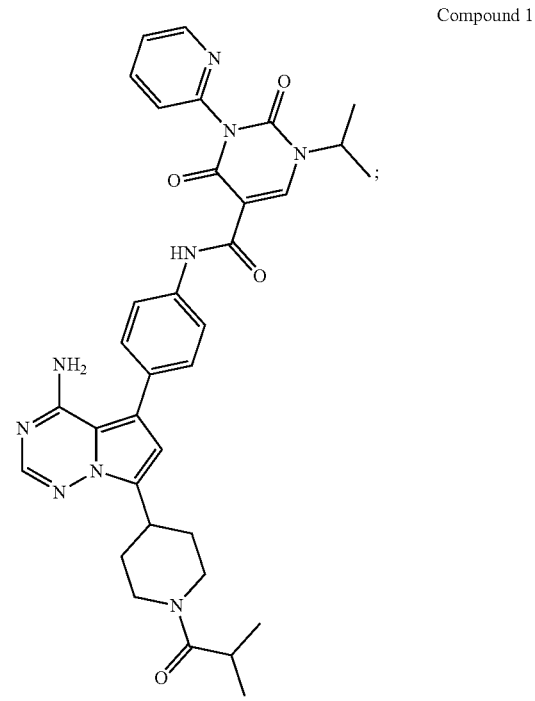 [SMILES: CC(C)C(=O)N1CCC(c2cc(-c3ccc(NC(=O)c4cn(C(C)C)c(=O)n(-c5ccccn5)c4=O)cc3)c3c(N)ncnn23)CC1]

Compound 1 or a pharmaceutically acceptable salt thereof; and (ii) an antibody, or an antigen-binding fragment thereof, that binds to human PD-1 (e.g., retifanlimab).

In vitro studies demonstrated induction of proinflammatory cytokines with single-agent Compound 1 treatment and single agent retifanlimab treatment, however, the combination of Compound 1 with PD-1 antibody retifanlimab resulted in a much greater induction of cytokines (Example G).

The amino acid sequence of the human PD-1 protein (Genbank Accession No. NP_005009) is:

(SEQ ID NO: 1)
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKAQIKESLRAELRVTERRAE

VPTAHPSPSPRPAGQFQTLVVGVVGGLLGSLVLLVWVLAVICSRAARGTI

GARRTGQPLKEDPSAVPVFSVDYGELDFQWREKTPEPPVPCVPEQTEYAT

IVFPSGMGTSSPARRGSADGPRSAQPLRPEDGHCSWPL.

Retifanlimab is a humanized, IgG4 monoclonal antibody that binds to human PD-1 (see US 2019/0127467, which is incorporated herein by reference in its entirety). The amino acid sequences of the mature retifanlimab heavy and light chains is described below.

Complementarity-determining regions (CDRs) 1, 2, and 3 of the variable heavy (VH) domain and the variable light (VL) domain are shown in that order from N to the C-terminus of the mature VL and VH sequences and are both underlined and boldened. An antibody consisting of the mature heavy chain (SEQ ID NO:2) and the mature light chain (SEQ ID NO:3) listed below is termed retifanlimab.

Mature Retifanlimab Heavy Chain (HC)

(SEQ ID NO: 2)
QVQLVQSGAEVKKPGASVKVSCKASGYSFTSYWMNWVRQAPGQGLEWIG

VIHPSDSETWLDQKFKDRVTITVDKSTSTAYMELSSLRSEDTAVYYCAR

EHYGTSPFAYWGQGTLVTVSSASTKGPSVFPLAPCSRSTSESTAALGCL

VKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPK

PKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPR

EPQVYTLPPSQEEMTKNQVSLTCLVKGFYPSDIAVEWESNGQPENNYKT

TPPVLDSDGSFFLYSRLTVDKSRWQEGNVFSCSVMHEALHNHYTQKSLS

LSLG

Mature Retifanlimab Light Chain (LC)

(SEQ ID NO: 3)
EIVLTQSPATLSLSPGERATLSCRASESVDNYGMSFMNWFQQKPGQPPK

LLIHAASNQGSGVPSRFSGSGSGTDFTLTISSLEPEDFAVYFCQQSKEV

PYTFGGGTKVEIKRTVAAPSVFIFPPSDEQLKSGTASVVCLLNNFYPRE

AKVQWKVDNALQSGNSQESVTEQDSKDSTYSLSSTLTLSKADYEKHKVY

ACEVTHQGLSSPVTKSFNRGEC

The variable heavy (VH) domain of retifanlimab has the following amino acid sequence:

(SEQ ID NO: 4)
QVQLVQSGAEVKKPGASVKVSCKASGYSFTSYWMNWVRQAPGQGLEWIG

VIHPSDSETWLDQKFKDRVTITVDKSTSTAYMELSSLRSEDTAVYYCAR

EHYGTSPFAYWGQGTLVTVSS

The variable light (VL) domain of retifanlimab has the following amino acid sequence:

(SEQ ID NO: 5)
EIVLTQSPATLSLSPGERATLSCRASESVDNYGMSFMNWFQQKPGQPPK

LLIHAASNQGSGVPSRFSGSGSGTDFTLTISSLEPEDFAVYFCQQSKEV

PYTFGGGTKVEIK

The amino acid sequences of the VH CDRs of retifanlimab are listed below:
VH CDR1: SYWMN (SEQ ID NO:6);
VH CDR2: VIHPSDSETWLDQKFKD (SEQ ID NO:7);
VH CDR3: EHYGTSPFAY (SEQ ID NO:8)

The amino acid sequences of VL CDRs of retifanlimab are listed below:
VL CDR1: RASESVDNYGMSFMNW (SEQ ID NO:9);
VL CDR2: AASNQGS (SEQ ID NO:10); and
VL CDR3: QQSKEVPYT (SEQ ID NO:11).

Accordingly, the present disclosure provides a method of treating cancer in a patient, comprising administering to said patient:
(i) Compound 1, having the structure:

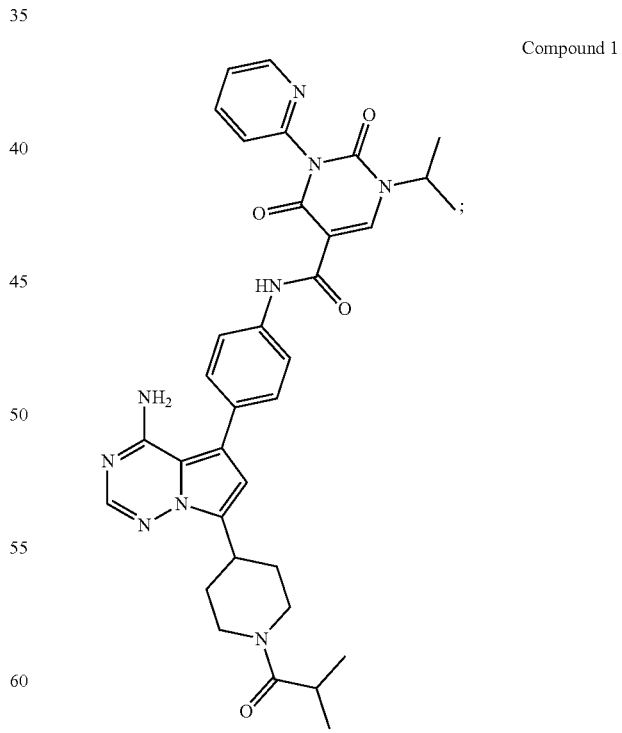

Compound 1 or a pharmaceutically acceptable salt thereof; and
(ii) an antibody, or an antigen-binding fragment thereof, that binds to human PD-1, wherein the antibody comprises (ii-1) a variable heavy (VH) domain comprising VH complementarity determining region (CDR)1, VH CDR2, and VH CDR3; and (ii-2) a variable light (VL) domain comprising VL CDR1, VL CDR2, and VL CDR3; wherein:

(a) the VH CDR1 comprises the amino acid sequence SYWMN (SEQ ID NO:6);
(b) the VH CDR2 comprises the amino acid sequence VIHPSDSETWLDQKFKD (SEQ ID NO:7);
(c) the VH CDR3 comprises the amino acid sequence EHYGTSPFAY (SEQ ID NO:8);
(d) the VL CDR1 comprises the amino acid sequence RASESVDNYGMSFMNW (SEQ ID NO:9);
(e) the VL CDR2 comprises the amino acid sequence AASNQGS (SEQ ID NO:10); and
(f) the VL CDR3 comprises the amino acid sequence QQSKEVPYT (SEQ ID NO:11).

In some embodiments, the VH domain comprises the amino acid sequence set forth in SEQ ID NO:4.

In some embodiments, the VL domain comprises the amino acid sequence set forth in SEQ ID NO:5.

In some embodiments, the VH domain comprises the amino acid sequence set forth in SEQ ID NO:4 and the VL domain comprises the amino acid sequence set forth in SEQ ID NO:5.

In some embodiments, the antibody comprises a variant Fc Region that comprises:
(A) one or more amino acid modifications that reduce the affinity of the variant Fc Region for an FcγR, wherein the one or more modifications that reduce the affinity of the variant Fc Region for an FcγR comprise the substitution of L234A; L235A; or L234A and L235A, and wherein the numbering is that of the EU index as in Kabat; and/or
(b) one or more amino acid modifications that enhance the serum half-life of the variant Fc Region, wherein the one or more modifications that enhance the serum half-life of the variant Fc Region comprise the substitution of M252Y; M252Y and S254T; M252Y and T256E; M252Y, S254T and T256E; or K288D and H435K, and wherein the numbering is that of the EU index as in Kabat.

In some embodiments, the antibody comprises an Fc Region wherein the Fc Region is of the IgG4 isotype. In some embodiments, the antibody comprises an Fc Region of the IgG4 isotype and an IgG4 Hinge Domain that comprises a stabilizing mutation. In some embodiments, the antibody comprises an Fc Region of the IgG4 isotype and an IgG4 Hinge Domain that comprises a S228P substitution (see, e.g., SEQ ID NO:12: ESKYGPPCPPCP, (Lu et al, (2008) "The Effect Of A Point Mutation On The Stability Of IgG4 As Monitored By Analytical Ultracentrifugation," J. Pharmaceutical Sciences 97:960-969) to reduce the incidence of strand exchange. Accordingly, in some embodiments, (a) the antibody comprises an Fc Region and a Hinge Domain; (b) the Fc Region and the Hinge Domain are of the IgG4 type; and
(c) the Hinge Domain comprises a stabilizing mutation.

In some embodiments, the antibody comprises a heavy chain, wherein the heavy chain comprises the amino acid sequence set forth in SEQ ID NO:2.

In some embodiments, the VL domain comprises the amino acid sequence set forth in SEQ ID NO:5.

In some embodiments, the antibody comprises a light chain, wherein the light chain comprises the amino acid sequence set forth in SEQ ID NO:3.

In some embodiments, the VH domain comprises the amino acid sequence set forth in SEQ ID NO:4 and the VL domain comprises the amino acid sequence set forth in SEQ ID NO:5.

In some embodiments, the antibody comprises a heavy chain and a light chain, and wherein the heavy chain comprises the amino acid sequence set forth in SEQ ID NO:2 and the light chain comprises the amino acid sequence set forth in SEQ ID NO:3.

In some embodiments, the antibody comprises an Fc Region that is of the IgG1 type.

In some embodiments, the antibody comprises an Fc Region that is of the IgG1 type, comprising a variant CH2-CH3 Domain (comprising the L234A/L235A (AA) substitution), but but lacking the C-terminal lysine residue. In some embodiments, the antibody comprises an Fc Region that is of the IgG1 type, wherein the mature heavy chain and light chain sequences are SEQ ID NO:13 and SEQ ID NO:3.

Mature Heavy Chain (HC)

(SEQ ID NO: 13)
```
QVQLVQSGAE VKKPGASVKV SCKASGYSFT SYWMNWVRQA

PGQGLEWIGV IHPSDSETWL DQKFKDRVTI TVDKSTSTAY

MELSSLRSED TAVYYCAREH YGTSPFAYWG QGTLVTVSSA

STKGPSVFPL APSSKSTSGG TAALGCLVKD YFPEPVTVSW

NSGALTSGVH TFPAVLQSSG LYSLSSVVTV PSSSLGTQTY

ICNVNHKPSN TKVDKRVEPK SCDKTHTCPP CPAPEAAGGP

SVFLFPPKPK DTLMISRTPE VTCVVVDVSH EDPEVKENWY

VDGVEVHNAK TKPREEQYNS TYRVVSVLTV LHQDWLNGKE

YKCKVSNKAL PAPIEKTISK AKGQPREPQV YTLPPSREEM

TKNQVSLTCL VKGFYPSDIA VEWESNGQPE NNYKTTPPVL

DSDGSFFLYS KLTVDKSRWQ QGNVFSCSVM HEALHNHYTQ

KSLSLSPG
```

In some embodiments, the antibody or antigen-binding fragment is a humanized antibody.

In some embodiments, Compound 1, or a pharmaceutically acceptable salt thereof, and the retifanlimab are administered to a patient simultaneously or sequentially. In some embodiments, Compound 1, or a pharmaceutically acceptable salt thereof, and the retifanlimab are administered to a patient simultaneously. In some embodiments, Compound 1, or a pharmaceutically acceptable salt thereof, and the retifanlimab are administered to a patient sequentially.

Compound 1 and its pharmaceutically acceptable salts can be administered to a subject, e.g., a subject in need thereof, for example, a human subject, by a variety of methods. For many applications, the route of administration is oral. In some embodiments, Compound 1, or a pharmaceutically acceptable salt thereof, is administered as a pharmaceutical composition.

Formulations (e.g., solid oral dosage forms) of Compound 1 are described in US Patent Publication No. 2020/0000812 A1, which is incorporated by reference in its entirety. In some embodiments, Compound 1 is formulated in solid oral dosage form comprising:
(a) Compound 1 or a pharmaceutically acceptable salt (e.g., Compound 1 maleate), solvate or hydrate thereof;
(b) an organic acid; and
(c) a surfactant.

The term "organic acid" refers to an organic compound with acidic properties. In some embodiments, the organic acid is $C_{1-6}$ alkyl, $C_2$-6 alkenyl, or 5-6 membered heterocycloalkyl, each substituted with one or more acidic groups (e.g., 1, 2, or 3 carboxylic acid, alcohol, or sulfonic acid groups), wherein the 5-6 membered heterocycloalkyl is optionally substituted with a $C_{1-6}$ alkyl group that is optionally substituted with one or more acidic groups (e.g., 1, 2, 3, or 4 carboxylic acid, alcohol, or sulfonic acid groups). The organic acid can be a $C_{1-6}$ alkyl or $C_2$-6 alkenyl substituted with one or more acidic groups (e.g., 1, 2, 3, or 4 carboxylic acid, alcohol, or sulfonic acid groups). In some embodiments, the organic acid is a $C_{1-6}$ alkyl or $C_2$-6 alkenyl substituted with 1, 2, or 3 carboxylic acid groups and substituted with 0, 1, or 2 alcohol groups. In some embodiments, the organic acid is 5-6 membered heterocycloalkyl substituted with one or more acidic groups (e.g., 1, 2, or 3 carboxylic acid, alcohol, or sulfonic acid groups) and optionally substituted with a $C_{1-6}$ alkyl, wherein the $C_{1-6}$ alkyl is optionally substituted with one or more acidic groups (e.g., 1, 2, or 3 carboxylic acid, alcohol, or sulfonic acid groups). Exemplary organic acids include, but are not limited to, citric acid, ascorbic acid, fumaric acid, malic acid, sorbic acid, tartaric acid and hydrates or solvates thereof. The organic acid in the formulation can be from about 1 wt % and to about 50 wt %. The organic acid in the formulation can be from about 5 wt % to about 40 wt %. The organic acid in the formulation can be from about 5 wt % to about 30 wt %. The organic acid in the formulation can be from about 5 wt % to about 20 wt %. The organic acid in the formulation can be from about 10 wt % to about 20 wt %. For example, the organic acid in the formulation can be about 1, 2, 3, 4, 5, 6, 7, 8, 9, 10, 15, 20, 25, 30, 35, 40, 45 or 50% by weight. In some embodiments, the organic acid in the formation is about 10 wt %. In some embodiments, the organic acid in the formation is about 20 wt %.

In some embodiments, the organic acid is citric acid. In some embodiments, the citric acid is citric acid monohydrate. The citric acid in the formulation can be from about 1 wt % and to about 50 wt %. The citric acid in the formulation can be from about 5 wt % to about 40 wt %. The citric acid in the formulation can be from about 5 wt % to about 30 wt %. The citric acid in the formulation can be from about 5 wt % to about 20 wt %. The citric acid in the formulation can be from about 10 wt % to about 20 wt %. For example, the citric acid in the formulation can be about 1, 2, 3, 4, 5, 6, 7, 8, 9, 10, 15, 20, 25, 30, 35, 40, 45 or 50% by weight. In some embodiments, the citric acid in the formation is about 10 wt %. In some embodiments, the citric acid in the formation is about 20 wt %.

The surfactant can help increase bioavailability of Compound 1, or a pharmaceutically acceptable salt (e.g., Compound 1 maleate), solvate, or hydrate thereof. The term "surfactants" refers to compounds that lower the surface tension between two liquids, or between a liquid and a solid. In some embodiments, surfactants can also have other functions such as detergents, wetting agents, emulsifiers, foaming agents, and dispersants. Exemplary surfactants include, but are not limited to, poloxamers. Examples of poloxamers are poloxamer 407, poloxamer 338, poloxamer 237, and poloxamer 188. In one embodiment, the poloxamer is poloxamer 188. In one embodiment, the poloxamer is poloxamer 407. Poloxamer is a polyethylene-propylene glycol copolymer (known trade names are Supronic, Pluronic or Tetronic) that has thermoreversible property and sol-gel transition property that can help drug release. For example, poloxamer exhibits in a sol state at less than room temperature and converts to a gel state at body temperature (37.2° C.), which can modify drug release characteristics (D. Ramya Devi et al, J. Pharm. Sci. & Res. Vol. 5(8), 2013, 159-165; Y. Mao et al. Journal of Pharmaceutical and Biomedical Analysis 35 (2004) 1127-1142).

The anti-PD-1 antibody or antigen-binding fragment thereof can be administered to a subject, e.g., a subject in need thereof, for example, a human subject, by a variety of methods. For many applications, the route of administration is one of: intravenous injection or infusion (IV), subcutaneous injection (SC), intraperitoneally (IP), or intramuscular injection. It is also possible to use intra-articular delivery. Other modes of parenteral administration can also be used. Examples of such modes include: intraarterial, intrathecal, intracapsular, intraorbital, intracardiac, intradermal, transtracheal, subcuticular, intraarticular, subcapsular, subarachnoid, intraspinal, and epidural and intrasternal injection. In some cases, administration can be oral.

The anti-PD-1 antibody or antigen-binding fragment thereof can be administered to a subject, e.g., a subject in need thereof, for example, a human subject, by a variety of methods. For many applications, the route of administration is one of: intravenous injection or infusion (IV), subcutaneous injection (SC), intraperitoneally (IP), or intramuscular injection. It is also possible to use intra-articular delivery. Other modes of parenteral administration can also be used. Examples of such modes include: intraarterial, intrathecal, intracapsular, intraorbital, intracardiac, intradermal, transtracheal, subcuticular, intraarticular, subcapsular, subarachnoid, intraspinal, and epidural and intrasternal injection. In some cases, administration can be oral.

The route and/or mode of administration of the antibody or antigen-binding fragment thereof can also be tailored for the individual case, e.g., by monitoring the subject, e.g., using tomographic imaging, e.g., to visualize a tumor.

The antibody or antigen-binding fragment thereof can be administered as a fixed dose, or in a mg/kg dose. The dose can also be chosen to reduce or avoid production of antibodies against the anti-PD-1 antibody. Dosage regimens are adjusted to provide the desired response, e.g., a therapeutic response or a combinatorial therapeutic effect. Generally, doses of the anti-PD-1 antibody (and optionally a second agent) can be used in order to provide a subject with the agent in bioavailable quantities. For example, doses in the range of 0.1-100 mg/kg, 0.5-100 mg/kg, 1 mg/kg-100 mg/kg, 0.5-20 mg/kg, 0.1-10 mg/kg, or 1-10 mg/kg can be administered. Other doses can also be used. In specific embodiments, a subject in need of treatment with an anti-PD-1 antibody is administered the antibody at a dose of 1 mg/kg, 2 mg/kg, 3 mg/kg, 4 mg/kg, 5 mg/kg, 10 mg/kg, 15 mg/kg, 20 mg/kg, 30 mg/kg, 35 mg/kg, or 40 mg/kg.

A composition may comprise about 1 mg/mL to 100 mg/ml or about 10 mg/mL to 100 mg/ml or about 50 to 250 mg/mL or about 100 to 150 mg/ml or about 100 to 250 mg/ml of anti-PD-1 antibody or antigen-binding fragment thereof.

Dosage unit form or "fixed dose" or "flat dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with the other agent. Single or multiple dosages may be given. Alternatively, or in addition, the antibody may be administered via continuous infusion. Exemplary fixed doses include 375 mg, 500 mg and 750 mg.

An anti-PD-1 antibody or antigen-binding fragment thereof dose can be administered, e.g., at a periodic interval over a period of time (a course of treatment) sufficient to encompass at least 2 doses, 3 doses, 5 doses, 10 doses, or more, e.g., once or twice daily, or about one to four times per week, or preferably weekly, biweekly (every two weeks), every three weeks, monthly, e.g., for between about 1 to 12 weeks, preferably between 2 to 8 weeks, more preferably between about 3 to 7 weeks, and even more preferably for about 4, 5, or 6 weeks. Factors that may influence the dosage and timing required to effectively treat a subject, include, e.g., the severity of the disease or disorder, formulation, route of delivery, previous treatments, the general health and/or age of the subject, and other diseases present. Moreover, treatment of a subject with a therapeutically effective amount of a compound can include a single treatment or, preferably, can include a series of treatments.

An exemplary dosing regimen comprises administration of an anti-PD-1 antibody or antigen-binding fragment thereof at a fixed dose of 375 mg once every 3 weeks. Another exemplary dosing regimen comprises administration of an anti-PD-1 antibody or antigen-binding fragment thereof at a fixed dose of 500 mg once every 4 weeks. Still another exemplary dosing regimen comprises administration of an anti-PD-1 antibody or antigen-binding fragment thereof at a fixed dose of 750 mg once every 4 weeks.

In some embodiments, the term "about" refers to plus or minus 10% of the value. A skilled person in the art would know that the values presented herein can vary due to the conditions of the experiments such as variability in data collection or instruments.

Compound 1

Compound 1 (N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide) has the following structure:

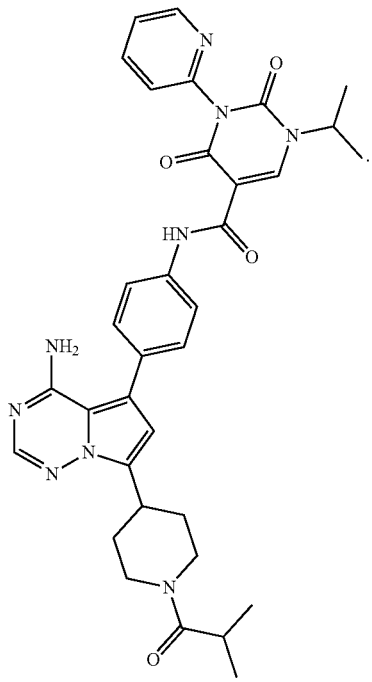 [SMILES: CC(C)C(=O)N1CCC(c2cc(-c3ccc(NC(=O)c4cn(C(C)C)c(=O)n(-c5ccccn5)c4=O)cc3)c3c(N)ncnn23)CC1]

Compound 1 can be synthesized as described in U.S. Pat. No. 9,981,975 and US Publication No. 2019/112313, which are incorporated herein by reference in their entirety.

The present disclosure also includes pharmaceutically acceptable salts of Compound 1 described herein.

Crystalline salt forms of Compound 1 are described in US Publication No. 2019/112313, which is incorporated herein by reference in its entirety.

In some embodiments, Compound 1 and salts thereof are substantially isolated. By "substantially isolated" is meant that the compound is at least partially or substantially separated from the environment in which it was formed or detected. Partial separation can include, for example, a composition enriched in Compound 1. Substantial separation can include compositions containing at least about 50%, at least about 60%, at least about 70%, at least about 80%, at least about 90%, at least about 95%, at least about 97%, or at least about 99% by weight of Compound 1, or salt thereof. Methods for isolating compounds and their salts are routine in the art.

Compound 1 can exist in various solid forms. As used herein "solid form" is meant to refer to a solid characterized by one or more properties such as, for example, melting point, solubility, stability, crystallinity, hygroscopicity, water content, TGA features, DSC features, DVS features, XRPD features, etc. Solid forms, for example, can be amorphous, crystalline, or mixtures thereof.

Different crystalline solid forms typically have different crystalline lattices (e.g., unit cells) and, usually as a result, have different physical properties. In some instances, different crystalline solid forms have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), and the like further help identify the solid form as well as help determine stability and solvent/water content.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the instrument or the settings. As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc.

Accordingly, in some embodiments, the present application provides N-(4-(4-Amino-7-(1-isobutyrylpiperidin-4-yl)pyrrolo[1,2-f][1,2,4]triazin-5-yl)phenyl)-1-isopropyl-2,4-dioxo-3-(pyridin-2-yl)-1,2,3,4-tetrahydropyrimidine-5-carboxamide maleic acid salt (also referred to herein as maleate salt of Compound 1, Compound 1 maleate salt, or any variation thereof).

In some embodiments, the salt is a 1:1 stoichiometric ratio of N-(4-(4-Amino-7-(1-isobutyrylpiperidin-4-yl)pyrrolo[1, 2-f][1,2,4]triazin-5-yl)phenyl)-1-isopropyl-2,4-dioxo-3-(pyridin-2-yl)-1,2,3,4-tetrahydropyrimidine-5-carboxamide to maleic acid.

In some embodiments, the maleic acid salt of Compound 1 provided herein is crystalline. As used herein, "crystalline" or "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content.

The maleic acid salt of the compound of Compound 1 can be prepared in various crystalline forms including, e.g., Form I, Form II, Form III, Form IV, or Form V as described in US Publication No. 2019/112313, which is incorporated herein by reference in its entirety.

Compound 1 Maleic Acid Salt, Form I:

Provided herein is a crystalline form of Compound 1, referred to as Form I, which is described below in Example 5.

In some embodiments, the maleic acid salt of Compound 1 has at least one XRPD peak, in terms of 2-theta, selected from about 4.3°, about 8.4°, about 12.6°, about 13.2°, and about 18.5°.

In some embodiments, the maleic acid salt of Compound 1 has at least two XRPD peaks, in terms of 2-theta, selected from about 4.3°, about 8.4°, about 12.6°, about 13.2°, and about 18.5°.

In some embodiments, the maleic acid salt of Compound 1 has at least three XRPD peaks, in terms of 2-theta, selected from about 4.3°, about 8.4°, about 12.6°, about 13.2°, and about 18.5°.

In some embodiments, the maleic acid salt of Compound 1 has at least four XRPD peak, in terms of 2-theta, selected from about 4.3°, about 8.4°, about 12.6°, about 13.2°, and about 18.5°.

In some embodiments, the maleic acid salt of Compound 1 comprises the following XRPD peaks, in terms of 2-theta: about 4.3°, about 8.4°, about 12.6°, about 13.2°, and about 18.5°.

In some embodiments, the maleic acid salt of Compound 1 comprises the following XRPD peaks, in terms of 2-theta: about 4.3°, about 8.4°, and about 13.2°.

In some embodiments, the maleic acid salt of Compound 1 has a DSC thermogram having an endothermic peak at about 211° C.

Compound 1 Maleic Acid Salt, Form II:

Provided herein is a crystalline form of Compound 1, referred to as Form II, which is described below in Examples 6 and 7.

In some embodiments, Form II of the maleic acid salt of Compound 1 has at least one XRPD peak, in terms of 2-theta, selected from about 3.8°, about 7.8°, about 23.5°, and about 26.0°.

In some embodiments, Form II of the maleic acid salt of Compound 1 has at least two XRPD peaks, in terms of 2-theta, selected from about 3.8°, about 7.8°, about 23.5°, and about 26.0°.

In some embodiments, Form II of the maleic acid salt of Compound 1 has at least three XRPD peaks, in terms of 2-theta, selected from about 3.8°, about 7.8°, about 23.5°, and about 26.0°.

In some embodiments, Form II the maleic acid salt of Compound 1 comprises the following XRPD peaks, in terms of 2-theta: about 3.8°, about 7.8°, about 23.5°, and about 26.0°.

In some embodiments, Form II of the maleic acid salt of Compound 1 comprises the following XRPD peaks, in terms of 2-theta: about 3.8°, about 7.8°, and about 23.5°.

Compound 1 Maleic Acid Salt, Form III:

Provided herein is a crystalline form of Compound 1, referred to as Form III, which is described below in Examples 6 and 8.

In some embodiments, Form III of the maleic acid salt of Compound 1 has at least one XRPD peak, in terms of 2-theta, selected from about 3.8°, about 7.7°, about 12.1°, about 18.9°, and about 20.6°.

In some embodiments, Form III of the maleic acid salt of Compound 1 has at least two XRPD peaks, in terms of 2-theta, selected from about 3.8°, about 7.7°, about 12.1°, about 18.9°, and about 20.6°.

In some embodiments, Form III of the maleic acid salt of Compound 1 has at least three XRPD peaks, in terms of 2-theta, selected from about 3.8°, about 7.7°, about 12.1°, about 18.9°, and about 20.6°.

In some embodiments, Form III of the maleic acid salt of Compound 1 has at least four XRPD peaks, in terms of 2-theta, selected from about 3.8°, about 7.7°, about 12.1°, about 18.9°, and about 20.6°.

In some embodiments, Form III the maleic acid salt of Compound 1 comprises the following XRPD peaks, in terms of 2-theta: 3.8°, about 7.7°, about 12.1°, about 18.9°, and about 20.6°.

In some embodiments, Form III of the maleic acid salt of Compound 1 comprises the following XRPD peaks, in terms of 2-theta: about 3.8°, about 7.7°, about 12.1° and about 18.9°.

In some embodiments, Form III of the maleic acid salt of Compound 1 has a DSC thermogram having endothermic peaks at about 165.4° C. and about 195.4° C. In some embodiments, Form III of the maleic acid salt of Compound 1 has a DSC thermogram having an endothermic peak at about 165.4° C. In some embodiments, Form III of the maleic acid salt of Compound 1 has a DSC thermogram having an endothermic peak at about 195.4° C.

Compound 1 Maleic Acid Salt, Form IV:

Provided herein is a crystalline form of Compound 1, referred to as Form IV, which is described below in Examples 6 and 9.

In some embodiments, Form IV of the maleic acid salt of Compound 1 has at least one XRPD peak, in terms of 2-theta, selected from about 3.9°, about 4.6°, about 7.8°, about 9.1°, and about 22.8°.

In some embodiments, Form IV of the maleic acid salt of Compound 1 has at least two XRPD peaks, in terms of 2-theta, selected from about 3.9°, about 4.6°, about 7.8°, about 9.1°, and about 22.8°.

In some embodiments, Form IV of the maleic acid salt of Compound 1 has at least three XRPD peaks, in terms of 2-theta, selected from about 3.9°, about 4.6°, about 7.8°, about 9.1°, and about 22.8°.

In some embodiments, Form IV of the maleic acid salt of Compound 1 has at least four XRPD peaks, in terms of 2-theta, selected from about 3.9°, about 4.6°, about 7.8°, about 9.1°, and about 22.8°.

In some embodiments, Form IV the maleic acid salt of Compound 1 comprises the following XRPD peaks, in terms of 2-theta: about 3.9°, about 4.6°, about 7.8°, about 9.1°, and about 22.8°.

In some embodiments, Form IV of the maleic acid salt of Compound 1 comprises the following XRPD peaks, in terms of 2-theta: about 3.9°, about 4.6°, about 7.8°, and about 9.1°.

In some embodiments, Form IV of the maleic acid salt of Compound 1 has a DSC thermogram having endothermic peaks at about 152.1° C. and 202.6° C. In some embodiments, Form IV of the maleic acid salt of Compound 1 has a DSC thermogram having an endothermic peak at about 152.1° C. In some embodiments, Form IV of the maleic acid salt of Compound 1 has a DSC thermogram having an endothermic peak at about 202.6° C.

Compound 1 Maleic Acid Salt, Form V:

Provided herein is a crystalline form of Compound 1, referred to as Form V, which is described below in Examples 6 and 10.

In some embodiments, Form V of the maleic acid salt of Compound 1 has at least one XRPD peak, in terms of 2-theta, selected from about 4.1°, about 8.3°, about 8.8°, about 18.0°, and about 27.3°.

In some embodiments, Form V of the maleic acid salt of Compound 1 has at least two XRPD peaks, in terms of 2-theta, selected from about 4.1°, about 8.3°, about 8.8°, about 18.0°, and about 27.3°.

In some embodiments, Form V of the maleic acid salt of Compound 1 has at least three XRPD peaks, in terms of 2-theta, selected from about 4.1°, about 8.3°, about 8.8°, about 18.0°, and about 27.3°.

In some embodiments, Form V of the maleic acid salt of Compound 1 has at least four XRPD peaks, in terms of 2-theta, selected from about 4.1°, about 8.3°, about 8.8°, about 18.0°, and about 27.3°.

In some embodiments, Form V the maleic acid salt of Compound 1 comprises the following XRPD peaks, in terms of 2-theta: about 4.1°, about 8.3°, about 8.8°, about 18.0°, and about 27.3°.

In some embodiments, Form V of the maleic acid salt of Compound 1 comprises the following XRPD peaks, in terms of 2-theta: about 4.1°, about 8.3°, about 8.8°, and about 27.3°.

In some embodiments, Form V of the maleic acid salt of Compound 1 has a DSC thermogram having an endothermic peak at about 200.1° C.

Preparation of Antibodies and Pharmaceutical Compositions of Antibodies

In certain embodiments, the antibodies that bind to human PD-1 include a human heavy chain and light chain constant region. In certain embodiments, the heavy chain constant region comprises a CH1 domain and a hinge region. In some embodiments, the heavy chain constant region comprises a CH3 domain. If the heavy chain constant region includes substitutions, such substitutions modify the properties of the antibody (e.g., increase or decrease one or more of: Fc receptor binding, antibody glycosylation, the number of cysteine residues, effector cell function, or complement function). In certain embodiments, the antibody is an IgG antibody. In specific embodiments, the antibody is selected from the group consisting of IgG1, IgG2, IgG3, and IgG4.

Antibodies, such as retifanlimab, can be made, for example, by preparing and expressing synthetic genes that encode the recited amino acid sequences or by mutating human germline genes to provide a gene that encodes the recited amino acid sequences. Moreover, this antibody and other antibodies that bind to human PD-1 can be obtained, e.g., using one or more of the following methods.

Humanized antibodies can be generated by replacing sequences of the Fv variable region that are not directly involved in antigen binding with equivalent sequences from human Fv variable regions. General methods for generating humanized antibodies are provided by Morrison, S. L., *Science*, 229:1202-1207 (1985), by Oi et al., *BioTechniques*, 4:214 (1986), and by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target, as described above, from germline immunoglobulin genes, or from synthetic constructs. The recombinant DNA encoding the humanized antibody can then be cloned into an appropriate expression vector.

Human germline sequences, for example, are disclosed in Tomlinson, I. A. et al., *J. Mol. Biol.*, 227:776-798 (1992); Cook, G. P. et al., *Immunol. Today*, 16: 237-242 (1995); Chothia, D. et al., *J. Mol. Bio.* 227:799-817 (1992); and Tomlinson et al., *EMBO J.*, 14:4628-4638 (1995). The V BASE directory provides a comprehensive directory of human immunoglobulin variable region sequences (compiled by Tomlinson, I. A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064.

Other methods for humanizing antibodies can also be used. For example, other methods can account for the three dimensional structure of the antibody, framework positions that are in three-dimensional proximity to binding determinants, and immunogenic peptide sequences. See, e.g., WO 90/07861; U.S. Pat. Nos. 5,693,762; 5,693,761; 5,585,089; 5,530,101; and U.S. Pat. No. 6,407,213; Tempest et al. (1991) *Biotechnology* 9:266-271. Still another method is termed "humaneering" and is described, for example, in U.S. 2005-008625.

The antibody can include a human Fc region, e.g., a wild-type Fc region or an Fc region that includes one or more alterations. In one embodiment, the constant region is altered, e.g., mutated, to modify the properties of the antibody (e.g., to increase or decrease one or more of: Fc receptor binding, antibody glycosylation, the number of cysteine residues, effector cell function, or complement function). For example, the human IgG1 constant region can be mutated at one or more residues, e.g., one or more of residues 234 and 237 (based on Kabat numbering). Antibodies may have mutations in the CH2 region of the heavy chain that reduce or alter effector function, e.g., Fc receptor binding and complement activation. For example, antibodies may have mutations such as those described in U.S. Pat. Nos. 5,624,821 and 5,648,260. Antibodies may also have mutations that stabilize the disulfide bond between the two heavy chains of an immunoglobulin, such as mutations in the hinge region of IgG4, as disclosed in the art (e.g., Angal et al. (1993) *Mol. Immunol.* 30:105-08). See also, e.g., U.S. 2005-0037000.

The antibodies that bind to human PD-1 or human PD-L1 can be in the form of full length antibodies, or in the form of low molecular weight forms (e.g., biologically active antibody fragments or minibodies) of the antibodies that bind to human PD-1 or human PD-L1, e.g., Fab, Fab', F(ab')2, Fv, Fd, dAb, scFv, and sc(Fv)2. Other antibodies encompassed by this disclosure include single domain antibody (sdAb) containing a single variable chain such as, VH or VL, or a biologically active fragment thereof. See, e.g., Moller et al., *J. Biol. Chem.*, 285(49): 38348-38361 (2010); Harmsen et al., *Appl. Microbiol. Biotechnol.*, 77(1):13-22 (2007); U.S. 2005/0079574 and Davies et al. (1996) *Protein Eng.*, 9(6):531-7. Like a whole antibody, a sdAb is able to bind selectively to a specific antigen. With a molecular weight of only 12-15 kDa, sdAbs are much smaller than common antibodies and even smaller than Fab fragments and single-chain variable fragments.

Provided herein are compositions comprising a mixture of an antibody that binds to human PD-1 or human PD-L1, or antigen-binding fragment thereof, and one or more acidic variants thereof, e.g., wherein the amount of acidic variant(s) is less than about 80%, 70%, 60%, 60%, 50%, 40%, 30%, 30%, 20%, 10%, 5% or 1%. Also provided are compositions comprising an antibody that binds to human PD-1 or human PD-L1, or antigen-binding fragment thereof, comprising at least one deamidation site, wherein the pH of the composition is from about 5.0 to about 6.5, such that, e.g., at least about 90% of the antibodies are not deamidated (i.e., less than about 10% of the antibodies are deamidated). In certain embodiments, less than about 5%, 3%, 2% or 1% of the antibodies are deamidated. The pH may be from 5.0 to 6.0, such as 5.5 or 6.0. In certain embodiments, the pH of the composition is 5.5, 5.6, 5.7, 5.8, 5.9, 6.0, 6.1, 6.2, 6.3, 6.4 or 6.5.

An "acidic variant" is a variant of a polypeptide of interest which is more acidic (e.g. as determined by cation exchange chromatography) than the polypeptide of interest. An example of an acidic variant is a deamidated variant.

A "deamidated" variant of a polypeptide molecule is a polypeptide wherein one or more asparagine residue(s) of the original polypeptide have been converted to aspartate, i.e. the neutral amide side chain has been converted to a residue with an overall acidic character.

The term "mixture" as used herein in reference to a composition comprising an antibody that binds to human PD-1 or human PD-L1 or antigen-binding fragment thereof, means the presence of both the desired antibody that binds to human PD-1 or human PD-L1, or antigen-binding fragment thereof, and one or more acidic variants thereof. The acidic variants may comprise predominantly deamidated antibody that binds to human PD-1 or human PD-L1, with minor amounts of other acidic variant(s).

In certain embodiments, the binding affinity ($K_D$), on-rate ($K_D$ on) and/or off-rate ($K_D$ off) of the antibody that was mutated to eliminate deamidation is similar to that of the wild-type antibody, e.g., having a difference of less than about 5 fold, 2 fold, 1 fold (100%), 50%, 30%, 20%, 10%, 5%, 3%, 2% or 1%.

Antibody Fragments

Antibody fragments (e.g., Fab, Fab', F(ab')2, Facb, and Fv) may be prepared by proteolytic digestion of intact antibodies. For example, antibody fragments can be obtained by treating the whole antibody with an enzyme such as papain, pepsin, or plasmin. Papain digestion of whole antibodies produces F(ab)2 or Fab fragments; pepsin digestion of whole antibodies yields F(ab')2 or Fab'; and plasmin digestion of whole antibodies yields Facb fragments.

Alternatively, antibody fragments can be produced recombinantly. For example, nucleic acids encoding the antibody fragments of interest can be constructed, introduced into an expression vector, and expressed in suitable host cells. See, e.g., Co, M. S. et al., *J. Immunol.*, 152:2968-2976 (1994); Better, M. and Horwitz, A. H., *Methods in Enzymology*, 178:476-496 (1989); Plueckthun, A. and Skerra, A., *Methods in Enzymology*, 178:476-496 (1989); Lamoyi, E., *Methods in Enzymology*, 121:652-663 (1989); Rousseaux, J. et al., *Methods in Enzymology*, (1989) 121: 663-669 (1989); and Bird, R. E. et al., *TIBTECH*, 9:132-137 (1991)). Antibody fragments can be expressed in and secreted from *E. coli*, thus allowing the facile production of large amounts of these fragments. Antibody fragments can be isolated from the antibody phage libraries. Alternatively, Fab'-SH fragments can be directly recovered from *E. coli* and chemically coupled to form F(ab)2 fragments (Carter et al., *Bio/Technology*, 10:163-167 (1992)). According to another approach, F(ab')2 fragments can be isolated directly from recombinant host cell culture. Fab and F(ab') 2 fragment with increased in vivo half-life comprising a salvage receptor binding epitope residues are described in U.S. Pat. No. 5,869,046.

Minibodies

Minibodies of antibodies that bind to human PD-1 or human PD-L1 include diabodies, single chain (scFv), and single-chain (Fv)2 (sc(Fv)2).

A "diabody" is a bivalent minibody constructed by gene fusion (see, e.g., Holliger, P. et al., *Proc. Natl. Acad. Sci. U.S.A.*, 90:6444-6448 (1993); EP 404,097; WO 93/11161). Diabodies are dimers composed of two polypeptide chains. The VL and VH domain of each polypeptide chain of the diabody are bound by linkers. The number of amino acid residues that constitute a linker can be between 2 to 12 residues (e.g., 3-10 residues or five or about five residues). The linkers of the polypeptides in a diabody are typically too short to allow the VL and VH to bind to each other. Thus, the VL and VH encoded in the same polypeptide chain cannot form a single-chain variable region fragment, but instead form a dimer with a different single-chain variable region fragment. As a result, a diabody has two antigen-binding sites.\

An scFv is a single-chain polypeptide antibody obtained by linking the VH and VL with a linker (see e.g., Huston et al., *Proc. Natl. Acad. Sci. U.S.A.*, 85:5879-5883 (1988); and Plickthun, "The Pharmacology of Monoclonal Antibodies" Vol. 113, Ed Resenburg and Moore, Springer Verlag, New York, pp. 269-315, (1994)). The order of VHs and VLs to be linked is not particularly limited, and they may be arranged in any order. Examples of arrangements include: [VH] linker [VL]; or [VL] linker [VH]. The H chain V region and L chain V region in an scFv may be derived from any antibody that binds to human PD-1 or human PD-L1, or antigen-binding fragment thereof, described herein.

An sc(Fv)2 is a minibody in which two VHs and two VLs are linked by a linker to form a single chain (Hudson, et al., *J. Immunol. Methods*, (1999) 231: 177-189 (1999)). An sc(Fv)2 can be prepared, for example, by connecting scFvs with a linker. The sc(Fv)2 of the present disclosure include antibodies preferably in which two VHs and two VLs are arranged in the order of: VH, VL, VH, and VL ([VH] linker [VL] linker [VH] linker [VL]), beginning from the N terminus of a single-chain polypeptide; however the order of the two VHs and two VLs is not limited to the above arrangement, and they may be arranged in any order.

Bispecific Antibodies

Bispecific antibodies are antibodies that have binding specificities for at least two different epitopes. Exemplary bispecific antibodies may bind to two different epitopes of the PD-1 protein. Other such antibodies may combine a PD-1 binding site with a binding site for another protein. Bispecific antibodies can be prepared as full length antibodies or low molecular weight forms thereof (e.g., F(ab') 2 bispecific antibodies, sc(Fv)2 bispecific antibodies, diabody bispecific antibodies).

Traditional production of full length bispecific antibodies is based on the co-expression of two immunoglobulin heavy chain-light chain pairs, where the two chains have different specificities (Millstein et al., *Nature*, 305:537-539 (1983)).

In a different approach, antibody variable domains with the desired binding specificities are fused to immunoglobulin constant domain sequences. DNAs encoding the immunoglobulin heavy chain fusions and, if desired, the immunoglobulin light chain, are inserted into separate expression vectors, and are co-transfected into a suitable host cell. This provides for greater flexibility in adjusting the proportions of the three polypeptide fragments. It is, however, possible to insert the coding sequences for two or all three polypeptide chains into a single expression vector when the expression of at least two polypeptide chains in equal ratios results in high yields.

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_{H3}$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods.

The "diabody" technology provides an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites.

Multivalent Antibodies

A multivalent antibody may be internalized (and/or catabolized) faster than a bivalent antibody by a cell expressing an antigen to which the antibodies bind. The antibodies describe herein can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. An exemplary dimerization domain comprises (or consists of) an Fc region or a hinge region. A multivalent antibody can comprise (or consist of) three to about eight (e.g., four) antigen binding sites. The multivalent antibody optionally comprises at least one polypeptide chain (e.g., at least two polypeptide chains), wherein the polypeptide chain(s) comprise two or more variable domains. For instance, the polypeptide chain (s) may comprise VD1-(X1)$_n$-VD2-(X2)$_n$-Fc, wherein VD1 is a first variable domain, VD2 is a second variable domain, Fc is a polypeptide chain of an Fc region, X1 and X2 represent an amino acid or peptide spacer, and n is 0 or 1.

Conjugated Antibodies

The antibodies disclosed herein may be conjugated antibodies which are bound to various molecules including macromolecular substances such as polymers (e.g., polyethylene glycol (PEG), polyethylenimine (PEI) modified with PEG (PEI-PEG), polyglutamic acid (PGA) (N-(2-Hydroxypropyl) methacrylamide (HPMA) copolymers), hyaluronic acid, radioactive materials (e.g. $^{90}Y$, $^{131}I$) fluorescent substances, luminescent substances, haptens, enzymes, metal chelates, drugs, and toxins (e.g., calcheamicin, *Pseudomonas* exotoxin A, ricin (e.g. deglycosylated ricin A chain)).

In one embodiment, to improve the cytotoxic actions of antibodies that bind to human PD-1 or human PD-L1 and consequently their therapeutic effectiveness, the antibodies are conjugated with highly toxic substances, including radioisotopes and cytotoxic agents. These conjugates can deliver a toxic load selectively to the target site (i.e., cells expressing the antigen recognized by the antibody) while cells that are not recognized by the antibody are spared. In order to minimize toxicity, conjugates are generally engineered based on molecules with a short serum half-life (thus, the use of murine sequences, and IgG3 or IgG4 isotypes).

In certain embodiments, an antibody that binds to human PD-1 or human PD-L1, or antigen-binding fragment thereof, are modified with a moiety that improves its stabilization and/or retention in circulation, e.g., in blood, serum, or other tissues, e.g., by at least 1.5, 2, 5, 10, or 50 fold. For example, the antibody that binds to human PD-1 or human PD-L1, or antigen-binding fragment thereof, can be associated with (e.g., conjugated to) a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used. For example, the antibody that binds to human PD-1 or human PD-L1, or antigen-binding fragment thereof, can be conjugated to a water-soluble polymer, e.g., a hydrophilic polyvinyl polymer, e.g., polyvinylalcohol or polyvinylpyrrolidone. Examples of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene; polymethacrylates; carbomers; and branched or unbranched polysaccharides.

The above-described conjugated antibodies can be prepared by performing chemical modifications on the antibodies or the lower molecular weight forms thereof described herein. Methods for modifying antibodies are well known in the art (e.g., U.S. Pat. Nos. 5,057,313 and 5,156,840).

Methods of Producing Antibodies

Antibodies may be produced in bacterial or eukaryotic cells. Some antibodies, e.g., Fab's, can be produced in bacterial cells, e.g., *E. coli* cells. Antibodies can also be produced in eukaryotic cells such as transformed cell lines (e.g., CHO, 293E, COS). In addition, antibodies (e.g., scFv's) can be expressed in a yeast cell such as *Pichia* (see, e.g., Powers et al., *J Immunol Methods.* 251:123-35 (2001)), *Hanseula*, or *Saccharomyces*. To produce the antibody of interest, a polynucleotide encoding the antibody is constructed, introduced into an expression vector, and then expressed in suitable host cells. Standard molecular biology techniques are used to prepare the recombinant expression vector, transfect the host cells, select for transformants, culture the host cells and recover the antibody.

If the antibody is to be expressed in bacterial cells (e.g., *E. coli*), the expression vector should have characteristics that permit amplification of the vector in the bacterial cells. Additionally, when *E. coli* such as JM109, DH5α, HB101, or XL1-Blue is used as a host, the vector must have a promoter, for example, a lacZ promoter (Ward et al., 341: 544-546 (1989), araB promoter (Better et al., *Science,* 240:1041-1043 (1988)), or T7 promoter that can allow efficient expression in *E. coli.* Examples of such vectors include, for example, M13-series vectors, pUC-series vectors, pBR322, pBluescript, pCR-Script, pGEX-5X-1 (Pharmacia), "QIAexpress system" (QIAGEN), pEGFP, and pET (when this expression vector is used, the host is preferably BL21 expressing T7 RNA polymerase). The expression vector may contain a signal sequence for antibody secretion. For production into the periplasm of *E. coli,* the pelB signal sequence (Lei et al., *J. Bacteriol.,* 169:4379 (1987)) may be used as the signal sequence for antibody secretion. For bacterial expression, calcium chloride methods or electroporation methods may be used to introduce the expression vector into the bacterial cell.

If the antibody is to be expressed in animal cells such as CHO, COS, and NIH3T3 cells, the expression vector includes a promoter necessary for expression in these cells, for example, an SV40 promoter (Mulligan et al., *Nature,* 277:108 (1979)), MMLV-LTR promoter, EF1α promoter (Mizushima et al., *Nucleic Acids Res.,* 18:5322 (1990)), or CMV promoter. In addition to the nucleic acid sequence encoding the immunoglobulin or domain thereof, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In one embodiment, antibodies are produced in mammalian cells. Exemplary mammalian host cells for expressing an antibody include Chinese Hamster Ovary (CHO cells) (including dhfr⁻ CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), human embryonic kidney 293 cells (e.g., 293, 293E, 293T), COS cells, NIH3T3 cells, lymphocytic cell lines, e.g., NS0 myeloma cells and SP2 cells, and a cell from a transgenic animal, e.g., a transgenic mammal. For example, the cell is a mammary epithelial cell.

In an exemplary system for antibody expression, a recombinant expression vector encoding both the antibody heavy chain and the antibody light chain of an antibody that binds to human PD-1 or human PD-L1 antibody is introduced into dhfr⁻ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and the antibody is recovered from the culture medium.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly. Animals are also provided comprising one or more of the nucleic acids described herein.

The antibodies of the present disclosure can be isolated from inside or outside (such as medium) of the host cell and purified as substantially pure and homogenous antibodies. Methods for isolation and purification commonly used for antibody purification may be used for the isolation and purification of antibodies, and are not limited to any particular method. Antibodies may be isolated and purified by appropriately selecting and combining, for example, column chromatography, filtration, ultrafiltration, salting out, solvent precipitation, solvent extraction, distillation, immunoprecipitation, SDS-polyacrylamide gel electrophoresis, isoelectric focusing, dialysis, and recrystallization. Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). Chromatography can be carried out using liquid phase chromatography such as HPLC and FPLC. Columns used for affinity chromatography include protein A column and protein G column. Examples of columns using protein A column include Hyper D, POROS, and Sepharose FF (GE Healthcare Biosciences). The present disclosure also includes antibodies that are highly purified using these purification methods.

Antibodies with Altered Glycosylation

Different glycoforms can profoundly affect the properties of a therapeutic, including pharmacokinetics, pharmacodynamics, receptor-interaction and tissue-specific targeting (Graddis et al., 2002, *Curr Pharm Biotechnol.* 3: 285-297). In particular, for antibodies, the oligosaccharide structure can affect properties relevant to protease resistance, the serum half-life of the antibody mediated by the FcRn receptor, phagocytosis and antibody feedback, in addition to effector functions of the antibody (e.g., binding to the complement complex C1, which induces CDC, and binding to FcγR receptors, which are responsible for modulating the ADCC pathway) (Nose and Wigzell, 1983; Leatherbarrow and Dwek, 1983; Leatherbarrow et al., 1985; Walker et al., 1989; Carter et al., 1992, *PNAS,* 89: 4285-4289).

Accordingly, another means of modulating effector function of antibodies includes altering glycosylation of the antibody constant region. Altered glycosylation includes, for example, a decrease or increase in the number of glycosylated residues, a change in the pattern or location of glycosylated residues, as well as a change in sugar structure(s). The oligosaccharides found on human IgGs affects their degree of effector function (Raju, T. S. *BioProcess International* April 2003. 44-53); the microheterogeneity of human IgG oligosaccharides can affect biological functions such as CDC and ADCC, binding to various Fc receptors, and binding to C1q protein (Wright A. & Morrison S L. TIBTECH 1997, 15 26-32; Shields et al. *J Biol Chem.* 2001 276(9):6591-604; Shields et al. *J Biol Chem.* 2002; 277(30): 26733-40; Shinkawa et al. *J Biol Chem.* 2003 278(5):3466-

73; Umana et al. *Nat Biotechnol.* 1999 February; 17(2): 176-80). For example, the ability of IgG to bind C1q and activate the complement cascade may depend on the presence, absence or modification of the carbohydrate moiety positioned between the two CH2 domains (which is normally anchored at Asn297) (Ward and Ghetie, *Therapeutic Immunology* 2:77-94 (1995).

Glycosylation sites in an Fc-containing polypeptide, for example an antibody such as an IgG antibody, may be identified by standard techniques. The identification of the glycosylation site can be experimental or based on sequence analysis or modeling data. Consensus motifs, that is, the amino acid sequence recognized by various glycosyl transferases, have been described. For example, the consensus motif for an N-linked glycosylation motif is frequently NXT or NXS, where X can be any amino acid except proline. Several algorithms for locating a potential glycosylation motif have also been described. Accordingly, to identify potential glycosylation sites within an antibody or Fc-containing fragment, the sequence of the antibody is examined, for example, by using publicly available databases such as the website provided by the Center for Biological Sequence Analysis (see NetNGlyc services for predicting N-linked glycosylation sites and NetOGlyc services for predicting O-linked glycosylation sites).

In vivo studies have confirmed the reduction in the effector function of aglycosyl antibodies. For example, an aglycosyl anti-CD8 antibody is incapable of depleting CD8-bearing cells in mice (Isaacs, 1992 *J. Immunol.* 148: 3062) and an aglycosyl anti-CD3 antibody does not induce cytokine release syndrome in mice or humans (Boyd, 1995 supra; Friend, 1999 *Transplantation* 68:1632). Aglycosylated forms of the PD-1 antibody also have reduced effector function.

Importantly, while removal of the glycans in the CH2 domain appears to have a significant effect on effector function, other functional and physical properties of the antibody remain unaltered. Specifically, it has been shown that removal of the glycans had little to no effect on serum half-life and binding to antigen (Nose, 1983 supra; Tao, 1989 supra; Dorai, 1991 supra; Hand, 1992 supra; Hobbs, 1992 *Mol. Immunol.* 29:949).

The antibodies that bind to human PD-1 or human PD-L1 of the present disclosure may be modified or altered to elicit increased or decreased effector function(s) (compared to a second PD-1-specific antibody). Methods for altering glycosylation sites of antibodies are described, e.g., in U.S. Pat. Nos. 6,350,861 and 5,714,350, WO 05/18572 and WO 05/03175; these methods can be used to produce antibodies of the present disclosure with altered, reduced, or no glycosylation.

Methods of Use

The methods described herein involve the treatment of cancers. Example cancers include bladder cancer, breast cancer, cervical cancer, colorectal cancer, cancer of the small intestine, colon cancer, rectal cancer, cancer of the anus, endometrial cancer, gastric cancer, head and neck cancer (e.g., cancers of the larynx, hypopharynx, nasopharynx, oropharynx, lips, and mouth), kidney cancer, liver cancer (e.g., hepatocellular carcinoma, cholangiocellular carcinoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, esophageal cancer, gall bladder cancer, pancreatic cancer (e.g. exocrine pancreatic carcinoma), stomach cancer, thyroid cancer, parathyroid cancer, skin cancer (e.g., squamous cell carcinoma, Kaposi sarcoma, Merkel cell skin cancer), and brain cancer (e.g., astrocytoma, medulloblastoma, ependymoma, neuroectodermal tumors, pineal tumors).

Other cancers treatable with the treatment methods of the disclosure include bone cancer, intraocular cancers, gynecological cancers, cancer of the endocrine system, cancer of the adrenal gland, sarcoma of soft tissue, cancer of the urethra, cancer of the penis, pituitary cancer, triple-negative breast cancer (TNBC) and environmentally induced cancers including those induced by asbestos.

Further example cancers include hematopoietic malignancies such as leukemia or lymphoma, multiple myeloma, chronic lymphocytic lymphoma, adult T cell leukemia, B-cell lymphoma, cutaneous T-cell lymphoma, acute myelogenous leukemia, Hodgkin's or non-Hodgkin's lymphoma, myeloproliferative neoplasms (e.g., polycythemia vera, essential thrombocythemia, and primary myelofibrosis), Waldenstrom's Macroglubulinemia, hairy cell lymphoma, chronic myelogenic lymphoma, acute lymphoblastic lymphoma, AIDS-related lymphomas, and Burkitt's lymphoma.

Other cancers treatable with the treatment methods of the disclosure include tumors of the eye, glioblastoma, melanoma, rhabdosarcoma, lymphosarcoma, and osteosarcoma.

The methods of the present disclosure are also useful for the treatment of metastatic cancers, especially metastatic cancers that express PD-L1.

In some embodiments, diseases and indications that are treatable using the methods of the present disclosure include, but are not limited to hematological cancers, head and neck cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), small lymphocytic lymphoma (SLL), chronic myelogenous leukemia (CIVIL), diffuse large B-cell lymphoma (DLBCL), mantle cell lymphoma (MCL), marginal zone lymphoma (MZL), Non-Hodgkin lymphoma (including relapsed or refractory NHL), follicular lymphoma (FL), Hodgkin lymphoma, lymphoblastic lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL), multiple myeloma, cutaneous T-cell lymphoma, peripheral T-cell lymphoma, Waldenstrom's Macroglubulinemia, hairy cell lymphoma, chronic myelogenic lymphoma and Burkitt's lymphoma.

Exemplary sarcomas include chondrosarcoma, Ewing's sarcoma, osteosarcoma, rhabdomyosarcoma, angio sarcoma, fibro sarcoma, lipo sarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), colorectal cancer and bile duct cancer.

Exemplary genitourinary tract cancers include cancers of the kidney (adenocarcinoma, Wilm's tumor [nephroblastoma], renal cell carcinoma), bladder and urethra (squamous cell carcinoma, transitional cell carcinoma, adenocarcinoma, urothelial carcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma, Lhermitte-Duclos disease, neoplasm of the central nervous system (CNS), primary CNS lymphoma and spinal axis tumor.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers.

In some embodiments, the present disclosure provides a method for treating hepatocellular carcinoma in a patient in need thereof. In some embodiments, the present disclosure provides a method for treating Rhabdomyosarcoma, esophageal cancer, breast cancer, or cancer of a head or neck, in a patient in need thereof.

In some embodiments, the present disclosure provides a method of treating cancer, wherein the cancer is selected from hepatocellular cancer, bladder cancer, breast cancer, cervical cancer, colorectal cancer, endometrial cancer, anal cancer, Merkel cell carcinoma, gastric cancer, head and neck cancer, kidney cancer, liver cancer, lung cancer, ovarian cancer, prostate cancer, esophageal cancer, gall bladder cancer, pancreatic cancer, thyroid cancer, skin cancer, leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's Macroglubulinemia, hairy cell lymphoma, Burkett's lymphoma, glioblastoma, melanoma, and rhabdosarcoma.

In some embodiments, the present disclosure provides a method of treating cancer, wherein the cancer is selected from hepatocellular cancer, breast cancer, bladder cancer, colorectal cancer, melanoma, mesothelioma, lung cancer, prostate cancer, pancreatic cancer, testicular cancer, thyroid cancer, squamous cell carcinoma, glioblastoma, neuroblastoma, uterine cancer, and rhabdosarcoma.

In some embodiments, the present disclosure provides a method of treating cancer, wherein the cancer is selected from sarcoma, head and neck cancer, melanoma, and non-small cell lung cancer. In some embodiments, the cancer is sarcoma. In some embodiments, the cancer is head and neck cancer. In some embodiments, the cancer is melanoma. In some embodiments, the cancer is non-small cell lung cancer.

The methods described herein involve the treatment of cancers, for example solid tumors.

In some embodiments, the solid tumor is selected from skin cancer, lung cancer, lymphoma, sarcoma, bladder cancer, cancer of the ureter, urethra, and urachus, gastric cancer, cervical cancer, liver cancer, breast cancer, renal cancer, squamous cell carcinoma, colorectal cancer, endometrial cancer, anal cancer, and a tumor with microsatellite instability-high (MSI-H), mismatch repair deficient (dMMR) and/or DNA polymerase c exonuclease domain mutation positive disease.

In some embodiments, the solid tumor is selected from cholangiocarcinoma, melanoma, non-small cell lung cancer, small cell lung cancer, Hodgkin's lymphoma, urothelial carcinomagastric cancer, hepatocellular carcinoma, Merkel cell carcinoma, triple-negative breast cancer, renal cell carcinoma, squamous cell carcinoma of the head and neck, and colorectal cancer.

In some embodiments, the solid tumor is selected from sarcomas, head and neck cancer, melanoma, and non-small cell lung cancer. In some embodiments, the solid tumor is sarcoma. In some embodiments, the solid tumor is head and neck cancer. In some embodiments, the solid tumor is melanoma. In some embodiments, the solid tumor is non-small cell lung cancer.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" a TAM kinase with Compound 1 includes the administration of Compound 1 to an individual or patient, such as a human, as well as, for example, introducing Compound 1 into a sample containing a cellular or purified preparation containing a TAM kinase.

As used herein, the term "subject", "individual" or "patient," used interchangeably, refers to any animal, including mammals, preferably mice, rats, other rodents, rabbits, dogs, cats, swine, cattle, sheep, horses, or primates, and most preferably humans.

As used herein, the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "preventing" or "prevention" refers to preventing a disease, condition or disorder in an individual who may be predisposed to the disease, condition or disorder but does not yet experience or display the pathology or symptomatology of the disease.

Combination Therapy
I. Cancer Therapies

Cancer cell growth and survival can be impacted by dysfunction in multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF, FAK, CDK2, and CDK4/6 kinase inhibitors such as, for example, those described in WO 2006/056399 can be used in combination with the treatment methods and regimens of the present disclosure for treatment of cancers and solid tumors. Other agents such as therapeutic antibodies can be used in combination with the treatment methods and regimens of the present disclosure for treatment of cancers and solid tumors. The one or more additional pharmaceutical agents can be administered to a patient simultaneously or sequentially.

The treatment methods as disclosed herein can be used in combination with one or more other enzyme/protein/receptor inhibitors therapies for the treatment of diseases, such as cancer and other diseases or disorders described herein. For example, the treatment methods and regimens of the present disclosure can be combined with one or more inhibitors of the following kinases for the treatment of cancer: Akt1, Akt2, Akt3, BCL2, CDK2, CDK4/6, TGF-βR, PKA, PKG, PKC, CaM-kinase, phosphorylase kinase, MEKK, ERK, MAPK, mTOR, EGFR, HER2, HER3, HER4, INS-R, IDH2, IGF-1R, IR-R, PDGFαR, PDGFβR, PI3K (alpha, beta, gamma, delta, and multiple or selective), CSF1R, KIT, FLK-II, KDR/FLK-1, FLK-4, flt-1, FGFR1, FGFR2, FGFR3, FGFR4, c-Met, PARP, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Non-limiting examples of inhibitors that can be combined with the treatment methods and regimens of the present disclosure for treatment of cancer include an FGFR inhibitor (FGFR1, FGFR2, FGFR3 or FGFR4, e.g., pemigatinib (INCY54828), INCB62079), an EGFR inhibitor (also known as ErB-1 or HER-1; e.g. erlotinib, gefitinib, vandetanib, orsimertinib, cetuximab, necitumumab, or panitumumab), a VEGFR inhibitor or pathway blocker (e.g. bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g. olaparib, rucaparib, veliparib or niraparib), a JAK inhibitor (JAK1 and/or JAK2, e.g., ruxolitinib, baricilinib, itacitinib (INCB39110), an LSD1 inhibitor (e.g., INCB59872 and INCB60003), a TDO inhibitor, a PI3K-delta inhibitor (e.g., INCB50465 and INCB50797), a PI3K-gamma inhibitor such as PI3K-gamma selective inhibitor, a Pim inhibitor (e.g., INCB53914), a CSF1R inhibitor, a TAM receptor tyrosine kinases (Tyro-3, Axl, and Mer), an adenosine receptor antagonist (e.g., A2a/A2b receptor antagonist), an HPK1 inhibitor, a chemokine receptor inhibitor (e.g. CCR2 or CCR5 inhibitor), a SHP1/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), c-MET inhibitors (e.g., capmatinib), an anti-CD19 antibody (e.g., tafasitamab), an ALK2 inhibitor (e.g., INCB00928); or combinations thereof.

In some embodiments, the treatment methods described herein are combined with administration of a PI3Kδ inhibitor. In some embodiments, the treatment methods described herein are combined with administration of a JAK inhibitor. In some embodiments, the treatment methods described herein are combined with administration of a JAK1 or JAK2 inhibitor (e.g., baricitinib or ruxolitinib). In some embodiments, the treatment methods described herein are combined with administration of a JAK1 inhibitor. In some embodiments, the treatment methods described herein are combined with administration of a JAK1 inhibitor, which is selective over JAK2.

Example antibodies that can be administered in combination therapy include, but are not limited to, trastuzumab (e.g., anti-HER2), ranibizumab (e.g., anti-VEGF-A), bevacizumab (AVASTIN™, e.g., anti-VEGF), panitumumab (e.g., anti-EGFR), cetuximab (e.g., anti-EGFR), rituxan (e.g., anti-CD20), and antibodies directed to c-MET.

One or more of the following agents may be administered to a patient in combination with the treatment methods of the present disclosure and are presented as a non-limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtreate, temozolomide, cyclophosphamide, SCH 66336, R115777, L778,123, BMS 214662, IRESSA™ (gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, Sm11, fludarabine, pentostatin, triapine, didox, trimidox, amidox, 3-AP, and MDL-101,731.

The treatment methods and regimens of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, bispecific or multi-specific antibody, antibody drug conjugate, adoptive T cell transfer, Toll receptor agonists, RIG-I agonists, oncolytic virotherapy and immunomodulating small molecules, including thalidomide or JAK1/2 inhibitor, PI3Kδ inhibitor and the like. The compounds can be administered in combination with one or more anti-cancer drugs, such as a chemotherapeutic agent. Examples of chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epacadostat, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, B1853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

Example suitable CDK4/6 inhibitors include palbociclib, ribociclib, trilaciclib, lerociclib, and abemaciclib, and their pharmaceutically acceptable salts. Other example suitable CDK4/6 inhibitors include compounds, and their pharmaceutically acceptable salts, as disclosed in WO 09/085185, WO 12/129344, WO 11/101409, WO 03/062236, WO 10/075074, and WO 12/061156.

In some embodiments, the compounds of the disclosure can be used in combination with one or more other kinase inhibitors including imatinib, particularly for treating patients resistant to imatinib or other kinase inhibitors.

In some embodiments, the treatment methods of the disclosure can be used in combination with a chemotherapeutic in the treatment of cancer, and may improve the treatment response as compared to the response to the chemotherapeutic agent alone, without exacerbation of its toxic effects. In some embodiments, the treatment methods of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining treatment methods of the present disclosure with an additional agent.

The agents can be combined with Compound 1 and/or antibody that binds to human PD-1 or human PD-L1, or antigen-binding fragment thereof, of the present treatment methods in a single or continuous dosage form, or the agents can be administered simultaneously or sequentially as separate dosage forms.

In some embodiments, a corticosteroid such as dexamethasone is administered to a patient in combination with the treatment methods of the disclosure where the dexamethasone is administered intermittently as opposed to continuously.

The treatment methods described herein can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

The treatment methods described herein can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the treatment methods and regimens of the present disclosure can be used in combination with tumor specific antigen such as heat shock proteins isolated from tumor tissue itself. In some embodiments, the treatment methods described herein can be combined with dendritic cells immunization to activate potent anti-tumor responses.

The treatment methods and regimens of the present disclosure can be used in combination with bispecific macrocyclic peptides that target Fe alpha or Fe gamma receptor-expressing effectors cells to tumor cells. The treatment methods and regimens of the present disclosure can also be combined with macrocyclic peptides that activate host immune responsiveness.

In some further embodiments, the treatment methods of the disclosure are combined with administration of other therapeutic agents to a patient prior to, during, and/or after a bone marrow transplant or stem cell transplant. The treatment methods and regimens of the present disclosure can be used in combination with bone marrow transplant for the treatment of a variety of tumors of hematopoietic origin.

When more than one pharmaceutical agents is administered to a patient, as discussed in any of the above embodiments, they can be administered simultaneously, separately, sequentially, or in combination (e.g., for more than two agents).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

II. Immune-Checkpoint Therapies

Compounds of the present disclosure (Compound 1, or a pharmaceutically acceptable salt thereof) can be used in combination with one or more immune checkpoint inhibitors for the treatment of diseases, such as cancer or infections. Exemplary immune checkpoint inhibitors include inhibitors against immune checkpoint molecules such as CBL-B, CD20, CD28, CD40, CD70, CD122, CD96, CD73, CD47, CDK2, GITR, CSF1R, JAK, PI3K delta, PI3K gamma, TAM, arginase, HPK1, CD137 (also known as 4-1BB), ICOS, A2AR, B7-H3, B7-H4, BTLA, CTLA-4, LAG3, TIM3, TLR (TLR7/8), TIGIT, CD112R, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the compounds provided herein can be used in combination with one or more agonists of immune checkpoint molecules, e.g., OX40, CD27, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1 or PD-L1, e.g., an anti-PD-1 or anti-PD-L1 monoclonal antibody. In some embodiments, the anti-PD-1 or anti-PD-L1 antibody is nivolumab, pembrolizumab, atezolizumab, durvalumab, avelumab, cemiplimab, atezolizumab, avelumab, tislelizumab, spartalizumab (PDR001), cetrelimab (JNJ-63723283), toripalimab (JS001), camrelizumab (SHR-1210), sintilimab (IBI308), AB122 (GLS-010), AMP-224, AMP-514/MEDI-0680, BMS936559, JTX-4014, BGB-108, SHR-1210, MEDI4736, FAZ053, BCD-100, KN035, CS1001, BAT1306, LZM009, AK105, HLX10, SHR-1316, CBT-502 (TQB2450), A167 (KL-A167), STI-A101 (ZKAB001), CK-301, BGB-A333, MSB-2311, HLX20, TSR-042, or LY3300054. In some embodiments, the inhibitor of PD-1 or PD-L1 is one disclosed in U.S. Pat. Nos. 7,488,802, 7,943,743, 8,008,449, 8,168,757, 8,217,149, or 10,308,644; U.S. Publ. Nos. 2017/0145025, 2017/0174671, 2017/0174679, 2017/0320875, 2017/0342060, 2017/0362253, 2018/0016260, 2018/0057486, 2018/0177784, 2018/0177870, 2018/0179179, 2018/0179201, 2018/0179202, 2018/0273519, 2019/0040082, 2019/0062345, 2019/0071439, 2019/0127467, 2019/0144439, 2019/0202824, 2019/0225601, 2019/0300524, or 2019/0345170; or PCT Pub. Nos. WO 03042402, WO 2008156712, WO 2010089411, WO 2010036959, WO 2011066342, WO 2011159877, WO 2011082400, or WO 2011161699, which are each incorporated herein by reference in their entirety. In some embodiments, the inhibitor of PD-L1 is INCB086550.

In some embodiments, the antibody is an anti-PD-1 antibody, e.g., an anti-PD-1 monoclonal antibody. In some embodiments, the anti-PD-1 antibody is nivolumab, pembrolizumab, cemiplimab, spartalizumab, camrelizumab, cetrelimab, toripalimab, sintilimab, AB122, AMP-224, JTX-4014, BGB-108, BCD-100, BAT1306, LZM009, AK105, HLX10, or TSR-042. In some embodiments, the anti-PD-1 antibody is nivolumab, pembrolizumab, cemiplimab, spartalizumab, camrelizumab, cetrelimab, toripalimab, or sintilimab. In some embodiments, the anti-PD-1 antibody is pembrolizumab. In some embodiments, the anti-PD-1 antibody is nivolumab. In some embodiments, the anti-PD-1 antibody is cemiplimab. In some embodiments, the anti-PD-1 antibody is spartalizumab. In some embodiments, the anti-PD-1 antibody is camrelizumab. In some embodiments, the anti-PD-1 antibody is cetrelimab. In some embodiments, the anti-PD-1 antibody is toripalimab. In some embodiments, the anti-PD-1 antibody is sintilimab. In some embodiments, the anti-PD-1 antibody is AB122. In some embodiments, the anti-PD-1 antibody is AMP-224. In some embodiments, the anti-PD-1 antibody is JTX-4014. In some embodiments, the anti-PD-1 antibody is BGB-108. In some embodiments, the anti-PD-1 antibody is BCD-100. In some embodiments, the anti-PD-1 antibody is BAT1306. In some embodiments, the anti-PD-1 antibody is LZM009. In some embodiments, the anti-PD-1 antibody is AK105. In some embodiments, the anti-PD-1 antibody is HLX10. In some embodiments, the anti-PD-1 antibody is TSR-042. In some embodiments, the anti-PD-1 monoclonal antibody is nivolumab or pembrolizumab. In some embodiments, the anti-PD1 antibody is SHR-1210. Other anti-cancer agent(s) include antibody therapeutics such as 4-1BB (e.g., urelumab, utomilumab). In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, avelumab, durvalumab, tislelizumab, BMS-935559, MEDI4736, atezolizumab (MPDL3280A; also known as RG7446), avelumab (MSB0010718C), FAZ053, KN035, CS1001, SHR-1316, CBT-502, A167, STI-A101, CK-301, BGB-A333, MSB-2311, HLX20, or LY3300054. In some embodiments, the anti-PD-L1 antibody is atezolizumab, avelumab, durvalumab, or tislelizumab. In some embodiments, the anti-PD-L1 antibody is atezolizumab. In some embodiments, the anti-PD-L1 antibody is avelumab. In some embodiments, the anti-PD-L1 antibody is durvalumab. In some embodiments, the anti-PD-L1 antibody is tislelizumab. In some embodiments, the anti-PD-L1 antibody is BMS-935559. In some embodiments, the anti-PD-L1 antibody is MEDI4736. In some embodiments, the anti-PD-L1 antibody is FAZ053. In some embodiments, the anti-PD-L1 antibody is KN035. In some embodiments, the anti-PD-L1 antibody is CS1001. In some embodiments, the anti-PD-L1 antibody is SHR-1316. In some embodiments, the anti-PD-L1 antibody is CBT-502. In some embodiments, the anti-PD-L1 antibody is A167. In some embodiments, the anti-PD-L1 antibody is STI-A101. In some embodiments, the anti-PD-L1 antibody is CK-301. In some embodiments, the anti-PD-L1 antibody is BGB-A333. In some embodiments, the anti-PD-L1 antibody is MSB-2311. In some embodiments, the anti-PD-L1 antibody is HLX20. In some embodiments, the anti-PD-L1 antibody is LY3300054.

In some embodiments, the inhibitor of an immune checkpoint molecule is a small molecule that binds to PD-L1, or a pharmaceutically acceptable salt thereof. In some embodiments, the inhibitor of an immune checkpoint molecule is a small molecule that binds to and internalizes PD-L1, or a pharmaceutically acceptable salt thereof. In some embodiments, the inhibitor of an immune checkpoint molecule is a compound selected from those in US 2018/0179201, US 2018/0179197, US 2018/0179179, US 2018/0179202, US 2018/0177784, US 2018/0177870, U.S. Ser. No. 16/369,654 (filed Mar. 29, 2019), and U.S. Ser. No. 62/688,164, or a pharmaceutically acceptable salt thereof, each of which is incorporated herein by reference in its entirety.

In some embodiments, the inhibitor of an immune checkpoint molecule is an inhibitor of KIR, TIGIT, LAIR1, CD160, 2B4 and TGFR beta.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, INCAGN2385, or eftilagimod alpha (IMP321).

In some embodiments, the inhibitor of an immune checkpoint molecule is an inhibitor of CD73. In some embodiments, the inhibitor of CD73 is oleclumab.

In some embodiments, the inhibitor of an immune checkpoint molecule is an inhibitor of TIGIT. In some embodiments, the inhibitor of TIGIT is OMP-31M32.

In some embodiments, the inhibitor of an immune checkpoint molecule is an inhibitor of VISTA. In some embodiments, the inhibitor of VISTA is JNJ-61610588 or CA-170.

In some embodiments, the inhibitor of an immune checkpoint molecule is an inhibitor of B7-H3. In some embodiments, the inhibitor of B7-H3 is enoblituzumab, MGD009, or 8H9.

In some embodiments, the inhibitor of an immune checkpoint molecule is an inhibitor of KIR. In some embodiments, the inhibitor of KIR is lirilumab or IPH4102.

In some embodiments, the inhibitor of an immune checkpoint molecule is an inhibitor of A2aR. In some embodiments, the inhibitor of A2aR is CPI-444.

In some embodiments, the inhibitor of an immune checkpoint molecule is an inhibitor of TGF-beta. In some embodiments, the inhibitor of TGF-beta is trabedersen, galusertinib, or M7824.

In some embodiments, the inhibitor of an immune checkpoint molecule is an inhibitor of PI3K-gamma. In some embodiments, the inhibitor of PI3K-gamma is IPI-549.

In some embodiments, the inhibitor of an immune checkpoint molecule is an inhibitor of CD47. In some embodiments, the inhibitor of CD47 is Hu5F9-G4 or TTI-621.

In some embodiments, the inhibitor of an immune checkpoint molecule is an inhibitor of CD73. In some embodiments, the inhibitor of CD73 is MEDI9447.

In some embodiments, the inhibitor of an immune checkpoint molecule is an inhibitor of CD70. In some embodiments, the inhibitor of CD70 is cusatuzumab or BMS-936561.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the agonist of an immune checkpoint molecule is an agonist of OX40, CD27, CD28, GITR, ICOS, CD40, TLR7/8, and CD137 (also known as 4-1BB).

In some embodiments, the agonist of CD137 is urelumab. In some embodiments, the agonist of CD137 is utomilumab.

In some embodiments, the agonist of an immune checkpoint molecule is an inhibitor of GITR. In some embodiments, the agonist of GITR is TRX518, MK-4166, INCAGN1876, MK-1248, AMG228, BMS-986156, GWN323, MEDI1873, or MEDI6469. In some embodiments, the agonist of an immune checkpoint molecule is an agonist of OX40, e.g., OX40 agonist antibody or OX40L fusion protein. In some embodiments, the anti-OX40 antibody is INCAGN01949, MEDI0562 (tavolimab), MOXR-0916, PF-04518600, GSK3174998, BMS-986178, or 9B12. In some embodiments, the OX40L fusion protein is MEDI6383.

In some embodiments, the agonist of an immune checkpoint molecule is an agonist of CD40. In some embodiments, the agonist of CD40 is CP-870893, ADC-1013, CDX-1140, SEA-CD40, RO7009789, JNJ-64457107, APX-005M, or Chi Lob 7/4.

In some embodiments, the agonist of an immune checkpoint molecule is an agonist of ICOS. In some embodiments, the agonist of ICOS is GSK-3359609, JTX-2011, or MEDI-570.

In some embodiments, the agonist of an immune checkpoint molecule is an agonist of CD28. In some embodiments, the agonist of CD28 is theralizumab.

In some embodiments, the agonist of an immune checkpoint molecule is an agonist of CD27. In some embodiments, the agonist of CD27 is varlilumab.

In some embodiments, the agonist of an immune checkpoint molecule is an agonist of TLR7/8. In some embodiments, the agonist of TLR7/8 is MEDI9197.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK104.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196. Inhibitors of arginase inhibitors include INCB1158.

As provided throughout, the additional compounds, inhibitors, agents, etc. can be combined with the present compound in a single or continuous dosage form, or they can be administered simultaneously or sequentially as separate dosage forms.

Pharmaceutical Compositions

In some embodiments, Compound 1, or a pharmaceutically acceptable salt thereof, can be formulated as part of a pharmaceutical composition. In some embodiments, the antibody that binds to human PD-1 or human PD-L1 can be formulated as part of a pharmaceutical composition. The pharmaceutical compositions comprising the compound, and the antibody that binds to human PD-1 or human PD-L1 or antigen-binding fragment thereof described herein can be formulated as pharmaceutical compositions for administration to a subject, e.g., to treat a disorder described herein. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge, S. M., et al. (1977) *J. Pharm. Sci.* 66:1-19).

Pharmaceutical formulation is a well-established art, and is further described, e.g., in Gennaro (ed.), *Remington: The Science and Practice of Pharmacy*, 20th ed., Lippincott, Williams & Wilkins (2000) (ISBN: 0683306472); Ansel et al., *Pharmaceutical Dosage Forms and Drug Delivery Systems*, 7th Ed., Lippincott Williams & Wilkins Publishers (1999) (ISBN: 0683305727); and Kibbe (ed.), *Handbook of Pharmaceutical Excipients American Pharmaceutical Association*, 3rd ed. (2000) (ISBN: 091733096X).

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. Typically compositions for the agents described herein are in the form of injectable or infusible solutions.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the antibody that binds to human PD-1 or human PD-L1, or antigen-binding fragment thereof, may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., *Sustained and Controlled Release Drug Delivery Systems*, J. R. Robinson, ed., Marcel Dekker, Inc., New York (1978).

In some embodiments, the compound is formulated as part of a pharmaceutical composition, further comprising at least one excipient.

In some embodiments, in making the compositions provided herein, the compound is mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In some embodiments, the pharmaceutical compositions described herein is in the form of tablets.

In preparing a formulation, the compound can be milled to provide the appropriate particle size prior to combining with the other ingredients. In some embodiments, the compound can be milled to a particle size of less than 200 mesh. In some embodiments, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions provided herein can be formulated so as to provide quick, sustained or delayed release of the active ingredient after administration to the patient by employing procedures known in the art.

The compositions can be formulated in a unit dosage form. The term "unit dosage forms" refers to physically discrete units suitable as unitary dosages for human subjects and other mammals, each unit containing a predetermined quantity of the compound calculated to produce the desired therapeutic effect (e.g., the desired PK profile), in association with a suitable pharmaceutical excipient.

In certain embodiments, for preparing solid compositions such as tablets, the compound is mixed with a pharmaceutical excipient to form a solid pre-formulation composition containing a homogeneous mixture of the compound. When referring to these pre-formulation compositions as homogeneous, the compound is typically dispersed evenly throughout the composition so that the composition can be readily subdivided into equally effective unit dosage forms such as tablets, pills and capsules. This solid pre-formulation is then subdivided into unit dosage forms.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions described herein can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

In some embodiments, compositions described herein are sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

In some embodiments, Compound 1 is administered orally. In some embodiments, Compound 1 is administered as an oral capsule.

In some embodiments, Compound 1 is administered once daily.

In some embodiments, Compound 1 is administered in a daily dose of about 5 mg to about 150 mg. In some embodiments, Compound 1 is administered in a daily dose of about 5 mg to about 120 mg. In some embodiments, Compound 1 is administered in a daily dose of about 5 mg to about 100 mg. In some embodiments, Compound 1 is administered in a daily dose of about 5 mg to about 80 mg. In some embodiments, Compound 1 is administered in a daily dose of about 5 mg to about 60 mg. In some embodiments, Compound 1 is administered in a daily dose of about 5 mg to about 40 mg. In some embodiments, Compound 1 is administered in a daily dose of about 5 mg to about 20 mg. In some embodiments, Compound 1 is administered in a daily dose of about 5 mg to about 10 mg. In some embodiments, Compound 1 is administered in a daily dose of about 10 mg to about 150 mg. In some embodiments, Compound 1 is administered in a daily dose of about 10 mg to about 120 mg. In some embodiments, Compound 1 is administered in a daily dose of about 10 mg to about 100 mg. In some embodiments, Compound 1 is administered in a daily dose of about 10 mg to about 80 mg. In some embodiments, Compound 1 is administered in a daily dose of about 10 mg to about 60 mg. In some embodiments, Compound 1 is administered in a daily dose of about 10 mg to about 40 mg. In some embodiments, Compound 1 is administered in a daily dose of about 10 mg to about 20 mg. In some embodiments, Compound 1 is administered in a daily dose of about 5 mg, about 10 mg, about 15 mg, about 20 mg, about 30 mg, about 45 mg, about 60 mg, about 90 mg, or about 120 mg.

In some embodiments, Compound 1 is administered once daily in a continuous dosing regimen. In some embodiments, Compound 1 is administered in a 28-day dosing regimen.

In some embodiments, retifanlimab is administered intravenously.

In some embodiments, retifanlimab is administered once monthly. In some embodiments, retifanlimab is administered once every four weeks.

In some embodiments, retifanlimab is administered in a dose of about 250 mg to about 1000 mg. In some embodiments, retifanlimab is administered in a dose of about 400 mg to about 600 mg. In some embodiments, retifanlimab is administered in a dose of about 500 mg.

Labeled Compound

Another aspect of the present disclosure relates to labeled Compound 1 (radio-labeled, fluorescent-labeled, isotopically-labeled, etc.) that would be useful not only in imaging techniques but also in assays, both in vitro and in vivo.

The present disclosure further includes isotopically-labeled Compound 1. An "isotopically" or "radio-labeled" compound is Compound 1, where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms can be optionally substituted with deuterium atoms.

One or more constituent atoms of Compound 1 can be replaced or substituted with isotopes of the atoms in natural or non-natural abundance. In some embodiments, Compound 1 includes at least one deuterium atom. For example, one or more hydrogen atoms in a compound presented herein can be replaced or substituted by deuterium. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et al. J. Med Chem. 2011, 54, 201-210; R. Xu et al. J. Label Compd. Radiopharm. 2015, 58, 308-312). In particular, substitution at one or more metabolism sites may afford one or more of the therapeutic advantages.

It is understood that a "radio-labeled" or "labeled compound" is a compound that has incorporated at least one radionuclide. In some embodiments, the radionuclide is selected from the group consisting of $^3$H and $^{14}$C. In some embodiments, the radionuclide is selected from the group consisting of $^{11}$C, $^{18}$F, $^{75}$Br, $^{76}$Br, and $^{77}$Br.

Kits

The present disclosure also includes pharmaceutical kits useful, for example, in the treatment cancers referred to herein, which include one or more containers containing a pharmaceutical composition described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.
General Methods H1299 cells (RRID: CVCL_0060) were maintained in RPMI-1640 (RPMI, ThermoFisher Scientific, Carlsbad, Calif.; #11875-093) culture medium with 10% fetal bovine serum (FBS; GE Healthcare; #SH30071.03) and obtained from American Type Culture Collection (ATCC; #CRL-5803). BAF3 cells were obtained from German Collection of Microorganisms and Cell Cultures (DSMZ; Braunschweig, Germany; #ACC 300) and grown in RPMI supplemented with 10% FBS plus 4 ng/mL interleukin (IL)-3. G361 cells (RRID: CVCL_1220) were obtained from ATCC (#CRL-1424) and maintained in RPMI medium containing 10% FBS. All human cell lines have been authenticated using short tandem repeat profiling within the last 3 years. All experiments were performed with *mycoplasma*-free cells. Retifanlimab was provided by Incyte and is an anti-human programmed cell death (PD)-1 antibody. Human peripheral blood mononuclear cells (PBMCs) were obtained from normal leukapheresis of two healthy donors (Biological Specialties, Colmar, Pa.).

Example A. Biochemical Assay

The biochemical potency of Compound 1 to inhibit the enzymatic activity of TAM family members was investigated by TR-FRET assays using recombinant phosphorylated forms of the kinase domains for AXL, MER and TYRO3.

Phospho-AXL (pAXL), cMER and Tyro3 kinase activities were measured by time-resolved fluorescence energy transfer (TR-FRET) assays. Autophosphorylation of AXL was carried out before the kinase assay by incubating the recombinant AXL protein (ThermoFisher Scientific; #PV4275) in buffer containing 50 mM Tris, pH 7.5, 0.2 mg/mL AXL, 5 mM ATP, 20 mM $MgCl_2$ and 2 mM dithiothreitol (DTT) at room temperature for 1 hour. The kinase assay buffer contained 50 mM HEPES, pH 7.5, 10 mM $MgCl_2$, 1 mM EGTA, 0.01% NP-40 and 2 mM DTT. Enzyme solutions of 0.69 nM phospho-AXL, or 0.088 nM cMER (Carna Biosciences, Kobe, Japan; #08-108) or 0.137 nM TYRO3 (Life Technologies, PR7480A) were prepared in assay buffer. A 1-mM stock solution of peptide substrate Biotin-EQEDEPEGDYFEWLE-amide (Quality Controlled Biochemicals, Hopkinton, Mass.) dissolved in dimethyl sulfoxide (DMSO) was diluted to 1 µM in assay buffer containing 2000 µM ATP. Compound 1 (15 nL) was dissolved in DMSO and transferred from compound plates to low-volume white 384-well assay plates (Perkin Elmer ProxiPlate, Waltham, Mass.). Enzyme solution (6 µL; or assay buffer for the enzyme blank) was added to the appropriate wells in each plate and incubated for 30 minutes. Then, 6 µL/well substrate solution was added to initiate the reaction. The plate was protected from light and incubated at room temperature (21° C.) for 60 minutes (cMER and TYRO3) or 90 minutes (AXL). The reaction was stopped by adding 6-4, detection solution containing 50 mM Tris-HCl, pH 7.8, 150 mM NaCl, 0.05% bovine serum albumin (BSA), 45 mM EDTA, 180 nM SA-APC (Perkin Elmer; CR130-100) and 3 nM Eu-W1024 anti-phosphotyrosine PY20 (Perkin Elmer; AD0067). The plate was incubated for 30 minutes at room temperature, and homogenous time resolved fluorescence (HTRF) signal was measured on a PheraStar FS plate reader (BMG Labtech, Ortenberg, Germany). Percent inhibition was calculated for each concentration, and half maximal inhibitory concentration ($IC_{50}$) value was generated from curve fitting with GraphPad Prism software (San Diego, Calif.).

Compound reversibility was determined by measuring the recovery of cMER enzymatic activity after a rapid and large dilution of the cMER-inhibitor complex. cMER, ATP, and biotin-labeled peptide substrate were diluted in kinase assay buffer containing 50 mM HEPES, pH 7.5, 10 mM MgCl2, 1 mM EGTA, 0.01% NP-40, and 2 mM DTT. Detection reagents (240 nM SA-APC [Perkin Elmer; CR130-100] and 4 nM Eu-W1024 anti-phosphotyrosine PY20 [Perkin Elmer; AD0067]) were prepared in detection buffer containing 50 mM Tris-HCl, pH 7.8, 150 mM NaCl, 0.05% BSA, and 45 mM EDTA. To identify the inhibition mode of compounds, $IC_{50}$ values were measured at different ATP concentrations (25, 100, 300, and 1000 μM final concentrations in reaction). Compound 1 was incubated with ATP and enzyme (66 pM cMER) in 8-4, assay buffer for an extended time (2 hours). Under these conditions, equilibrium among compounds, ATP, and enzyme was reached before reaction was started by addition of 4 μL of 1.5-μM biotin-labeled peptide. After 1 hour of incubation, the reaction was stopped by 4-4, detection reagent containing 60 mM EDTA, 240 nM SA-APC (Perkin Elmer; CR130-100), and 4 nM Eu-W1024 anti-phosphotyrosine PY20 (Perkin Elmer; #AD0067). Assay plates were read in HTRF mode by PheraStar plate reader after 30 minutes of incubation. Dose-response curves were fitted and $IC_{50}$ values were plotted as a function of ATP concentrations. The inhibitory constant ($K_i$) for Compound 1 was calculated by fitting the data to the equation for competitive inhibition ($IC_{50}=K_i (1+[ATP]/Km)$).

The average $IC_{50}$ values from multiple lots of Compound 1 against AXL, MER and TYRO3 were 0.61±0.31 nM (n=18), 3.17±1.97 nM (n=25), and 101±27 nM (n=25), respectively, demonstrating approximately 30-fold selectivity over TYRO3. Compound 1 was also evaluated at 200 nM in a comprehensive kinase study, which included 179 kinases. Compound 1 was approximately 60-fold selective for AXL and MER compared to c-Met and did not inhibit any other kinases. These results demonstrate that Compound 1 is a potent and highly selective inhibitor of AXL and MER kinases. The mode of inhibition with respect to ATP concentration was evaluated using a MER kinase assay. As shown in FIG. 1, the $IC_{50}$ values of Compound 1 for MER kinase increased linearly with ATP concentration, indicating an ATP-competitive mode of inhibition.

Example B. Cell Proliferation Assays

To evaluate the cellular potency and selectivity within the TAM receptor family, mouse BAF3 cell lines with stable expression of AXL, MER, or TYRO3 were generated.

The cytoplasmic domain of AXL, MER, or TYRO3 fused with dimerization sequence and HA tag was cloned into a pMSCV (murine stem cell virus) vector with a puromycin-resistance marker to generate three constructs individually by electroporation into BAF3 cells. Single clones that were IL-3-independent and puromycin-resistant were selected and characterized. To evaluate effects on BAF3 cell proliferation, 1000 cells/well of BAF3, BAF3-AXL, BAF3 MER, or BAF3-TYRO3 cells were treated in the presence or absence of Compound 1 at various concentrations (10 concentration points with a three-fold dilution factor from the highest concentration of 10 μM) diluted in RPMI-1640 with 2% FBS for 48 hours in a 384-well plate. Cell viability was measured by ATP assay (CellTiter-Glo Assay, Promega, Madison, Wis.) according to the manufacturer's procedure. The data were converted to percent inhibition relative to DMSO control, and $IC_{50}$ curves were fitted using GraphPad Prism software.

Treatment of stable BAF3 transfectants with Compound 1 potently inhibited the proliferation of BAF3 cells expressing either AXL or MER kinase with concentration required for 50% growth inhibition ($GI_{50}$) values of 16±11 nM and 14±4.9 nM, respectively, but weakly inhibited the growth of TYRO3-expressing BAF3 cells ($IC_{50}$=498±161 nM) and was inactive against parental BAF3 cells ($IC_{50}$>4000 nM). These cellular data are consistent with the biochemical data and confirm that Compound 1 is a potent inhibitor of AXL and MER and is >30-fold selective against TYRO3.

Example C. pAXL Inhibition Assay in H1299 Cells

The ability of Compound 1 to modulate AXL activity was evaluated in tumor cell lines expressing high levels of endogenous AXL. The non-small cell lung cancer cell line H1299 has been shown to exhibit markedly increased AXL protein expression.

H1299 cells were plated (30,000 cells/well) in 96-well tissue-culture plates (Costar, Corning Incorporated, Corning, N.Y.) and incubated overnight at 37° C. with 5% $CO_2$. Compound 1 at an appropriate concentration was added and incubated for 1 hour at 37° C. with 5% $CO_2$. rhGAS6 (R&D Systems, Minneapolis, Minn.; #885-GSB) was added at 1 μg/mL to each well, and plates were incubated at 37° C. with 5% $CO_2$ for 15 minutes. Cells were harvested and lysed in 110 μL of ice-cold lysis buffer (Cell Signaling Technology, Danvers, Mass.; #9803) with protease and phosphatase inhibitors (ThermoFisher Scientific; #78446) for 1 hour on ice and stored at −80° C. for ELISA. ELISA plates were prepared by incubating Greiner lumitrac high-binding plates with 8 μg/mL of anti-AXL antibody (R&D Systems; MAB154) overnight at room temperature. The plates were washed and blocked with phosphate buffered saline (PBS) with 0.1% BSA. Cell lysates were loaded onto ELISA plates and incubated 2 hours at room temperature. The plates were washed and incubated with LANCE Eu-W1024 anti-phosphotyrosine antibody (Perkin Elmer; #AD0067) in DELFIA assay buffer (Perkin Elmer; #4002-0010) for 2 hours at room temperature, washed, and DELFIA Enhancement Solution (Perkin Elmer; #4001-0010) was added. The plates were gently shaken for 15 minutes at room temperature and read on the PheraStar (BMG Labtech). The data were converted to percent inhibition relative to DMSO control, and Compound 1 $IC_{50}$ determination was performed by fitting the curve of percent inhibition versus the log of the inhibitor concentration using GraphPad Prism.

Figure 2:
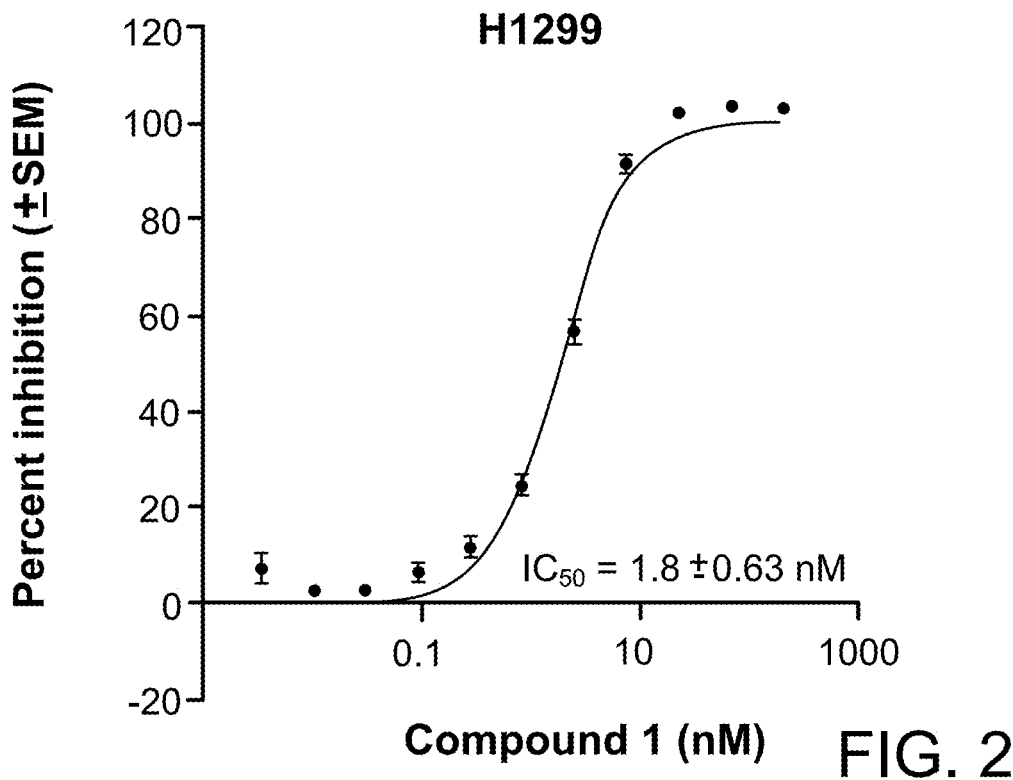
FIG. 2 is a plot of percent inhibition of phosphor-AXL (pAXL) for Compound 1 in H1299 cells.

Compound 1 treatment of H1299 cells potently inhibited pAXL with an $IC_{50}$ value of 1.8±0.63 nM (N=19), as shown in FIG. 2.

Example D. Phospho-MER Inhibition Assay in G361 Cells

The potency of Compound 1 in blocking MER autophosphorylation was evaluated in G361 cells, a melanoma cell line expressing high level of MER kinase.

Newly thawed G361 cells were allowed to recover for three passages before use, and only cells within 20 passages after thawing were used in the assay. Cells were kept under nonconfluent conditions and used in log-phase growth. Two mL of 1×10^6 cells/mL (2×10^6 cells/well) G361 cells were added to a six-well tissue-culture plates (Corning Incorporated; #3961) for 2 days. At the time of the assay, 1 mL of medium was added to each well. To determine the activity of Compound 1, a stock solution of 5 mM Compound 1 in DMSO was used to make three-fold serial dilution of DMSO working stocks that were further diluted in culture medium, and 100 μL of the diluted compound was added to each well with final concentrations ranging from 0.2 nM to 1 μM. For control wells in the absence of Compound 1, 100 μL of 0.22% DMSO was added to maintain the final 0.02% DMSO concentration in every sample. The mixtures of cells and compound were incubated for 1 hour at 37° C. in a humidified incubator supplemented with 5% $CO_2$, then 10 μL of 55.5 µg/mL of MER-activating antibody (R&D Systems; #MAB8912; final concentration equal to 500 ng/mL) in PBS was added to each well, except the unstimulated sample, and incubated for 30 minutes at 37° C. in a humidified incubator supplemented with 5% $CO_2$. After incubation, each well was washed twice with 2 mL of cold PBS. Lysis buffer (120 µL; Cell Signaling Technology; #9803) containing 1 mM PMSF, Halt phosphatase inhibitors (1:100 dilution; ThermoFisher Scientific; #78426) and protease inhibitors (1:50 dilution; Cal Biochem® #535140; MilliporeSigma, Burlington, Mass.) was added to each sample and incubated on ice for 30 minutes. The cell extracts were transferred to a 96-well V bottom plate, centrifuged at 3000 rpm for 10 minutes at 4° C. and the extracts were stored at 80° C. until analysis by ELISA for phospho-MER (pMer; R&D Systems; #DYC2579). The optical density of the plate was measured using a Molecular Devices SpectraMax Plus microplate reader (Molecular Devices, San Jose, Calif.) at 450 nm with wavelength correction at 540 nm. Absorbance of the standards was plotted versus the concentration to generate a standard curve using four-parameter algorithm curve fitting software (SOFTmax PRO application, Molecular Devices). pMER concentrations for unknown samples were determined by extrapolation from the standard curve. $IC_{50}$ values were calculated by GraphPad Prism 7.0 using a nonlinear regression sigmoidal dose-response curve with variable slope.

Figure 3:
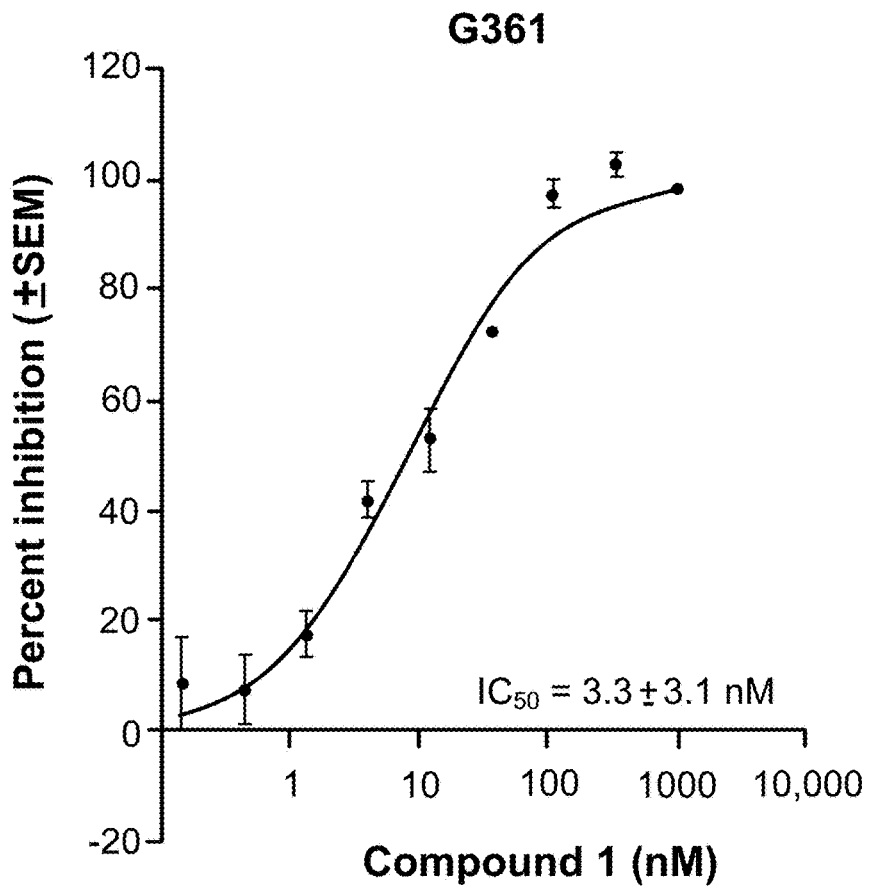
FIG. 3 is a plot of percent inhibition of phosphor-MER (pMER) for Compound 1 in G361 melanoma cells.

As shown in FIG. 3, Compound 1 effectively blocked MER phosphorylation induced by MAB8912 in G361 melanoma cells with an $IC_{50}$ value of 8.3±3.1 nM (N=2).

Example E. Inhibition of MER Kinase Activity in Primary Macrophages

The ability of Compound 1 to modulate the activity of MER kinase in macrophages was evaluated.

Human peripheral blood mononuclear cells (PBMCs) were separated using Ficoll-Paque density gradient centrifugation and any remaining red blood cells (RBC) were lysed using 1×RBC Lysis Buffer (Cell Signaling Technology) for 5 minutes at room temperature. The PBMCs were washed with PBS before being enriched for monocytes using CD14 microbeads positive selection separation following the manufacturer's protocol as specified (AutoMacs Pro, Miltenyi Biotec, Bergisch Gladbach, Germany). The $CD14^+$ cells were initially seeded at $1.5×10^6$ per well in six-well plates in RPMI-1640+10% heat-inactivated FBS and 10% AB human serum (Sigma-Aldrich Corp., St Louis, Mo.), 100 U/mL penicillin+100 µg/mL streptomycin (Corning), supplemented with 100 ng/mL macrophage colony-stimulating factor (M-CSF; R&D Systems; #216-MC) and were cultured at 37° C., 5% $CO_2$ for 10 days. Fresh M-CSF was added to the media every 3 days until the macrophages had attached. In preparation for the assay, the media was removed and the cells were re-fed with fresh media without human serum. Compound 1 stocks were prepared at 1000× in 100% DMSO and diluted 67-fold first into media and then a further 15-fold when added to the macrophages. The macrophages were treated with Compound 1 for 2 hours at 37° C., 5% $CO_2$. Five µg/mL anti-MER antibody MAB8912 (R&D Systems) was added to the macrophages for an additional 30 minutes, at which time the cells were washed with cold PBS. All PBS was carefully aspirated from the wells and the dry plates were frozen at −20° C.

Macrophages were allowed to thaw on ice before being lysed with 250 µL/well of 1× Lysis Buffer (Cell Signaling Technology; #9803) and Halt protease and phosphatase inhibitors (ThermoFisher Scientific) for 1 hour at 4° C. The lysed cells were scraped and transferred to an Eppendorf vial on ice. The lysates were centrifuged at 12,700 rpm for 15 minutes at 4° C. PDX tumors were weighed and homogenized with lysis buffer supplemented with protease and phosphatase inhibitor cocktails (Roche, Basel, Switzerland; #11836170001). Tumors were lysed on ice for 30 minutes, followed by centrifugation at 13,000 rpm for 10 minutes. Protein lysates were quantified using BCA Protein Assay Kit (Pierce, ThermoFisher Scientific; #23225). Lysates were transferred to a new tube together with 6× Laemmli SDS sample buffer (Alfa Aesar, Haverhill, Mass.) and the samples were heated for 6 minutes at 95° C. Approximately 50 µg of protein sample was loaded per well using Novex™ 8-16% Tris-Glycine Mini Gels or 4-12% Tris-Glycine Novex WedgeGels (Invitrogen, Carlsbad, Calif.). The proteins were transferred to a nitrocellulose membrane using an iBlot (ThermoFisher Scientific) dry blotting system. The membranes were blocked with 0.5% nonfat dry milk in wash buffer (100 mM NaCl, 10 mM Tris-HCl, pH 8.0, 0.1% Tween 20) for 1 hour at room temperature. The primary antibody used for pMER was from PhosphoSolutions (Aurora, Colo.; #p186-749). The remaining antibodies were obtained from Cell Signaling Technology: MER (#4319), pAXL (#5724), AXL, (#4566), GAS6 (#67202), pAKT (#4060), AKT (#9272), and β-Actin (#4970). Primary antibodies were added at 1:500 and 1:1000, respectively, in 0.5% milk/wash buffer and rocked overnight at 4° C. The membranes were washed three times in wash buffer before incubation with the secondary antibody (anti-rabbit IgG1-HRP; Cell Signaling Technology) at 1:2500 in 0.5% milk/wash buffer for 2 hours at room temperature. The membranes were washed again before the bands were detected with SuperSignal West Dura Extended Duration Chemiluminescent substrate (ThermoFisher Scientific) and were visualized using the Fluorochem M Digital Imager (Protein Simple, San Jose, Calif.).

Figure 4:
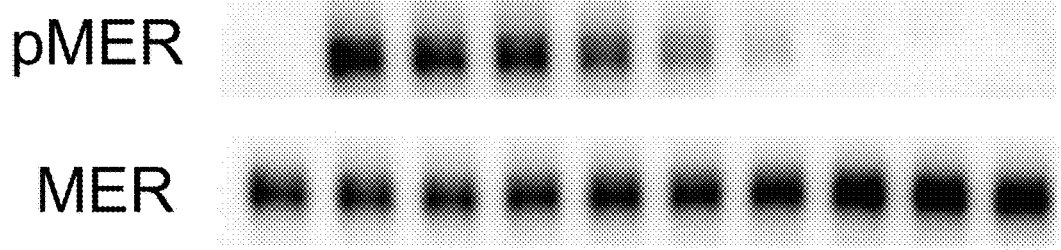
FIG. 4 is a Western blot of pMER and total MER in primary macrophages differentiated in vitro from human peripheral blood mononuclear cells (PBMCs) pretreated for 2 hours with Compound 1 followed by stimulation with the MER-specific agonist antibody MAB8912.

Compound 1 was able to inhibit pMER in primary macrophages in a concentration-dependent manner with an $IC_{50}$ of 1.6±0.4 nM (N=2), as shown in FIG. 4. These data suggest that Compound 1 can inhibit MER kinase activity in both tumor and primary human immune cells.

Example F. Macrophage Suppression of T-Cell Proliferation Assay

To examine the functional activity of Compound 1, the effects on macrophage-mediated suppression of T-cell proliferation were evaluated.

Human PBMCs were isolated from the peripheral blood of healthy donors by density gradient centrifugation on Ficoll-Hypaque (GE Healthcare, Chicago, Ill.; #17-1440-02) followed by purification with anti-CD14 Microbeads (Miltenyi Biotec; #130-050-201). Isolated $CD14^+$ monocytes/macrophages were incubated with 100 ng/mL M-CSF (R&D Systems; #216-MC) and 50 ng/mL TGFβ1 (R&D Systems; #240-B) at 37° C. for 6 days; 100 µL/well of $CD14^+$ macrophages were seeded at $0.5×10^6$ cells/mL in a 96-well round-bottomed culture plate (Costar; #3799) and treated with Compound 1 overnight at 37° C. $CD4^+CD25^-$ effector T ($T_{eff}$) cells were isolated using the Dynabeads regulatory $CD4^+CD25^+$ T-cell kit (Life Technologies; #11363D) and the $T_{eff}$ cells were labeled with carboxyfluorescein succinimidyl ester (CFSE) using the CellTrace CFSE Cell Proliferation kit (ThermoFisher Scientific; #C34554). Freshly CFSE-labeled $T_{eff}$ cells were mixed with Dynabeads Human T-Activator CD3/CD28 (ThermoFisher Scientific; #11132D) at a ratio of 5:1, then 100 µL/well of the T cells/beads mixture at 1×10⁶ cells/mL were added to the Compound 1-treated CD14⁺ macrophages and continue to culture at 37° C. for 5 days. $T_{eff}$ cells were analyzed by a flow cytometer (BD LSRFortessa X-20, BD Biosciences, San Jose, Calif.) and the cell-free supernatant was tested in the Luminex assay (Millipore; #HCYTOMAG-60K_38plex) to measure the concentrations of different cytokines and chemokines.

Figure 5A:
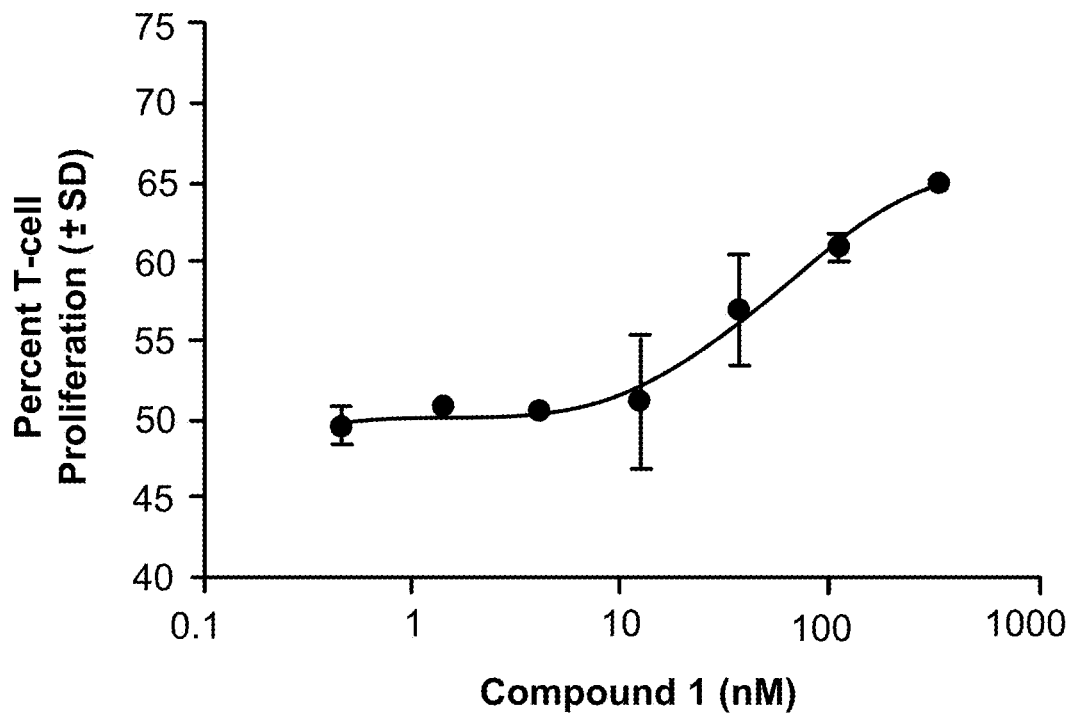
FIG. 5A is a plot of T-cell proliferation in primary macrophages differentiated in vitro from human peripheral blood mononuclear cells (PBMCs) pretreated with Compound 1.
Figure 5B:
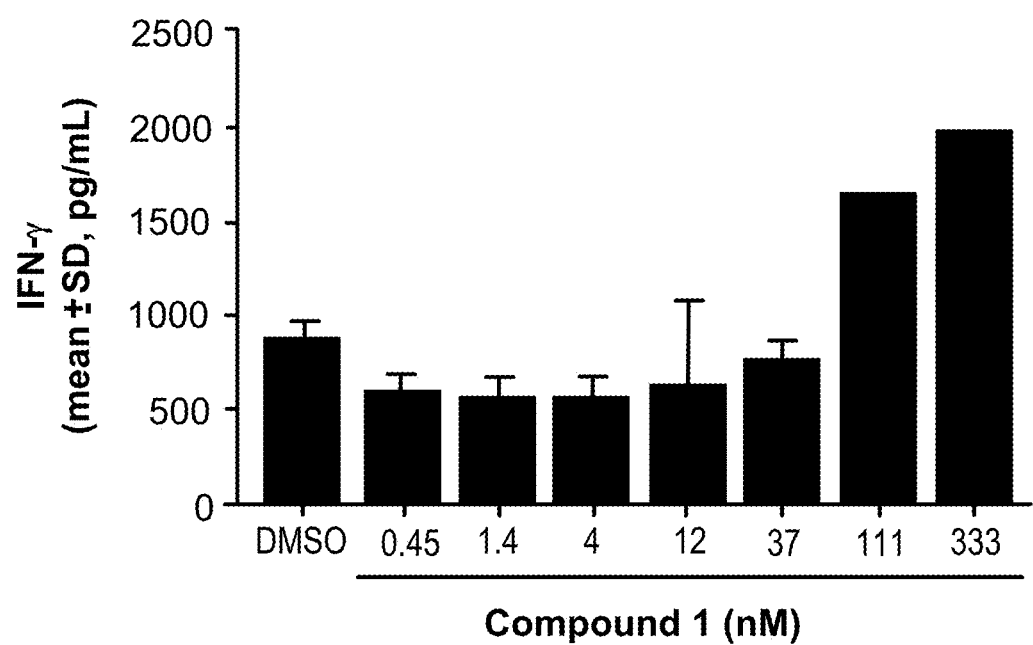
FIG. 5B is a plot of IFN-γ production in primary macrophages differentiated in vitro from human PBMCs pretreated with Compound 1.

FIG. 5A demonstrates that Compound 1 partially reversed macrophage-mediated suppression of T-cell proliferation. This was associated with an increase in IFN-γ production, as shown in FIG. 5B.

Example G. PBMC Cell Co-Culture Assay

The ability of Compound 1 to cooperate with checkpoint blockade to further boost antitumor responses was evaluated. H1299 lung cancer cells were co-cultured with stimulated human PBMCs treated with Compound 1, anti-human programmed cell death (PD)-1 antibody retifanlimab or the combination, and production of proinflammatory cytokines was assessed in two different experiments (FIG. 6). A third experiment was conducted, which confirmed these results (not shown).

H1299 cells were co-cultured with human PBMCs, each at 4 or 16×10⁴ cells/mL in RPMI containing 10% FBS, 100 U/mL of penicillin-streptomycin (ThermoFisher Scientific; #15140-122) and 1× beta-mercaptoethanol (ThermoFisher Scientific; #21985-023). Compound 1 or retifanlimab were added as single agents or in combination to the cells. Anti-CD3 (BD Biosciences #555336), anti-CD28 (BD Biosciences #555725) or SEA (Toxin Technology, Sarasota, Fla.; #AT101red) were added at a final concentration of 1 µg/mL, 0.5 µg/mL or 100 ng/mL, respectively, to stimulate cell growth. Cultures were incubated at 37° C. in 5% $CO_2$ incubator for 4 days. The supernatant was collected for cytokine analysis using a multiplex assay system (custom human ProcartaPlex Luminex kit, ThermoFisher Scientific; #PPX-15-MXRWE6P).

Figure 6A:
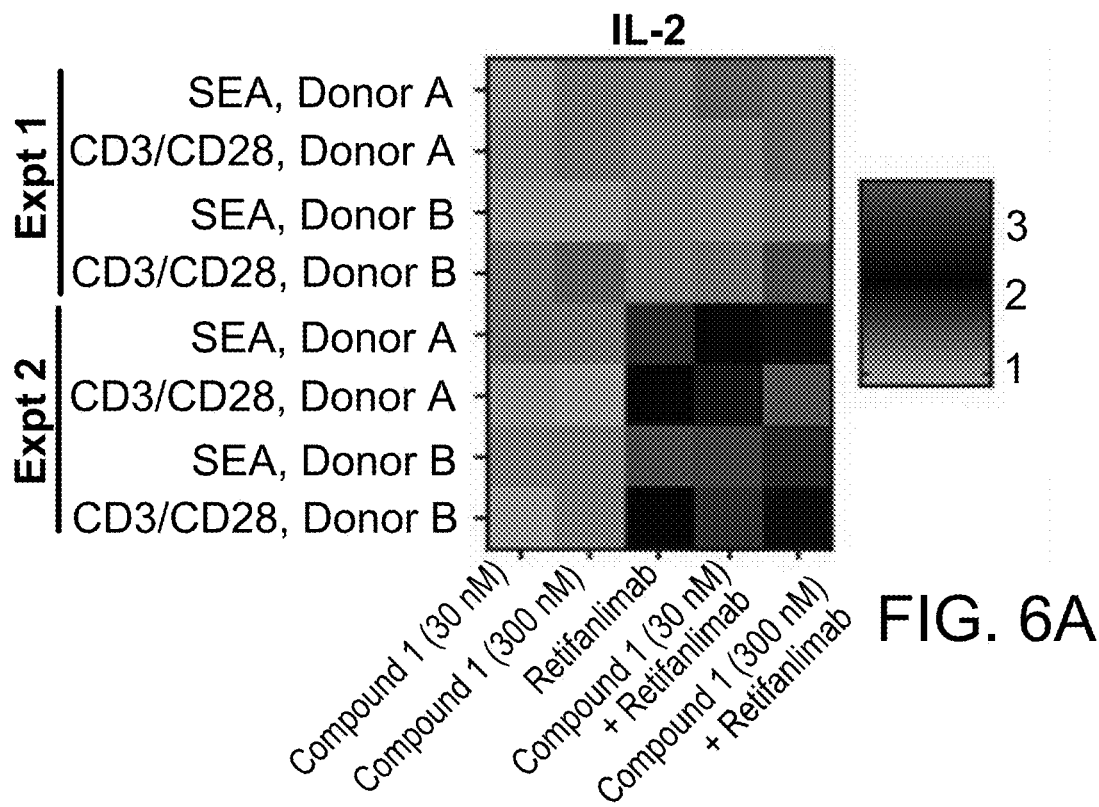
FIG. 6A is a heatmap showing the in vitro induction of Interleukin (IL)-2 by Compound 1 and/or retifanlimab in PBMCs.
Figure 6B:
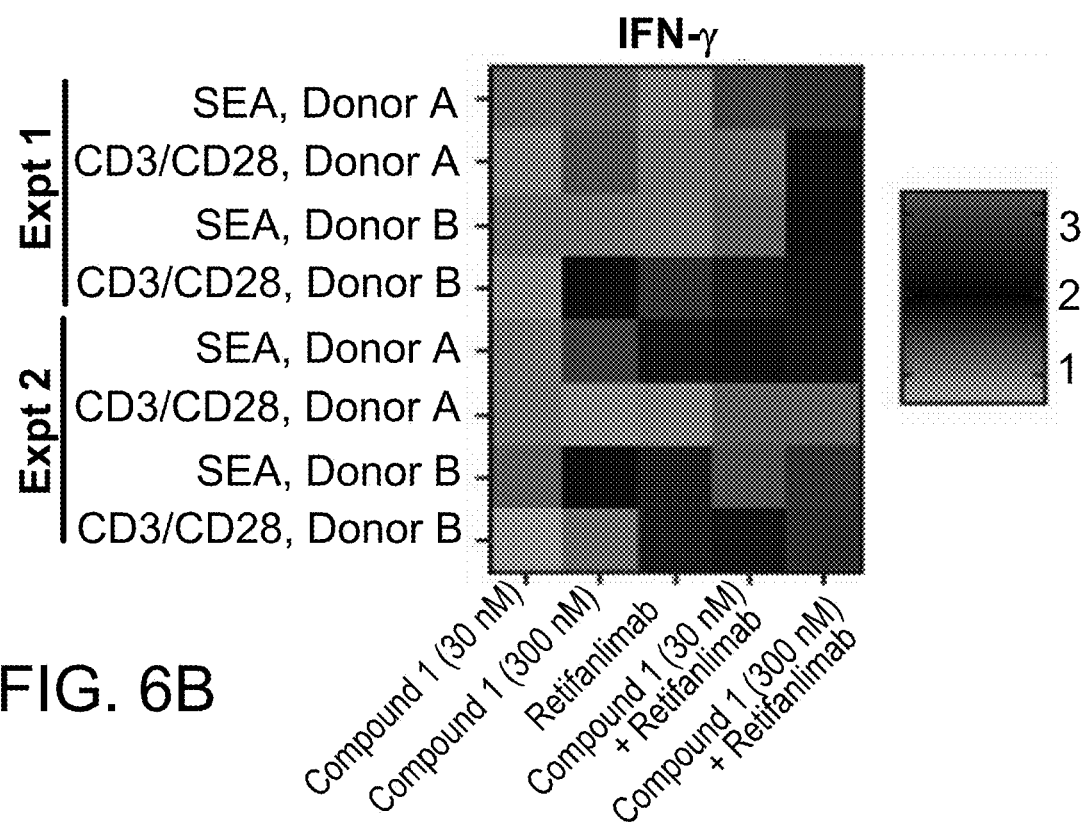
FIG. 6B is a heatmap showing the in vitro induction of interferon (IFN)-γ by Compound 1 and/or retifanlimab in PBMCs.
Figure 6C:
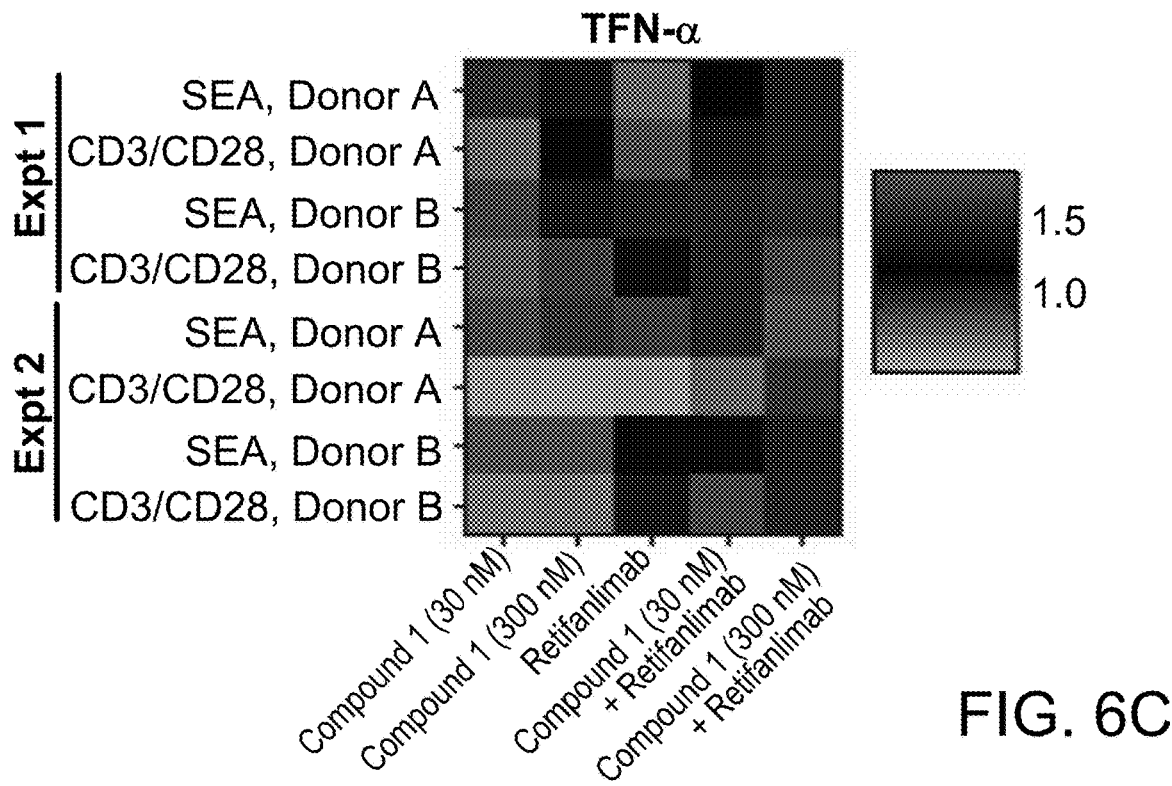
FIG. 6C is a heatmap showing the in vitro induction of tumor necrosis factor (TNF)-α by Compound 1 and/or retifanlimab in PBMCs.
Figure 6D:
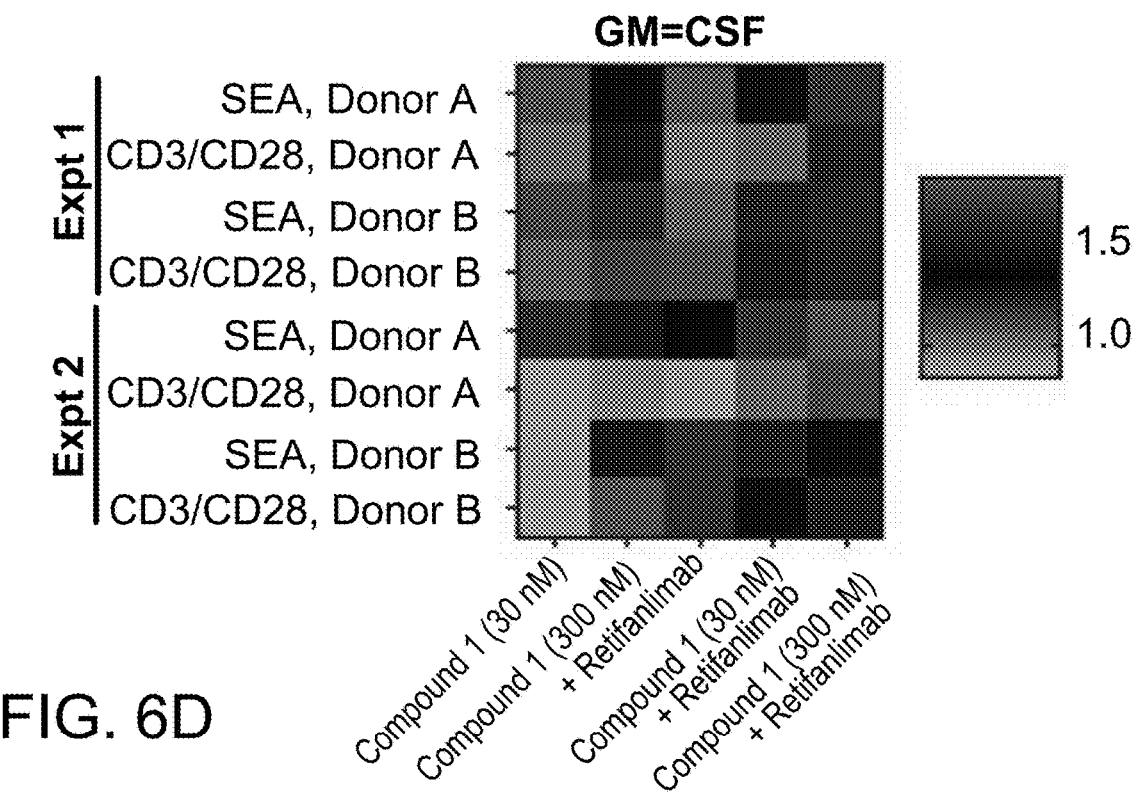
FIG. 6D is a heatmap showing the in vitro induction of granulocyte-macrophage colony-stimulating factor (GM-CSF) by Compound 1 and/or retifanlimab in PBMCs.
Figure 6E:
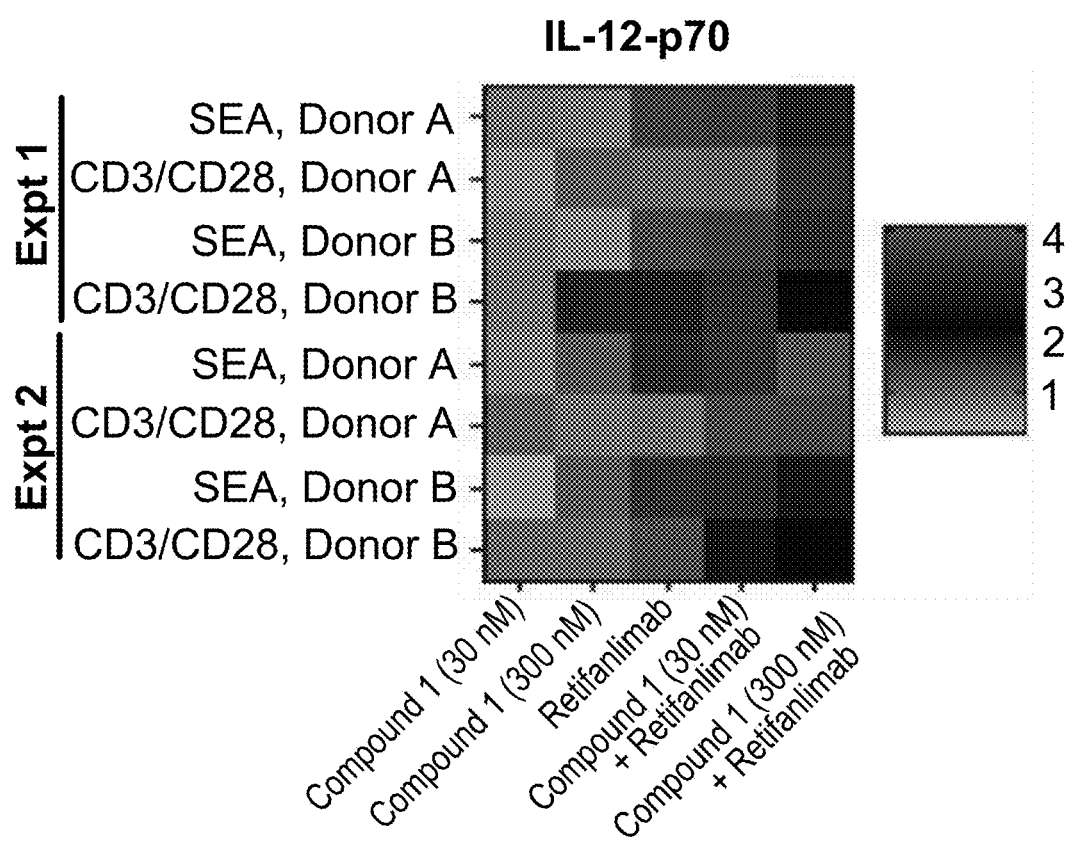
FIG. 6E is a heatmap showing the in vitro induction of IL-12 p70 by Compound 1 and/or retifanlimab in PBMCs.

Compound 1 alone induced IFN-γ, tumor necrosis factor-α, granulocyte-macrophage colony-stimulating factor and moderately induced IL-12 p70 (FIG. 6B-6D). While retifanlimab also induced these cytokines in a subset of donors, the combination of Compound 1 and retifanlimab demonstrated a marked increase in cytokine production compared with individual agents (FIG. 6), including IL-2 (FIG. 6A). These data demonstrate that combination of Compound 1 with checkpoint blockade can induce proinflammatory cytokine production in vitro.

Example H. In Vivo Efficacy Studies

To test potential immunomodulatory activity of Compound 1 in vivo, antitumor efficacy studies were performed in syngeneic tumor models.

Patient-derived xenograft (PDX) models are a commonly used animal tumor model with which to evaluate the antitumor efficacy of anticancer drugs (Jin K, Teng L, Shen Y, He K, Xu Z, Li G. Patient-derived human tumour tissue xenografts in immunodeficient mice: a systematic review, Clin Transl Oncol (2010) 12:473-80. doi: 10.1007/s12094-010-0540-6). A PDX model is generated by implanting fresh cancer tissue from patients directly into immunocompromised mice. These models are different from cell-based xenograft models in that a PDX model is never passaged in vitro, whereas cell-based xenografts are generated by implanted cells grown in tissue culture. PDX models have been shown to retain the genetic makeup and tissue morphology of primary patient tumors, making them valuable tools in preclinical drug discovery (Izumchenko E, Paz K, Ciznadija D, Sloma I, Katz A, Vasquez-Dunddel D, et al. Patient-derived xenografts effectively capture responses to oncology therapy in a heterogeneous cohort of patients with solid tumors. Ann Oncol (2017) 28:2595-605. doi: 10.1093/annonc/mdx416). PDX models have been utilized to evaluate the response of anticancer drugs in tumor models across cancer indications (Gao H, Korn J M, Ferretti S, Monahan J E, Wang Y, Singh M, et al. High-throughput screening using patient-derived tumor xenografts to predict clinical trial drug response. Nat Med (2015) 21:1318-25. doi: 10.1038/nm.3954). These studies have proved useful in identifying models that respond to treatment, as well as those that do not respond, which can occur amongst tumors in the same cancer indication.

MBT-2 cells were obtained from the Japanese Collection of Research Bioresources Cell Bank and were maintained in DMEM supplemented with 10% FBS. MC38 cells were obtained from the NCI. 4T1 cells were obtained from ATCC and maintained in RPMI media supplemented with 10% FBS. For MBT-2 experiments, 5×10⁵ MBT-2 cells were inoculated subcutaneously into the right hind flank of 6- to 8-week-old C3H mice or athymic nude mice (Charles River Laboratories, Wilmington, Mass.). For MC38 studies, 12-week old female C57BL/6 mice were inoculated with brei of MC38 tumors (in-vivo passage 6) into the right hind flank. For 4T1 studies, 7.5×10⁵ 4 T1 cells were inoculated subcutaneously into the right hind flank of 6- to 8-week-old female BALB/c mice or athymic nude mice (Charles River Laboratories). Mice were randomized by tumor volume with n=10-12 per group. Compound 1 was dosed orally twice a day (BID) continuously from the start to the end of study. In the MC38 study, anti-programmed death ligand 1 (PD-L1) (BE0101, Bio X Cell, West Lebanon, NH) was dosed intraperitoneally at 15 mg/kg twice a week. The vehicle group and Compound 1 group were also administered rat IgG2b control antibody twice a week (BE0090, Bio X Cell) beginning at the start of treatment. In the 4T1 study, a single dose of anti-PD-L1 was dosed intraperitoneally at 15 mg/kg at the start of the study. In the combination studies, the vehicle control group and mice receiving anti-PD-L1 were dosed with vehicle BID continuously until the end of study. Vehicle and Compound 1 were dosed orally BID. Mice were monitored for tumor growth and overt tolerability over the course of the experiment. PDX tumor models were conducted at Champions Oncology (Hackensack, N.J.). PDX tumors were implanted into 6- to 8-week-old female athymic nude mice. When tumor volumes were approximately 150-250 mm³, mice were randomized by tumor volume and were administered Compound 1 at 10, 30 or 100 mg/kg BID by oral gavage. Tumor volume was calculated using the formula $(L \times W^2)/2$, where L and W refer to the length and width dimensions, respectively. Tumor growth inhibition (TGI) was calculated using the formula $(1-(V_T/V_C)) \times 100$, where $V_T$ is the tumor volume of the treatment group on the last day of treatment, and $V_C$ is the tumor volume of the control group on the last day of treatment. Two-way analysis of variance (ANOVA) with Dunnett's multiple comparisons test was used to determine statistical differences between treatment groups (GraphPad Prism). Animals were housed in a barrier facility fully accredited by the Association for Assessment and Accreditation of Laboratory Animal Care, International. All of the procedures were conducted in accordance with the US Public Service Policy on Human Care and Use of Laboratory Animals and with Incyte Animal Care and Use Committee Guidelines.

At the end of study, tumors were collected 4 hours after the last dose of Compound 1 and placed on ice. Tumor samples were cut into 2-mm pieces and transferred to Miltenyi C Tubes (Miltenyi Biotec; #130-096-334). Tumor dissociation was conducted according to the manufacturer's protocol (Miltenyi Biotec; #130-096-730). The filter was rinsed with cold PBS and samples pelleted. Red blood cells were lysed in Pharm Lyse (BD Biosciences; #555899). Cells were washed with PBS and resuspended in PBS with Live/Dead stain (LifeTech Scientific, Shenzhen, China; #L34966) for 15 minutes at room temperature. Cells were then washed in PBS and resuspended in stain buffer (BD; #554657) and the following antibodies were added to the samples for 30 minutes at 4° C.: CD3 (BD; #553062), CD45 (BD; #564279), CD8 (BD; #560182), CD4 (BD; #552775), CD11b (BD; #557657), F4/80 (eBiosciences, San Diego, Calif.; #12-4801-82), MHC Class II (BD; #562564) and CD206 (BioLegend; #141708). Cells were washed, fixed and permeabilized with fixation/permeabilization buffer (eBioscience 00-5523-00). Cells were re-suspended in permeabilization buffer (eBioscience; 00-8333). Ki-67 antibody (BioLegend, San Diego, Calif.; #652413) was added to the samples for 1 hour at room temperature. Cells were then washed and re-suspended in stain buffer (BD; #554657) for acquisition. M1 macrophages were identified within the CD45$^+$, CD11b$^+$ F4/80$^+$ population as MHC Class II$^{Hi}$/CD206$^{Lo}$ and M2 macrophages were identified as MHC Class II$^{Lo}$/CD206$^{Hi}$. Data were acquired on a BD Fortessa and analyzed with FlowJo software. Levels of interferon (IFN)-γ within tumors were quantitated with a multiplexed protein detection kit according to the manufacturer's protocol (MesoScale Diagnostics, Rockville, Md.). Statistical significance was determined by one-way ANOVA with Dunnett's multiple comparisons test (GraphPad Prism).

Figure 7B:
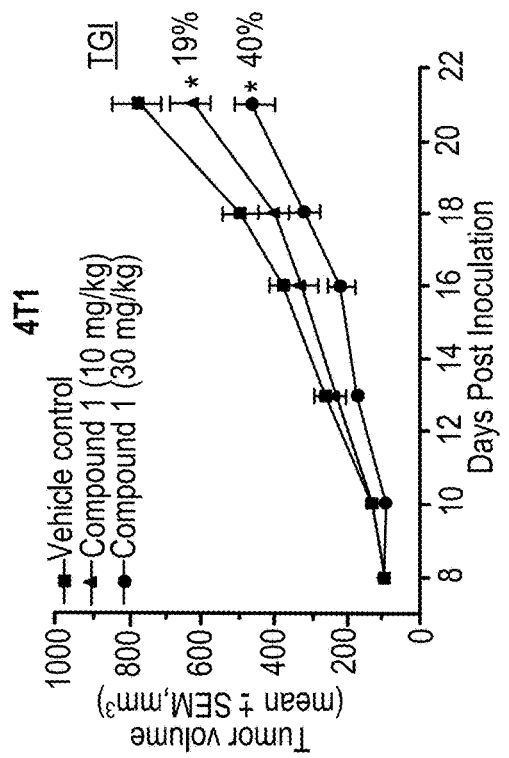
FIG. 7B is a plot of 4T1 tumor volume following treatment with Compound 1, demonstrating tumor growth inhibition efficacy of Compound 1 in the 4T1 tumor model in BALB/c mice.
Figure 7D:
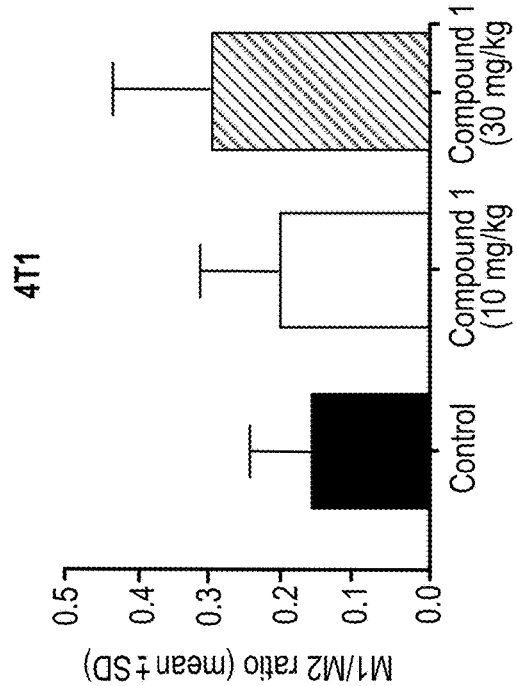
FIG. 7D is a graph of the ML/M2-like macrophage ratio of 4T1 tumor-bearing mice treated with Compound 1.
Figure 7A:
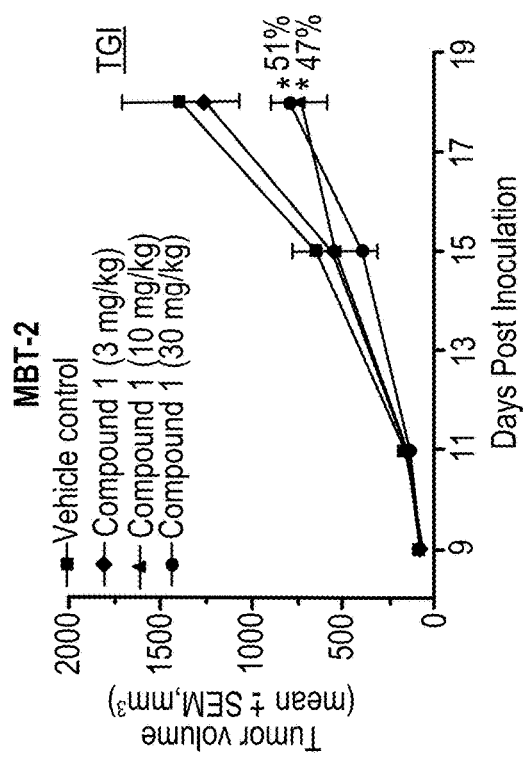
FIG. 7A is a plot of MBT-2 tumor volume following treatment with Compound 1, demonstrating tumor growth inhibition efficacy of Compound 1 in the MBT-2 tumor model in C3H mice.
Figure 7C:
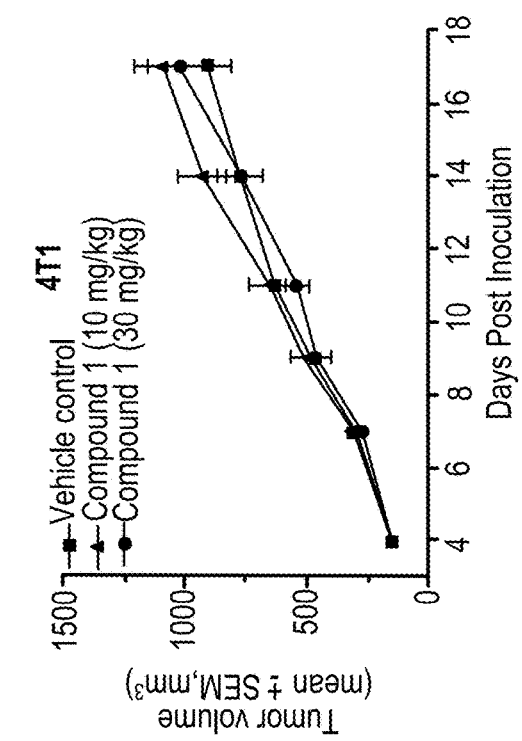
FIG. 7C is a plot of 4T1 tumor volume following treatment with Compound 1, demonstrating tumor growth inhibition efficacy of Compound 1 in the 4T1 tumor model in athymic nude mice.

Compound 1 induced dose-dependent efficacy in the MBT-2 and 4T1 tumor models (FIGS. 7A and 7B). There was no activity in immunodeficient mice bearing the same tumors, demonstrating the antitumor activity was dependent on a functional immune system, at least in these models (FIG. 7C). In the 4T1 model, Compound 1 treatment increased the ratio of M1-like to M2-like macrophages in a dose-dependent manner (FIG. 7D). Based on the observed enhanced in vitro activity with primary human PBMCs, Compound 1 was tested in combination with checkpoint blockade in vivo. In the MC38 model, both Compound 1 and anti-PD-L1 had single-agent antitumor activity, but significantly higher activity in combination (FIG. 8A). Both single-agent treatments induced proliferation of CD4$^+$ and CD8$^+$ tumor-infiltrating lymphocytes, and to a higher degree in combination (FIGS. 8B and 8C). Combination treatment also resulted in increased IFN-γ levels in tumors compared with single-agent treatment (FIG. 8D). These data demonstrate that Compound 1 induced macrophage polarization, increased functional CD4$^+$ and CD8$^+$ T-cell activity and combined with checkpoint blockade to enhance antitumor activity in vivo.

Example I. Sarcoma PDX Models

The activity of Compound 1 in sarcoma PDX models was evaluated as described in Example H for PDX models. Athymic nude mice bearing (a) CTG-2041, (b) CTG-1302, or (c) CTG-1339 tumors were dosed orally twice a day with Compound 1 at 10 mg/kg, 30 mg/kg, and 100 mg/kg. CTG-2041 or CTG-1339 tumors from mice treated with Compound 1 or vehicle were lysed and processed by Western blot for pAXL, AXL, pMER, MER, GAS6, pAKT, AKT, and β-Actin. Three mice per group were analyzed. Western blot data were obtained from different gels. The experiment with CTG-2041 tumors represents a model of angiosarcoma. The experiment with CTG-1302 tumors represents a model of leiomyosarcoma. The experiment with CTG-1339 tumors represents an osteosarcoma model.

Figure 9D:
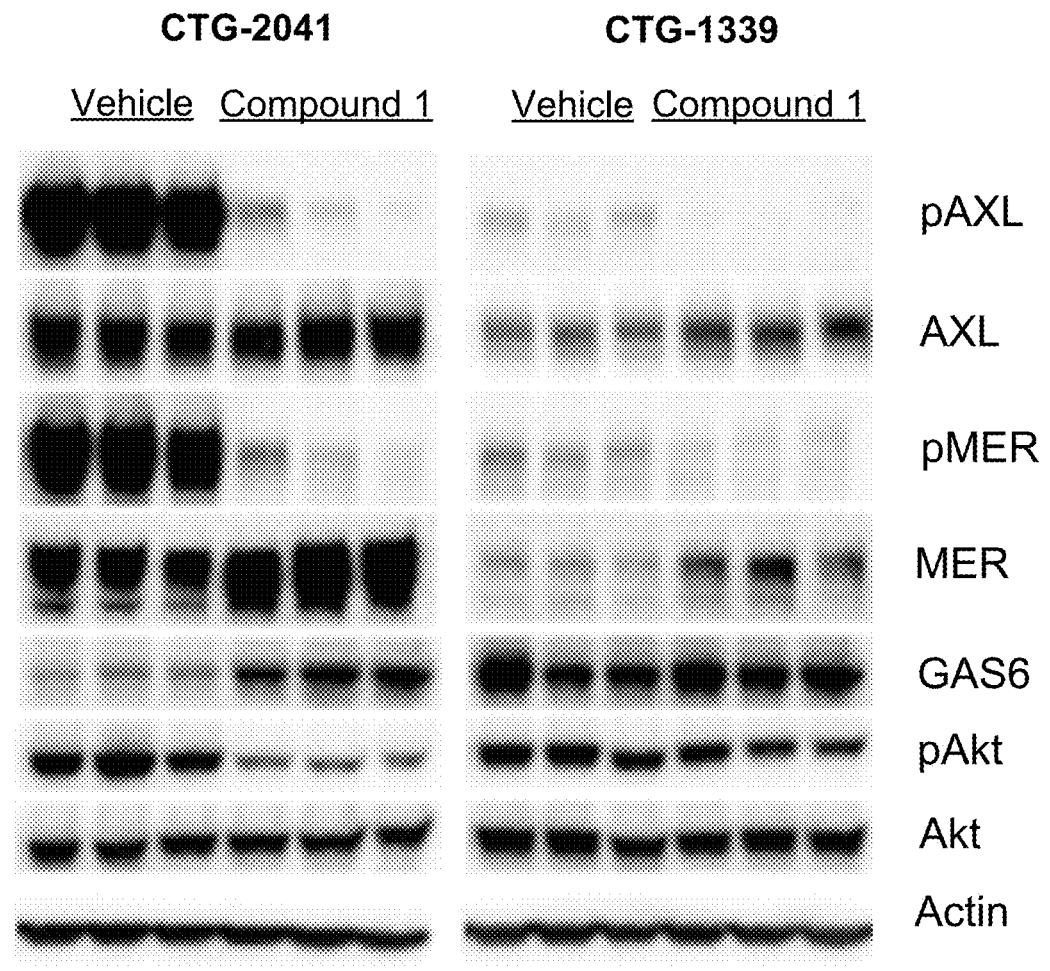
FIG. 9D shows the Western blot for pAXL, AXL, pMER, MER, GAS6, pAKT, AKT, and β-Actin of CTG-2041 or CTG-1339 tumors from mice treated with Compound 1 or vehicle.

A strong antitumor response was observed in CTG-2041 with equivalent activity at 10, 30 and 100 mg/kg BID Compound 1 dosing and demonstrated 95% TGI (FIG. 9A). A robust antitumor response was also observed in CTG-1302 (FIG. 9B). In contrast, CTG-1339 was resistant to Compound 1 treatment (FIG. 9C). To understand potential mechanisms responsible for the differences observed in responder compared to nonresponder models, the impact of Compound 1 on AXL and MER activation as well as downstream signaling in CTG-2401 and CTG-1339 tumors was evaluated (FIG. 9D). While Compound 1 inhibited pAXL and pMER in both models, CTG-2041 expressed significantly higher levels of total AXL and MER, especially pAXL and pMER (FIG. 9D). pAKT was only inhibited in CTG-2041, correlating with the antitumor efficacy of Compound 1. Compound 1 treatment also increased total MER levels in both tumor models, as well as GAS6 levels in CTG-2041.

The experiment was further conducted in athymic nude mice bearing (a) CTG-2426 (myxofibrosarcoma) and (b) CTG-1861 (gastrointestinal stromal) tumors. Results of these experiments are shown in the table below.

| Model | Subtype | TGI (%) |
| --- | --- | --- |
| CTG-2426 | Myxofibrosarcoma | 42 |
| CTG-1861 | Gastrointestinal stromal tumor | 74 |

Example J. Humanized Mouse Model

Animals were housed in a barrier facility fully accredited by the Association for Assessment and Accreditation of Laboratory Animal Care, International. All of the procedures were conducted in accordance with the US Public Service Policy on Human Care and Use of Laboratory Animals and with Incyte Animal Care and Use Committee Guidelines. Five million H1299 cells (ATCC) were implanted subcutaneously into the right-hind flank of 20- to 24-week-old female human CD34$^+$ reconstituted NSG mice (The Jackson Laboratory, Bar Harbor, Me.). Cell inoculations included Matrigel (#354248; Corning, N.Y.) in a 1:1 volume ratio in phosphate-buffered saline (PBS). When tumor volumes averaged ~150 mm$^3$, mice were randomized by both tumor volume and donor (2-5 donors per group) into groups of 10 and treated with either vehicle plus a human IgG1 isotype control antibody, Compound 1, retifanlimab, or the combination. Compound 1 was dissolved in 50 mM citrate buffer in 0.5% methyl cellulose and was orally dosed at 30 mg/kg BID. Retifanlimab was diluted in PBS and was dosed every 5 days intraperitoneally at 5 mg/kg. Tumor growth inhibition (TGI) was calculated using the formula $(1-(V_T/V_C))*100$, where $V_T$ is the tumor volume of the treatment group on the last day of treatment and $V_C$ is the tumor volume of the control group on the last day of treatment. Statistical analysis was performed using two-way analysis of variance.

Example K. Phase 1 Study

This Example describes a Phase 1, open-label study intended to evaluate the safety and tolerability, pharmacokinetics, pharmacodynamics, and preliminary efficacy of single-agent Compound 1 (Part 1) and Compound 1 in combination with retifanlimab (Part 2).

Both Part 1 and Part 2 comprise a dose-finding and dose-expansion. Parts 1A and 1B enroll participants with select solid tumors; Part 1C enrolls participants with AML. Parts 2A and 2B only enrolls participants with select solid tumors. Study treatment continues until disease progression, unacceptable toxicity, death, withdrawal of consent, or any other treatment withdrawal criterion is met.

Part 1: Single Agent Compound 1

The study begins with Part 1A. Initially, 3 participants in the starting dose level cohort receive a single dose of Compound 1 followed by a timed PK assessment to confirm exposure approximately 1 week before continuous administration is initiated. The dose level for continuous administration for each participant is determined based on the exposures at this PK assessment according to the exposure-based dosing guidelines listed below:

If $AUC_{0-24\,h}$ from the single-dose PK analysis is between >1000 nM·h but <2000 nM·h and $C_{24h}$, is ≥15 nM, then continuous dosing initiates at the single-agent Compound 1 dose of 10 mg once daily (QD).

If $AUC_{0-24\,h}$ from the single-dose PK analysis is >2000 nM·h and $C_{24h}$, is >15 nM, then continuous dosing initiates at 5 mg QD.

If $AUC_{0-24\,h}$ from the single-dose PK analysis is <1000 nM·h or $C_{24h}$, <15 nM, then continuous dosing initiates at 15 mg QD.

If $AUC_{0-24}$ h from the single-dose PK analysis is >15,000 nM·h or $C_{24h}$>50 nM, then the participant's exposure levels are evaluated by the medical monitor to determine whether the participant can be safely treated or if the participant will be discontinued from study treatment.

The dose escalation originates at the lowest dose administered among the initial 3 participants. For example, if 1 of the initial 3 participants receives 5 mg QD, the designated starting dose level cohorts will then be 5 mg QD and assessed for safety and tolerability using a 3+3+3 study design. Based on this scenario, participants are enrolled in the 5 mg cohort until there are sufficient participants and data to declare the 5 mg dose tolerable. Similarly, if the lowest dose among the initial 3 participants is 10 mg QD or 15 mg QD, then 10 mg QD or 15 mg QD, respectively, will be the designated starting dose level, and participants would be enrolled in the lowest dose level cohort until that dose level cohort was to be declared tolerable. Any of the initial 3 participants in the single-dose PK analysis who initiates on a dose higher than the designated starting dose of Compound 1 remains on his or her exposure-based dose and is included in the corresponding dose level cohort analysis.

In the event that levels from the initial 3 participants on Cycle 1 Day 1 are below target exposures ($AUC_{0-24\,h}$ 1000 nM·h OR C24 h is ≤15 nM), the next dose level increase may be greater than 50% but not more than 100%. A single-dose PK analysis is performed in the initial 3 participants in any dose level cohort in which the dose is increased greater than 50%, and may be performed in additional participants or at any other dose level cohorts at the sponsor's discretion. The dose-finding scheme for Compound 1 is listed below:

| Dose Level | Dose of Compound 1 | Frequency of Administration |
|---|---|---|
| Dose Level 1 | 5 mg | QD in 28-day cycles |
| Starting Dose/Dose Level 1 | 10 mg | QD in 28-day cycles |
| Dose Level 2 | 15 mg | QD in 28-day cycles |
| Dose Level 3 | 20 mg | QD in 28-day cycles |
| Dose Level 4 | 30 mg | QD in 28-day cycles |
| Dose Level 5 | 45 mg | QD in 28-day cycles |
| Dose Level 6 | 60 mg | QD in 28-day cycles |
| Dose Level 7 | 90 mg | QD in 28-day cycles |
| Dose Level 8 | 120 mg | QD in 28-day cycles |

Upon selection of a recommended dose for expansion ("RDE") in Part 1A, Part 1B is initiated.

Part 1B includes 4 independent tumor-specific (melanoma, NSCLC, SCCHN, and soft-tissue sarcoma) dose expansion cohorts of approximately 12 participants each to further characterize the safety, tolerability, efficacy, and pharmacodynamic effects of the RDE of Compound 1. Paired tumor biopsies (pretreatment and then between Cycle 2 Day 1 and Cycle 3 Day 1) are required from all participants in Part 1B. Once safety data are available from the Part 2A combination escalation of Compound 1 and retifanlimab and a dose of the combination has been determined to be safe and tolerated, ongoing participants in the Part 1B dose expansion cohorts, after completion of the initial on-treatment biopsy and tumor imaging and with sponsor approval, may also receive retifanlimab. Part 1B participants who initiate combination therapy are required to repeat Cycle 1 and Cycle 2 safety and PK assessments and must agree to a repeat biopsy to occur 4 to 8 weeks after initiating combination treatment. The dose of Compound 1 does not exceed the doses tested and determined to be safe and tolerable in combination with retifanlimab in Part 2A.

Part 1C of the study may also begin upon identification of an RDE in Part 1A, and is conducted in parallel to Part 1B. Initiation of enrollment into this expansion cohort is subject to the discretion of the sponsor. This part of the study enrolls participants with relapsed and/or refractory AML into 1 independent expansion cohort and evaluates the safety, tolerability, and preliminary efficacy of the RDE of Compound 1 in this population. Part 1C uses a Simon 2-stage design with a stopping rule to allow for early termination at the end of Stage 1 if there are no responses observed. During Stage 1, 10 participants are enrolled; if no objective responses are observed, then there will be no further enrollment in order to minimize the number of participants treated without evidence of clinical activity. If at least 1 objective response is observed, then up to 19 additional participants may be enrolled into that cohort for a maximum of 29 enrolled in Part 1C.

Part 2: Compound 1 in Combination with Retifanlimab

Part 2 comprises Part 2A and Part 2B. Part 2A is a dose-finding stage, which is performed using a 3+3+3 design to assess the safety and tolerability of Compound 1 in combination with retifanlimab in participants with select advanced solid tumors.

Part 2A begins once a dose level is cleared as safe and tolerable in Part 1A and may enroll in parallel with Part 1A but at 1 dose level below the currently established tolerable dose.

The dose-finding schema for Compound 1 in combination with retifanlimab is listed below:

| Dose Level | Dose of Compound 1 | Compound 1 Administration | Dose of retifanlimab | retifanlimab Administration |
|---|---|---|---|---|
| Dose level 1/ starting dose | One dose level below highest safe/tolerable dose established in Part 1A at the time the combination is initiated. | QD in 28-day cycles | 500 mg | IV once every four weeks |
| Dose level ≥2 | Next dose level selected as tolerable not to exceed the Part 1A MTD and/or RDE. | QD in 28-day cycles | 500 mg | IV once every four weeks |

Part 2B is a dose expansion to further evaluate the safety, tolerability, efficacy, and pharmacodynamic effects at the RDE of Compound 1 in combination with retifanlimab determined in Part 2A. Four independent tumor-specific (melanoma, NSCLC, SCCHN, and soft-tissue sarcoma) expansion cohorts of approximately 12 participants each will be enrolled. Paired tumor biopsies (pretreatment and then between Cycle 2 Day 1 and Cycle 3 Day 1) are required from all participants in Part 2B.

Study Treatment

Compound 1 is administered as an oral capsule QD in each 28-day cycle. Retifanlimab is administered via IV on Day 1 of each 28-day cycle. Study drug(s) continue with either the single-agent or combination regimens until disease progression, an adverse event requiring drug discontinuation, or participant or physician decision. Participants continue on treatment if deriving benefit for up to 1 year; at that time, the investigator and sponsor will discuss whether it is clinically appropriate to continue treatment.

Participants should take Compound 1 at approximately the same time each morning. The schedule of administration may be adjusted based on emerging PK observations.

Inclusion Criteria

Participants are eligible to be included in the study only if all of the following criteria apply:

First, all participants must be at least 18 years of age.

Part 1A, 1B, 2A, and 2B: Histologic or cytologic evidence of a solid neoplasm for which no standard therapy is available, or have progressed despite standard therapy or are intolerant to standard therapy, which may include chemotherapy, targeted therapy, biological therapy, and immunotherapy, inclusive of the cohort-specific requirements outlined below:

Measurable lesions per RECIST v1.1 that are considered nonamenable to surgery or other curative treatments or procedures, with at least 1 target lesion available for evaluation. Tumor lesions located in a previously irradiated area or in an area subjected to other locoregional therapy are considered measureable if progression has been demonstrated in the lesion.

Part 1A and Part 2A only: Advanced or metastatic gastric or GEJ adenocarcinoma, HCC, melanoma, NSCLC, RCC, soft-tissue sarcoma, SCCHN (recurrent or metastatic), TNBC, or urothelial carcinoma. Additional tumor histologies including MSI-H tumors may be allowed with approval from the medical monitor.

Part 1B and 2B Only:

Cohort 1: advanced or metastatic melanoma

Must have received available standard of care, including but not limited to 1 prior PD-1/L1 containing regimen (either as a single agent or in combination), received at least 2 doses of the anti-PD-1/L1 agent, and experienced PD during or after treatment.

Known BRAF status (V600e and V600k).

Ocular melanoma is excluded.

Cohort 2: Advanced or Metastatic NSCLC

Must have received available standard of care treatments, including but not limited to 1 prior PD-1/L1 containing regimen (either as a single agent or in combination), received at least 2 doses of the anti-PD-1/L1 agent, and experienced PD during or after treatment.

Participants with tumors harboring known driver mutations (EGFR, ALK, ROS1, BRAF) who have previously been treated with appropriate targeted agents are allowed to enroll.

Known PD-L1 expression status and/or TPS

Cohort 3: Recurrent or Metastatic SCCHN

Must have received available standard of care, including but not limited to 1 prior PD-1/L1 containing regimen (either as a single agent or in combination), received at least 2 doses of the anti-PD-1/L1 agent, and experienced PD during or after treatment.

Known PD-L1 expression status and/or TPS

Carcinoma of the nasopharynx, thyroid, salivary gland, or nonsquamous histologies are excluded.

Cohort 4: Advanced or Metastatic Soft-Tissue Sarcoma

Must have received available standard of care

Eligible subtypes include leiomyosarcoma, poorly differentiated/dedifferentiated liposarcoma, high-grade pleomorphic undifferentiated sarcoma/MFH, myxofibrosarcoma, malignant peripheral nerve sheath tumor, epithelioid sarcoma, clear cell sarcoma, synovial sarcoma, rhabdomyosarcoma, fibrosarcoma, and angiosarcoma; additional histologies may be enrolled with the approval of the medical monitor.

Must not have received prior anti-PD-1/L1 targeted treatment.

Part 1C: Relapsed and/or primary refractory AML as defined by WHO criteria; acute promyelocytic leukemia (M3), therapy-related AML, and transformed MDS are excluded.

Exclusion Criteria

Participants are excluded from the study if any of the following criteria apply:

1. Participants receiving potent inhibitors or inducers of CYP3A4.
   a. A washout period of ≥5 half-lives prior to the first dose of Compound 1 is required for enrollment into the study for prior treatment with potent CYP3A4 inhibitors.
   b. A washout period of ≥14 days prior to the first dose of Compound 1 is required for enrollment into the study for any participant treated with CYP3A4 inducers.
2. Participants with macular degeneration, proliferative diabetic retinopathy or diabetic retinopathy with macular edema, retinal vein occlusions, uveitis, central serous retinopathy, leukemic retinopathy, inherited retinal degenerations, known family history of inherited retinal degenerations, and participants at risk for angle closure glaucoma from pupillary dilation are ineligible. Participants with other clinically significant abnormalities identified during ophthalmic screening examinations that may confound ocular monitoring are ineligible. Investigators should contact the medical monitor to discuss eligibility if abnormalities are identified during ophthalmic screening examinations.
3. Clinically significant cardiac disease, including LVEF <40%, unstable angina, acute myocardial infarction within 6 months of Cycle 1 Day 1, New York Heart Association Class III or IV congestive heart failure, and arrhythmia requiring therapy.
4. History or presence of an ECG that, in the investigator's opinion, is clinically meaningful. Screening QTcF interval >480 milliseconds is excluded In the event that a single QTc is >480 milliseconds, the participant may enroll if the average QTc for the 3 ECGs is <480 milliseconds. For participants with an intraventricular conduction delay (QRS interval >120 milliseconds), the JTc interval may be used in place of the QTc with sponsor approval. The JTc must be ≤340 milliseconds if JTc is used in place of the QTc. Participants with left bundle branch block are excluded.
5. Untreated brain or CNS metastases or brain or CNS metastases that have progressed (eg, evidence of new or enlarging brain metastasis or new neurological symptoms attributable to brain or CNS metastases). Participants who have previously treated and clinically stable brain or CNS metastases and who are off all corticosteroids for ≥2 weeks are eligible.
6. Participants who have active or inactive autoimmune disease or syndrome either independent of prior therapy or induced by prior immune checkpoint inhibitor therapy (eg, rheumatoid arthritis, moderate or severe psoriasis, multiple sclerosis, inflammatory bowel disease) that has required systemic treatment in the past 2 years or who are receiving systemic therapy for an autoimmune or inflammatory disease (ie, with use of disease modifying agents, corticosteroids, or immunosuppressive drugs).
7. Participants with prior Grade 3 or higher immune-related AEs or any ocular toxicity on prior immunotherapy. The following Grade 3 or higher AEs are permitted:
   a. Grade 3 rashes that resolved with topical therapy.
   b. Asymptomatic lipase elevations that do not require treatment interruption.
   c. Autoimmune conditions allowed per exclusion criterion #6 above.
8. Laboratory values not within the Protocol-defined range. If the screening chemistry and hematology tests below were conducted >7 days before treatment initiation, then the tests must be repeated and eligibility confirmed before study drug administration on Cycle 1 Day 1. Participants with screening laboratory values as follows are ineligible:

| Laboratory Parameter | Part 1A/1B and Part 2 (Solid Tumors) | Part 1C (AML) |
|---|---|---|
| a. Platelets | <100 × 109/L | <50 × 109/L |
| b. Hemoglobin | <9 g/dL or <5.6 mmol/L | N/A |
| c. Absolute Neutrophil Count ("ANC") | <1.5 × 109/L | <0.5 × 109/L |

| Laboratory Parameter | All participants |
|---|---|
| d. Aspartate aminotransferase ("AST") and Alanine aminotransferase ("ALT") | ≥2.5 × upper limit of normal ("ULN") (AST and/or ALT >5 × ULN in participants with liver metastases) |
| e. Alkaline phosphatase | ≥2.5 × ULN or alkaline phosphatase ≥5 × ULN for participants with 1) bone metastases and 2) no hepatic parenchymal metastases on screening radiographic examinations |
| f. Total bilirubin | ≥1.2 × ULN, unless conjugated bilirubin is ≤ ULN (conjugated bilirubin only needs to be tested if total bilirubin exceeds the ULN). If there is no institutional ULN, then direct bilirubin must be <40% of total bilirubin |
| g. Serum creatinine | >1.5 × institutional ULN or creatinine clearance <50 mL/min for participants with creatinine levels >1.5 × institutional ULN |
| h. INR or PT | >1.5 × ULN |
| i. aPTT | >1.5 × ULN |

9. Participants receiving any vitamin K antagonists, including but not limited to acenocoumarol, fluindione, phenprocoumon, and warfarin, are excluded.
10. Treatment with anticancer medications or investigational drugs within the following intervals before the first administration of study drug:
    a. At least 14 days for chemotherapy, targeted small molecule therapy, or radiation therapy. Participant must not have had radiation pneumonitis as a result of treatment. A 1-week washout period is permitted for palliative radiation to non-CNS disease with sponsor approval.
    b. At least 28 days for a prior monoclonal antibody used for anticancer therapy. For other agents with long half-lives (eg, >5 days), enrollment before the fifth half-life requires medical monitor approval.
11. Has not recovered to <Grade 1 or baseline from toxic effects of prior therapy (including prior immunotherapy) and/or complications from prior surgical intervention before starting study treatment; stable chronic toxicities not expected to resolve, such as peripheral neurotoxicity, alopecia, and fatigue are allowed.
12. No use of systemic corticosteroids within 7 days before the first dose of study treatment.
13. Receipt of a live vaccine within 3 months of the first dose of study treatment 14. Active infection requiring systemic therapy. A 28-day washout for systemic antibiotics is required. Probiotic usage while on study and during screening is prohibited.
15. Evidence of HBV or HCV infection or risk of reactivation. Hepatitis B virus DNA and HCV RNA must be undetectable. Participants cannot be positive for HBV DNA, HCV RNA, hepatitis B surface antigen, or anti-hepatitis B core antibody.
16. Known history of HIV (HIV 1/2 antibodies).
17. Known hypersensitivity or severe reaction to any component of study drugs or formulation components.
18. Is pregnant or breastfeeding or expecting to conceive or father children within the projected duration of the study, starting with the screening visit through 180 days after the last dose of study treatment.
19. Any condition that would, in the investigator's judgment, interfere with full participation in the study, including administration of study treatment and attending required study visits; pose a significant risk to the participant; or interfere with interpretation of study data.
20. Inability of the participant (or parent, guardian, or legally authorized representative) to comprehend the ICF or unwillingness to sign the ICF.
21. Participants with known dysphagia, short-gut syndrome, gastroparesis, or other conditions that limit the ingestion or gastrointestinal absorption of drugs administered orally.
22. Part 1C only: Participants who have undergone a HSCT within 60 days of the first dose of Compound 1, or participants on immunosuppressive therapy post-HSCT at the time of screening, or with clinically significant GVHD. (The use of topical steroids for ongoing skin GVHD is permitted.)
23. Part 1C only: Participants with clinical symptoms suggesting active CNS leukemia or known CNS leukemia. Evaluation of cerebrospinal fluid is only required if there is a clinical suspicion of CNS involvement by leukemia during screening.
24. Evidence of interstitial lung disease, history of interstitial lung disease, or active, noninfectious pneumonitis.
25. History of organ transplant, including allogeneic stem cell transplantation (except Cohort 1C).
26. Immune-related toxicity during prior checkpoint inhibitor therapy for which permanent discontinuation of therapy is recommended (per product label or consensus guidelines) OR any immune-related toxicity requiring intensive or prolonged immunosuppression to manage (with the exception of endocrinopathy that is well controlled on replacement hormones).
27. Diagnosis of oculocutaneous albinism.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating cancer in a patient, comprising administering to said patient:
   (i) Compound 1, having the structure:

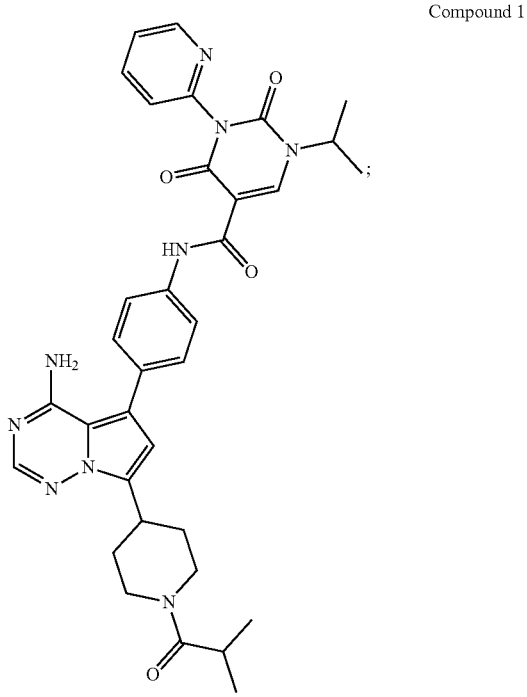 [SMILES: CC(C)C(=O)N1CCC(c2cc(-c3ccc(NC(=O)c4cn(C(C)C)c(=O)n(-c5ccccn5)c4=O)cc3)c3c(N)ncnn23)CC1]

Compound 1 or a pharmaceutically acceptable salt thereof; and
   (ii) an antibody, or an antigen-binding fragment thereof, that binds to human PD-1, wherein the antibody, or the antigen-binding fragment thereof comprises a variable heavy (VH) domain and a variable light (VL) domain, wherein the VH domain comprises the amino acid sequence set forth in SEQ ID NO:4 and the VL domain comprises the amino acid sequence set forth in SEQ ID NO:5;
   wherein the cancer is colorectal cancer.

2. The method of claim 1, wherein Compound 1 and the antibody are administered simultaneously.

3. The method of claim 1, wherein Compound 1 and the antibody are administered sequentially.

4. The method of claim 1, wherein Compound 1 is administered orally.

5. The method of claim 1, wherein the antibody or antigen-binding fragment is administered via intravenous administration.

6. The method of claim 1, wherein the antibody or antigen-binding fragment is administered at a dose of 375 mg once every 3 weeks.

7. The method of claim 1, wherein the antibody or antigen-binding fragment is administered at a dose of 500 mg once every 4 weeks.

8. The method of claim 1, wherein the antibody or antigen-binding fragment is administered at a dose of 750 mg once every 4 weeks.

9. The method of claim 1, wherein:
   (a) the antibody comprises an Fc Region and a Hinge Domain;
   (b) the Fc Region and the Hinge Domain are of the IgG4 type; and
   (c) the Hinge Domain comprises a stabilizing mutation.

10. The method of claim 1, wherein the antibody comprises a heavy chain and wherein the heavy chain comprises the amino acid sequence set forth in SEQ ID NO:2.

11. The method of claim 1, wherein the antibody comprises a light chain and wherein the light chain comprises the amino acid sequence set forth in SEQ ID NO:3.

12. The method of claim 1, wherein the antibody comprises a heavy chain and a light chain, and wherein the heavy chain comprises the amino acid sequence set forth in SEQ ID NO: 2 and the light chain comprises the amino acid sequence set forth in SEQ ID NO:3.

13. The method of claim 1, wherein the antibody comprises an Fc Region that is of the IgG1 type.

14. The method of claim 1, wherein the antibody comprises a heavy chain and wherein the heavy chain comprises the amino acid sequence set forth in SEQ ID NO:13.

15. The method of claim 1, wherein the antibody comprises a light chain and a heavy chain, wherein the heavy chain comprises the amino acid sequence set forth in SEQ ID NO: 13 and the light chain comprises the amino acid sequence set forth in SEQ ID NO:3.

16. The method of claim 1, wherein the antibody is a humanized antibody.

17. The method of claim 1, wherein:
   a) Compound 1 and the antibody are administered sequentially;
   b) Compound 1 is administered orally; and
   c) the antibody or antigen-binding fragment is administered via intravenous administration.

* * * * *